US008541373B2

(12) United States Patent
Sklair-Tavron et al.

(10) Patent No.: US 8,541,373 B2
(45) Date of Patent: Sep. 24, 2013

(54) BCHE ALBUMIN FUSIONS FOR THE TREATMENT OF COCAINE ABUSE

(75) Inventors: Liora Sklair-Tavron, Zichron Yaakov (IL); Moti Rosenstock, Menashe (IL); Liron Shemesh-Darvish, Ramat-Gan (IL); Hussein Hallak, Jerusalem (IL); Victor Piryatinsky, Netanya (IL); Viktor Roschke, Bethesda, MD (US); David Lafleur, Washington, DC (US)

(73) Assignee: Teva Pharmaceutical Industries Ltd., Petach-Tikva (IL)

( * ) Notice: Subject to any disclaimer, the term of this patent is extended or adjusted under 35 U.S.C. 154(b) by 0 days.

(21) Appl. No.: 12/962,410

(22) Filed: Dec. 7, 2010

(65) Prior Publication Data

US 2011/0312900 A1     Dec. 22, 2011

Related U.S. Application Data

(60) Provisional application No. 61/283,791, filed on Dec. 8, 2009, provisional application No. 61/412,205, filed on Nov. 10, 2010.

(51) Int. Cl.
*A61P 25/36*     (2006.01)

(52) U.S. Cl.
USPC ........ 514/17.5; 514/17.7; 514/18.1; 514/21.2

(58) Field of Classification Search
None
See application file for complete search history.

(56) References Cited

U.S. PATENT DOCUMENTS

| | | | |
|---|---|---|---|
| 6,001,625 A | 12/1999 | Broomfield et al. | |
| 6,989,261 B2 | 1/2006 | Watkins et al. | |
| 7,049,121 B2 | 5/2006 | Watkins et al. | |
| 7,438,904 B1 | 10/2008 | Zhan et al. | |
| 7,482,013 B2 | 1/2009 | Ballance et al. | |
| 7,572,764 B2 | 8/2009 | Cohen et al. | |
| 7,731,957 B1 | 6/2010 | Zhan et al. | |
| 2002/0119489 A1 | 8/2002 | Lockridge et al. | |
| 2003/0096401 A1 | 5/2003 | Huse | |
| 2003/0153062 A1 | 8/2003 | Watkins et al. | |
| 2004/0016005 A1 | 1/2004 | Karatzas et al. | |
| 2004/0087014 A1 | 5/2004 | Huse | |
| 2004/0120939 A1 | 6/2004 | Watkins et al. | |
| 2004/0121970 A1 | 6/2004 | Watkins et al. | |
| 2004/0147002 A1 | 7/2004 | Cohen et al. | |
| 2004/0168208 A2 | 8/2004 | Karatzas et al. | |
| 2005/0136044 A1 | 6/2005 | Watkins et al. | |
| 2006/0039870 A1 | 2/2006 | Turner | |
| 2006/0063248 A1 | 3/2006 | Lockridge et al. | |
| 2008/0194481 A1 | 8/2008 | Rosen et al. | |
| 2009/0029914 A1 | 1/2009 | Rosen et al. | |
| 2011/0002888 A1 | 1/2011 | Rosen et al. | |

FOREIGN PATENT DOCUMENTS

| | | |
|---|---|---|
| EP | 1832599 | 9/2007 |
| WO | WO 02/46227 | 6/2002 |
| WO | WO 03/059934 | 7/2003 |
| WO | WO 03/060071 | 7/2003 |
| WO | WO 2005/003296 | 1/2005 |
| WO | WO 2007/146038 | 12/2007 |
| WO | WO 2009/058322 | 5/2009 |

OTHER PUBLICATIONS

Brimijoin at al. (2008) "A Cocaine Hydrolase Engineered from Human Butyrylcholinesterase Selectively Blocks Cocaine Toxicity and Reinstatement of Drug Seeking in Rats," Neuropsychopharmacology 33, pp. 2715-2725.
Carroll at al., (2010) "Effects of cocaine hydrolase on cocaine self-administration under a PR schedule and during extended access (escalation) in rats," Psychopharmacology, PMID: 20972552 (Epub ahead of print).
Gao, et al. (2009) "An Albumin-Bytyrylcholinesterase for Cocaine Toxicity and Addiction: Catalytic and Pharmacokinetic Properties," NIH Public Access Author Manuscript, published in final edited form as Chem. Biol. Interact. Sep. 25, 2008; 175(1-3): 83-87.
Pan et al. (2005) "Computational redesign of human butyrylcholinesterase for anticocaine medication," PNAS vol. 102 (46) pp. 16656-16661.
Sun et al. (2002) "Cocaine Metabolism Accelerated by a Re-Engineered Human Butyrylcholinesterase," JPET vol. 302(2), pp. 710-716.
International Search Report issued Feb. 8, 2011 in connection with PCT International Application No. PCT/US10/59292.
Written Opinion of the International Searching Authority issued Feb. 8, 2011 in connection with PCT International Application No. PCT/US10/59292.
Matthews, R. (2008) "When Animals Fail the Test" The National, Dec. 1, 2008.
Archibald, K and Clotworthy, M. (2007) "Comment on 'The ethics of animal research' by Festing & Wilkinson" EMBO reports, 2007, 8, 794-796.
Olson et al. (2000) "Concordance of the toxicity of pharmaceuticals in humans and in animals," Regul Toxicol Pharmacol. Aug. 2000;32(1)56-67.
FDA (2004) *Innovation or Stagnation, Challenge and Opportunity on the Critical Path to New Medicinal Products.* Rockville, MD, USA: Food and Drug Administration.
FDA (2006) *Guidance for Industry, Investigators, and Reviewers. Exploratory IND Studies*, Rockville, MD, USA; Food and Drug Administration.
Perel et al. (2007) "Comparison of treatment effects between animal experiments and clinical trials: systematic review" BMJ. Jan. 27, 2007; 334(7586): 197.
Weerts et al. (2008) "The Value of Nonhuman Primates in Drug Abuse Research" Experimental and Clinical Pyschopharmacology 2007, vol. 15, No. 4, 309-327.

(Continued)

*Primary Examiner* — John Ulm
(74) *Attorney, Agent, or Firm* — John P. White; Gary J. Gershik; Cooper & Dunham LLP

(57) ABSTRACT

A method of attenuating a biological effect of cocaine exposure in a primate. Such method includes administering to the primate an amount of a BChE-albumin fusion protein comprising the amino acid substitutions A227S, S315G, A356W, and Y360G, wherein the amount of the fusion protein is effective to cause attenuation of the biological effect of cocaine exposure in the primate.

21 Claims, 52 Drawing Sheets

(56) References Cited

OTHER PUBLICATIONS

Howell, L. (2008) "Nonhuman Primate Neuroimaging and Cocaine Medication Development" Experimental and Clinical Pyschopharmacology 2008, vol. 16, No. 6, 446-457.
National Institutes of Health (NIH) (2007) "Equivalent Surface Area Dosage Conversion Factors" Aug. 2007.
Smith et al. (2002) "Preclinical Safety Evaluation Using Nonrodent Species: An Industry/Welfare Project to Minimize Dog Use" ILAR J. 2002;43 Suppl:S39-42.
ICH (International Conference on Harmonisation of Technical Requirements for Registration of Pharmaceuticals for Human Use), (2008) "Guidance on Nonclinical Safety Studies for the Conduct of Human Clinical Trials and Marketing Authorization for Pharmaceuticals" Jul. 15, 2008.
Shippenberg. T.S. and Koob, G.F., (2002) "Recent Advances in Animal Models of Drug Addition" Neuropyschopharmacology: The Fifth Generation of Progress, Chapter 97: Recent Advances in Animal Models of Drug Addiction, p. 1381-1397.
Flagel et al., (2010) "An animal model of genetic vulnerability to behavioral disinhibition and responsiveness to reward-related cues: implications for addiction." Neuropharmacology, 2010:35(2):388-400 (Abstract only).
Ahmed, S.H. (2012) "The Science of Making Drug-Addicted Animals" Neuroscience Jun. 1, 2012;211:107-25. Epub Aug. 10, 2011 (Abstract Only).
Kupferschmidt et al., (2011) "A procedure for studying the footshock-induced reinstatement of cocaine seeking in laboratory rats" J. Vis, Exp. Jan. 6, 2011(47). pii: 2265. (Abstract Only).
Zimmer, B.A. and Roberts, D.C.,(2012) "Cocaine self-administration in rats: hold-down procedures" Methods Mol. Biol. 2012:829:279-90 (Abstract Only).
Fox et al., (1996) "Efficacy of a therapeutic cocaine vaccine in rodent models" Nature Medicine 2, 1129-1132 (Abstract Only).
Wolf et al., (1999) "Cocaine Addiction: Clues from Drosophila on drugs" Current Biology, vol. 9, Issue 20, R770-R772, Oct. 21, 1999 (abstract Only).
Leibman et al., (1990) "Strain, sex and developmental profiles of cocaine metabolizing enzymes in mice" Pharmacology Biochemistry and Behavior, vol. 37, issue 1. Sep. 1990, pp. 161-165 (Abstract Only).
Schwarz et al (1995) "Engineering of human cholinesterases explains and predicts diverse consequences of administration of various drugs and poisons" Pharmacology & Therapeutics, vol. 67, issue 2, 1995, pp. 283-322 (Abstract Only).
Little et al., (1995) "A new placental enzyme in the metabolism of cocaine: An in vitro animal model" American Journal of Obstetrics and Gynecology. vol. 172. issue 5, May 1995, pp. 1441-1445 (Abstract Only).
Gao. Y. and Brimijoin, S. (2005) "Visualizing viral transduction of a cocaine hydrolyzing, human butyrylcholinesterase in rats" Chemico-Biological Interactions, vols. 157-158, Dec. 15, 2005, pp. 97-103 (Abstract Only).
Goodall, R. (2004) "Cholinesterase heterogeneity: pharmacogenetic models and clinical implications" Current Anaesthesia & Critical Care, vol. 15, issue 1, Apr. 2004, pp. 29-35 (Abstract Only).
Riday et al. (2012) "The rewarding and locomotor-sensitizing effects or repeated cocaine administration are distinct and separable in mice" Neuropharmacology. vol. 62, issue 4, Mar. 2012, pp. 1858-1866 (Abstract Only).
Ahmed et al. (2010) "Validation Crisis in Animal Models of Drug Addiction: Beyond Non-Disordered Drug use Toward Drug Addiction" Neuroscience & Biobehavioral Reviews. 35(2):172-84, Nov. 2010. (Abstract only).
Etteriburg, A. (2009) "The Runway Model of Drug Self-Administration" Pharmacology Biochemistry and Behavior 91(3):271-7. 2009. I. (Abstract Only).
Caprioli et al. (2007) "Modeling the Role of Environment in Addiction" Progress in Neuro-Pyschopharmacology and Biological Pyschiatry, vol. 31, issue 8, Nov. 15, 2007, pp. 1639-1653 (Abstract Only).
Czoty et al. (2006) "Influence of Abstinence and Conditions of Cocaine Access on the reinforcing Strength of Cocaine in nonhuman primates" Drug and Alcohol Dependence, 85(3):213-20. 2006. 12/1. (Abstract Only).
Todtenkopf et al. (2002) "Withdrawel Duration Differentially Affects c-Fos Expression in the Medial Prefrontal Cortex and Discrete Subregions of the Nucleus Accumbens in Cocaine-Sensitized Rats" Neuroscience. 114(4):1061-9. 2002. 11/1. (Abstract Only).
Newbern, L.M. (2008) "Yerkes Researches Create Animal Model of Chronic Stress" Press Release, Woodruff Health Science Center of Emory University, 2008.
Pickens et al., (2011) "Neurobiology of the incubation of drug craving" Trends in Neuroscience, Aug. 2011, vol. 34, No. 8, pp. 411-420.
Apr. 28, 2013 Office Action issued in connection with Eurasian patent application No. 201290457.
May 23, 2013 Official Action issued in connection with European patent application No. 10836553.7.
Jun. 28, 2013 Amendment in connection with Eurasian patent application No. 201290437.
Jun. 28, 2013 Amendment in connection with New Zealand patent application No. 601034.
Jul. 5, 2013 Examination Report in connection with New Zealand patent application No. 601034.
Jul. 11, 2013 Amendment in connection with New Zealand patent application No. 601034.
Jul. 23, 2013 Notice of Acceptance connection with New Zealand patent application No. 601034.
Jul. 2, 2013 Office Action issued in connection with Chinese Application No. 201080061221.X.

MRPTWAWWLFLVLLLALWAPARG
EDDIIIATKNGKVRGMNLTVFGGTVTAFLGIPYAQPPLGRLRFKKPQSLTKWSDIWNA
TKYANSCCQNIDQSFPGFHGSEMWNPNTDLSEDCLYLNVWIPAPKPKNATVLIWIYG
GGFQTGTSSLHVYDGKFLARVERVIVVSMNYRVGALGFLALPGNPEAPGNMGLFDQ
QLALQWVQKNIAAFGGNPKSVTLFGESSGAASVSLHLLSPGSHSLFTRAILQSGSFNA
PWAVTSLYEARNRTLNLAKLTGCSRENETEIIKCLRNKDPQEILLNEAFVVPYGTPLG
VNFGPTVDGDFLTDMPDILLELGQFKKTQILVGVNKDEGTWFLVGGAPGFSKDNNSII
TRKEFQEGLKIFFPGVSEFGKESILFHYTDWVDDQRPENYREALGDVVGDYNFICPAL
EFTKKFSEWGNNAFFYYFEHRSSKLPWPEWMGVMHGYEIEFVFGLPLERRDNYTKA
EEILSRSIVKRWANFAKYGNPNETQNNSTSWPVFKSTEQKYLTLNTESTRIMTKLRAQ
QCRFWTSFFPKVDAHKSEVAHRFKDLGEENFKALVLIAFAQYLQQCPFEDHVKLVNEVT
EFAKTCVADESAENCDKSLHTLFGDKLCTVATLRETYGEMADCCAKQEPERNECFLQHK
DDNPNLPRLVRPEVDVMCTAFHDNEETFLKKYLYEIARRHPYFYAPELLFFAKRYKAAFTE
CCQAADKAACLLPKLDELRDEGKASSAKQRLKCASLQKFGERAFKAWAVARLSQRFPKAE
FAEVSKLVTDLTKVHTECCHGDLLECADDRADLAKYICENQDSISSKLKECCEKPLLEKSH
CIAEVENDEMPADLPSLAADFVESKDVCKNYAEAKDVFLGMFLYEYARRHPDYSVVLLLRL
AKTYETTLEKCCAAADPHECYAKVFDEFKPLVEEPQNLIKQNCELFEQLGEYKFQNALLV
RYTKKVPQVSTPTLVEVSRNLGKVGSKCCKHPEAKRMPCAEDYLSVVLNQLCVLHEKTPVS
DRVTKCCTESLVNRRPCFSALEVDETYVPKEFNAETFTFHADICTLSEKERQIKKQTALVEL
VKHKPKATKEQLKAVMDDFAAFVEKCCKADDKETCFAEEGKKLVAASQAALGL

Figure 1

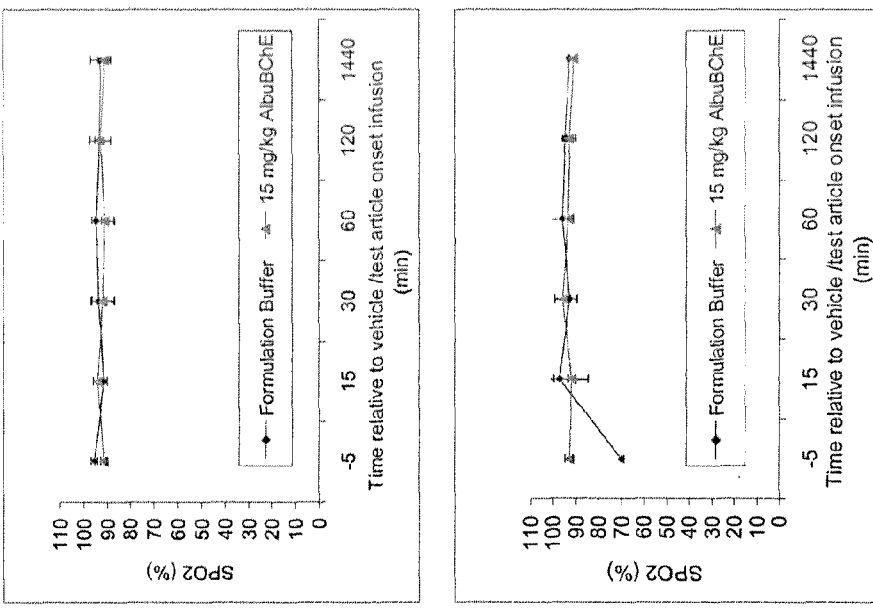
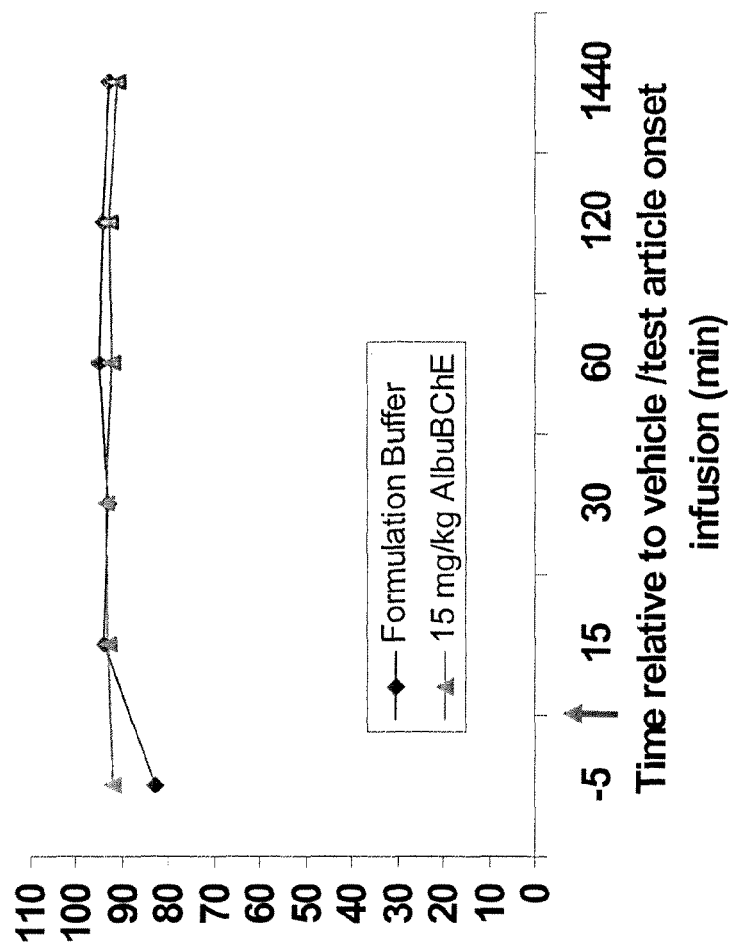
Figure 25A
Figure 25B

| Treatment following addiction phase and forced abstinence | Lever Press (per session) |
|---|---|
| Saline injection | 0 |
| Cocaine injection | 21 |
| Albu-BChE followed by Cocaine | 0 |

Figure 48

|  | AlbuBChE | AlbuBChE | AlbuBChE |
|---|---|---|---|
| Route | SC | IM | IV |
| Dose (mg/kg) | 3 | 3 | 3 |
| Bioavailability (%) | 39% | 79% | 100% |
| Half-life (t1/2) (hr) | 36 | 35 | 28 |
| Tmax (hr) | 24 | 3 | 0.083 |

Figure 49

SEQUENCE LISTING

```
<160> NUMBER OF SEQ ID NOS: 4

<210> SEQ ID NO 1
<211> LENGTH: 529
<212> TYPE: PRT
<213> ORGANISM: Homo sapiens

<400> SEQUENCE: 1

Glu Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
                20                  25                  30

Tyr Ala Gln Pro Pro Leu Gly Arg Leu Arg Phe Lys Lys Pro Gln Ser
            35                  40                  45

Leu Thr Lys Trp Ser Asp Ile Trp Asn Ala Thr Lys Tyr Ala Asn Ser
        50                  55                  60

Cys Cys Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
                100                 105                 110

Ile Tyr Gly Gly Gly Phe Gln Thr Gly Thr Ser Ser Leu His Val Tyr
            115                 120                 125

Asp Gly Lys Phe Leu Ala Arg Val Glu Arg Val Ile Val Val Ser Met
        130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
                180                 185                 190

Thr Leu Phe Gly Glu Ser Ser Gly Ala Ala Ser Val Ser Leu His Leu
            195                 200                 205

Leu Ser Pro Gly Ser His Ser Leu Phe Thr Arg Ala Ile Leu Gln Ser
        210                 215                 220

Gly Ser Phe Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
                260                 265                 270

Leu Leu Asn Glu Ala Phe Val Val Pro Tyr Gly Thr Pro Leu Gly Val
            275                 280                 285

Asn Phe Gly Pro Thr Val Asp Gly Asp Phe Leu Thr Asp Met Pro Asp
        290                 295                 300
```

```
Ile Leu Leu Glu Leu Gly Gln Phe Lys Lys Thr Gln Ile Leu Val Gly
305                 310                 315                 320

Val Asn Lys Asp Glu Gly Thr Trp Phe Leu Val Gly Gly Ala Pro Gly
                325                 330                 335

Phe Ser Lys Asp Asn Asn Ser Ile Ile Thr Arg Lys Glu Phe Gln Glu
            340                 345                 350

Gly Leu Lys Ile Phe Phe Pro Gly Val Ser Glu Phe Gly Lys Glu Ser
            355                 360                 365

Ile Leu Phe His Tyr Thr Asp Trp Val Asp Asp Gln Arg Pro Glu Asn
370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
            420                 425                 430

Trp Met Gly Val Met His Gly Tyr Glu Ile Glu Phe Val Phe Gly Leu
            435                 440                 445

Pro Leu Glu Arg Arg Asp Asn Tyr Thr Lys Ala Glu Glu Ile Leu Ser
    450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser Phe Phe Pro Lys
            515                 520                 525

Val

<210> SEQ ID NO 2
<211> LENGTH: 585
<212> TYPE: PRT
<213> ORGANISM: Homo sapiens

<400> SEQUENCE: 2

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140
```

```
Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560
```

```
Ala Asp Asp Lys Glu Thr Cys Phe Ala Glu Glu Gly Lys Lys Leu Val
            565                 570                 575

Ala Ala Ser Gln Ala Ala Leu Gly Leu
            580                 585

<210> SEQ ID NO 3
<211> LENGTH: 23
<212> TYPE: PRT
<213> ORGANISM: Artificial Sequence
<220> FEATURE:
<223> OTHER INFORMATION: signal peptide

<400> SEQUENCE: 3

Met Arg Pro Thr Trp Ala Trp Trp Leu Phe Leu Val Leu Leu Leu Ala
1               5                   10                  15

Leu Trp Ala Pro Ala Arg Gly
            20

<210> SEQ ID NO 4
<211> LENGTH: 1137
<212> TYPE: PRT
<213> ORGANISM: Artificial Sequence
<220> FEATURE:
<223> OTHER INFORMATION: AlbuBChE

<400> SEQUENCE: 4

Met Arg Pro Thr Trp Ala Trp Trp Leu Phe Leu Val Leu Leu Leu Ala
1               5                   10                  15

Leu Trp Ala Pro Ala Arg Gly Glu Asp Asp Ile Ile Ile Ala Thr Lys
            20                  25                  30

Asn Gly Lys Val Arg Gly Met Asn Leu Thr Val Phe Gly Gly Thr Val
        35                  40                  45

Thr Ala Phe Leu Gly Ile Pro Tyr Ala Gln Pro Pro Leu Gly Arg Leu
    50                  55                  60

Arg Phe Lys Lys Pro Gln Ser Leu Thr Lys Trp Ser Asp Ile Trp Asn
65                  70                  75                  80

Ala Thr Lys Tyr Ala Asn Ser Cys Cys Gln Asn Ile Asp Gln Ser Phe
                85                  90                  95

Pro Gly Phe His Gly Ser Glu Met Trp Asn Pro Asn Thr Asp Leu Ser
            100                 105                 110

Glu Asp Cys Leu Tyr Leu Asn Val Trp Ile Pro Ala Pro Lys Pro Lys
        115                 120                 125

Asn Ala Thr Val Leu Ile Trp Ile Tyr Gly Gly Gly Phe Gln Thr Gly
    130                 135                 140

Thr Ser Ser Leu His Val Tyr Asp Gly Lys Phe Leu Ala Arg Val Glu
145                 150                 155                 160

Arg Val Ile Val Val Ser Met Asn Tyr Arg Val Gly Ala Leu Gly Phe
                165                 170                 175

Leu Ala Leu Pro Gly Asn Pro Glu Ala Pro Gly Asn Met Gly Leu Phe
            180                 185                 190

Asp Gln Gln Leu Ala Leu Gln Trp Val Gln Lys Asn Ile Ala Ala Phe
        195                 200                 205

Gly Gly Asn Pro Lys Ser Val Thr Leu Phe Gly Glu Ser Ser Gly Ala
    210                 215                 220

Ala Ser Val Ser Leu His Leu Leu Ser Pro Gly Ser His Ser Leu Phe
225                 230                 235                 240

Thr Arg Ala Ile Leu Gln Ser Gly Ser Phe Asn Ala Pro Trp Ala Val
                245                 250                 255
```

```
Thr Ser Leu Tyr Glu Ala Arg Asn Arg Thr Leu Asn Leu Ala Lys Leu
            260                 265                 270

Thr Gly Cys Ser Arg Glu Asn Glu Thr Glu Ile Ile Lys Cys Leu Arg
            275                 280                 285

Asn Lys Asp Pro Gln Glu Ile Leu Leu Asn Glu Ala Phe Val Val Pro
            290                 295                 300

Tyr Gly Thr Pro Leu Gly Val Asn Phe Gly Pro Thr Val Asp Gly Asp
305                 310                 315                 320

Phe Leu Thr Asp Met Pro Asp Ile Leu Leu Glu Leu Gly Gln Phe Lys
                325                 330                 335

Lys Thr Gln Ile Leu Val Gly Val Asn Lys Asp Glu Gly Thr Trp Phe
            340                 345                 350

Leu Val Gly Gly Ala Pro Gly Phe Ser Lys Asp Asn Asn Ser Ile Ile
            355                 360                 365

Thr Arg Lys Glu Phe Gln Glu Gly Leu Lys Ile Phe Phe Pro Gly Val
            370                 375                 380

Ser Glu Phe Gly Lys Glu Ser Ile Leu Phe His Tyr Thr Asp Trp Val
385                 390                 395                 400

Asp Asp Gln Arg Pro Glu Asn Tyr Arg Glu Ala Leu Gly Asp Val Val
                405                 410                 415

Gly Asp Tyr Asn Phe Ile Cys Pro Ala Leu Glu Phe Thr Lys Lys Phe
            420                 425                 430

Ser Glu Trp Gly Asn Asn Ala Phe Phe Tyr Tyr Phe Glu His Arg Ser
            435                 440                 445

Ser Lys Leu Pro Trp Pro Glu Trp Met Gly Val Met His Gly Tyr Glu
            450                 455                 460

Ile Glu Phe Val Phe Gly Leu Pro Leu Glu Arg Arg Asp Asn Tyr Thr
465                 470                 475                 480

Lys Ala Glu Glu Ile Leu Ser Arg Ser Ile Val Lys Arg Trp Ala Asn
                485                 490                 495

Phe Ala Lys Tyr Gly Asn Pro Asn Glu Thr Gln Asn Asn Ser Thr Ser
            500                 505                 510

Trp Pro Val Phe Lys Ser Thr Glu Gln Lys Tyr Leu Thr Leu Asn Thr
            515                 520                 525

Glu Ser Thr Arg Ile Met Thr Lys Leu Arg Ala Gln Gln Cys Arg Phe
            530                 535                 540

Trp Thr Ser Phe Phe Pro Lys Val Asp Ala His Lys Ser Glu Val Ala
545                 550                 555                 560

His Arg Phe Lys Asp Leu Gly Glu Glu Asn Phe Lys Ala Leu Val Leu
                565                 570                 575

Ile Ala Phe Ala Gln Tyr Leu Gln Gln Cys Pro Phe Glu Asp His Val
            580                 585                 590

Lys Leu Val Asn Glu Val Thr Glu Phe Ala Lys Thr Cys Val Ala Asp
            595                 600                 605

Glu Ser Ala Glu Asn Cys Asp Lys Ser Leu His Thr Leu Phe Gly Asp
            610                 615                 620

Lys Leu Cys Thr Val Ala Thr Leu Arg Glu Thr Tyr Gly Glu Met Ala
625                 630                 635                 640

Asp Cys Cys Ala Lys Gln Glu Pro Glu Arg Asn Glu Cys Phe Leu Gln
                645                 650                 655

His Lys Asp Asp Asn Pro Asn Leu Pro Arg Leu Val Arg Pro Glu Val
            660                 665                 670

Asp Val Met Cys Thr Ala Phe His Asp Asn Glu Glu Thr Phe Leu Lys
            675                 680                 685
```

```
Lys Tyr Leu Tyr Glu Ile Ala Arg Arg His Pro Tyr Phe Tyr Ala Pro
            690                 695                 700

Glu Leu Leu Phe Phe Ala Lys Arg Tyr Lys Ala Ala Phe Thr Glu Cys
705                 710                 715                 720

Cys Gln Ala Ala Asp Lys Ala Ala Cys Leu Leu Pro Lys Leu Asp Glu
                725                 730                 735

Leu Arg Asp Glu Gly Lys Ala Ser Ser Ala Lys Gln Arg Leu Lys Cys
            740                 745                 750

Ala Ser Leu Gln Lys Phe Gly Glu Arg Ala Phe Lys Ala Trp Ala Val
        755                 760                 765

Ala Arg Leu Ser Gln Arg Phe Pro Lys Ala Glu Phe Ala Glu Val Ser
    770                 775                 780

Lys Leu Val Thr Asp Leu Thr Lys Val His Thr Glu Cys Cys His Gly
785                 790                 795                 800

Asp Leu Leu Glu Cys Ala Asp Asp Arg Ala Asp Leu Ala Lys Tyr Ile
                805                 810                 815

Cys Glu Asn Gln Asp Ser Ile Ser Ser Lys Leu Lys Glu Cys Cys Glu
            820                 825                 830

Lys Pro Leu Leu Glu Lys Ser His Cys Ile Ala Glu Val Glu Asn Asp
        835                 840                 845

Glu Met Pro Ala Asp Leu Pro Ser Leu Ala Ala Asp Phe Val Glu Ser
    850                 855                 860

Lys Asp Val Cys Lys Asn Tyr Ala Glu Ala Lys Asp Val Phe Leu Gly
865                 870                 875                 880

Met Phe Leu Tyr Glu Tyr Ala Arg Arg His Pro Asp Tyr Ser Val Val
                885                 890                 895

Leu Leu Leu Arg Leu Ala Lys Thr Tyr Glu Thr Thr Leu Glu Lys Cys
            900                 905                 910

Cys Ala Ala Ala Asp Pro His Glu Cys Tyr Ala Lys Val Phe Asp Glu
        915                 920                 925

Phe Lys Pro Leu Val Glu Glu Pro Gln Asn Leu Ile Lys Gln Asn Cys
    930                 935                 940

Glu Leu Phe Glu Gln Leu Gly Glu Tyr Lys Phe Gln Asn Ala Leu Leu
945                 950                 955                 960

Val Arg Tyr Thr Lys Lys Val Pro Gln Val Ser Thr Pro Thr Leu Val
                965                 970                 975

Glu Val Ser Arg Asn Leu Gly Lys Val Gly Ser Lys Cys Cys Lys His
            980                 985                 990

Pro Glu Ala Lys Arg Met Pro Cys Ala Glu Asp Tyr Leu Ser Val Val
        995                 1000                1005

Leu Asn Gln Leu Cys Val Leu His Glu Lys Thr Pro Val Ser Asp
    1010                1015                1020

Arg Val Thr Lys Cys Cys Thr Glu Ser Leu Val Asn Arg Arg Pro
    1025                1030                1035

Cys Phe Ser Ala Leu Glu Val Asp Glu Thr Tyr Val Pro Lys Glu
    1040                1045                1050

Phe Asn Ala Glu Thr Phe Thr Phe His Ala Asp Ile Cys Thr Leu
    1055                1060                1065

Ser Glu Lys Glu Arg Gln Ile Lys Lys Gln Thr Ala Leu Val Glu
    1070                1075                1080

Leu Val Lys His Lys Pro Lys Ala Thr Lys Glu Gln Leu Lys Ala
    1085                1090                1095

Val Met Asp Asp Phe Ala Ala Phe Val Glu Lys Cys Cys Lys Ala
    1100                1105                1110
```

-continued

```
Asp Asp Lys Glu Thr Cys Phe Ala Glu Glu Gly Lys Lys Leu Val
    1115            1120             1125

Ala Ala Ser Gln Ala Ala Leu Gly Leu
    1130            1135
```

BCHE ALBUMIN FUSIONS FOR THE TREATMENT OF COCAINE ABUSE

This application claims the benefit of U.S. Provisional Application Nos. 61/283,791, filed Dec. 8, 2009 and 61/412,205, filed Nov. 10, 2010, the contents of which are hereby incorporated by reference in their entirety.

Throughout this application various publications, published patent applications, and patents are referenced. The disclosures of these documents in their entireties are hereby incorporated by reference into this application in order to more fully describe the state of the art to which this invention pertains.

BACKGROUND

Cocaine abuse and dependence have disastrous medical and social consequences which have made the development of an effective treatment a high priority (Pan, Y., Gao, D., Yang, W., Cho, H., Yahg, G., Tai, H., Zhan, C., "Computational redesign of human butyrylcholinesterase for anticocaine medication," *PNAS*, 102(46):16656-61, 2005). However, as stated by Brimijoin et al.: "there is no reliable means to treat cocaine overdose or reduce the likelihood of relapse in users who have achieved abstinence. Human plasma butyrylcholinesterase (BChE) contributes to normal cocaine metabolism and has been considered for use in treating cocaine toxicity" (Brimijoin, S., Gao, Y., Anker, J., Gliddon, L., LaFleur, D., Shah, R., Zhao, Q., Singh, M., Carroll, M., "A Cocaine Hydrolase Engineered from Human Butyrylcholinesterase Selectively Blocks Cocaine Toxicity and Reinstatement of Drug Seeking in Rats," *Neuropsychopharmacology*, 33:2715-25, 2008).

Wild-type BChE, while important for cocaine metabolism in the body, has low catalytic efficiency with cocaine. The low cocaine hydrolase activity of wild-type BChE would require the use of prohibitively large quantities of purified enzyme for treatment of cocaine abuse or overdose. Mutagenesis performed on human BChE with the goal of enhancing the cocaine hydrolase activity resulted in the development of the double mutant A328W/Y332A (residues 356 and 360 relative to full length BChE) that has a $k_{cat}$ that is 40-fold higher than wild-type BChE, with only a slightly increased $K_M$ (Sun H., Shen M., Pang Y., Lockridge O., Brimijoin S., "Cocaine Metabolism Accelerated by a Re-Engineered Human Butyrylcholinesterase" *Journal of Pharmacology and Experimental Therapeutics*, 302(2):710-716, 2002).

Further experimentation utilizing molecular dynamics to simulate the transition state for the first chemical reaction step of BChE catalyzed hydrolysis of cocaine resulted in the BChE mutant A227S/S315G/A356W/Y360G that has a catalytic efficiency which is 500-fold greater than wild-type BChE and is greater than other previously designed BChE mutants (Pan, Y., Gao, D., Yang, W., Cho, H., Yang, G., Tai, H., Zhan, C., "Computational redesign of human butyrylcholinesterase for anticocaine medication," *PNAS*, 102(46):16656-61, 2005).

To obtain a form of the A227S/S315G/A356W/Y360G BChE mutant that may be suitable for therapeutic use, the BChE mutant designed by Pan et al. was fused at its C terminus to human serum albumin (HSA) because it has been observed that similar fusions exhibit favorable pharmacokinetic properties with high stability and extended plasma half lives. It was observed that the BChE-albumin fusion comprising the above mutations retains high catalytic efficiency with cocaine and exhibits a plasma half-life of 8 hours after i.v. injection to rats. (Brimijoin S., Cao, Y., Anker J., Gliddon L., LaFleur D., Shah R., Zhao, Q., "A Cocaine Hydrolase Engineered from Human Butyrylcholinesterase Selectively Blocks Cocaine Toxicity and Reinstatement of Drug Seeking in Rats" *Neuropsychopharmacology*, 33:2715-25, 2008).

To date, there has been no effective method for treating cocaine abuse or overdose in primates developed that utilizes a BChE-albumin fusion comprising the mutations A227S, S315G, A356W, and Y360G.

BRIEF SUMMARY OF THE INVENTION

The subject invention provides a method of attenuating a biological effect of a cocaine exposure in a primate comprising administering to the primate an amount of a fusion protein comprising (a) a mutant butyrylcholinesterase (BChE) polypeptide comprising the sequence
EDDIIIATKNGKVRGMNLTVFG-
GTVTAFLGIPYAQPPLGRLRFKKPQSLT-
KWSDIWNA TKYANSCCQNIDQSEPGFHGSEM-
WNPNTDLSEDCLYLNVWIPAPKPKNATVLIWIY-
GG GFQTGTSSLHVYDGKFLARVERVIVVSM-
NYRVGALGFLALPGNPEAPGNMGLEDQQLA
LQWVQKNIAAFGGNPKSVTLFGESS-
GAASVSLHLLSPGSHSLFTRAILQSGSFNAPWA
VTSLYEARNRTLNLAKLTGCSRENETEI-
IKCLRNKDPQEILLNEAFVVPYGTPLGVNF
GPTVDGDFLTDMPDILLELGQFKKTQIL-
VGVNKDEGTWFLVGGAPGFSKDNNSIITRK
EFQEGLKIFFPGVSEFGKESILFHYTD-
WVDDQRPENYREALGDVVGDYNFICPALEFT
KKFSEWGNNAFFYYEEHRSSKLPWPEW-
MGVMHGYEIEFVFGLPLERRDNYTKAEEILS
RSIVKRWANFAKYGNPNETQNNSTSW-
PVFKSTEQKYLTLNTESTRIMTKLRAQQCRFW
TSFFPKV (SEQ ID NO:1), (b) a human serum albumin (HSA) polypeptide comprising the sequence
DAHKSEVAHRFKDLGEENFKALV-
LIAFAQYLQQCPFEDHVKLVNEVTEFAK-
TCVADES AENCDKSLHTLFGDKLCTVATLRE-
TYGEMADCCAKQEPERNECFLQHKDDNPNLPR-
LV RPEVDVMCTAFHDNEETFLKKYLYEIAR-
RHPYFYAPELLFFAKRYKAAFTECCQAADK
AACLLPKLDELRDEGKASSAKQRLK-
CASLQKFGERAFKAWAVARLSQRFPKAEFAEVS
KLVTDLTKVHTECCHGDLLECADDRAD-
LAKYICENQDSISSKLKECCEKPLLEKSHCI AEV-
ENDEMPADLPSLAADFVESKDVCKNYAE-
AKDVFLGMFLYEYARRHPDYSVVLLLR
LAKTYETTLEKCCAAADPHECYAKVF-
DEFKPLVEEPQNLIKQNCELFEQLGEYKFQNA
LLVRYTKKVPQVSTPTLVEVSRNLGKVG-
SKCCKHPEAKRMPCAEDYLSVVLNQLCVLH
EKTPVSDRVTKCCTESLVNRRPCFSA-
LEVDETYVPKEFNAETFTFHADICTLSEKERQ
IKKQTALVELVKHKPKATKEQLKAVMD-
DFAAFVEKCCKADDKETCEAEEGKKLVAASQ
AALGL (SEQ ID NO:2), and (c) a signal peptide comprising the sequence
MRPTWAWWLFLVLLLALWAPARG (SEQ ID NO:3),
wherein the amount of the fusion protein is effective to cause attenuation of the biological effect of the cocaine exposure in the primate.

DESCRIPTION OF THE FIGURES

FIG. 1 (SEQ ID NO: 4) shows the amino acid sequence of AlbuBChE, a BChE-albumin fusion protein comprising the mutations A227S, S315G, A356W, and Y360G.

FIG. 25A shows mean SPO2 levels vs. time in cynomolgus monkeys prior to and following a single IM administration of 15 mg/kg AlbuBChE dose or formulation buffer. Data for male cynomolgus monkeys is shown in FIG. 25B, top panel, and data for female cynomolgus monkeys is shown in FIG. 25B, bottom panel.

FIG. 48 shows the number of lever presses per session in rats following saline injection, cocaine injection (10 mg/kg, IV), or AlbuBChE (2 mg/kg, IV) followed by cocaine (10 mg/kg, IV) after an addiction phase and forced abstinence.

FIG. 49 shows AlbuBChE bioavailability, half-life, and time for maximum concentration, $T_{max}$, in cynomolgus monkeys following a single intravenous (IV), subcutaneous (SC), or intramuscular (IM) injection. AlbuBChE absolute bioavailability for IM and Sc routes of administration was calculated relative to IV at the 3 mg/kg dose level.

DETAILED DESCRIPTION OF THE INVENTION

Figure 2:
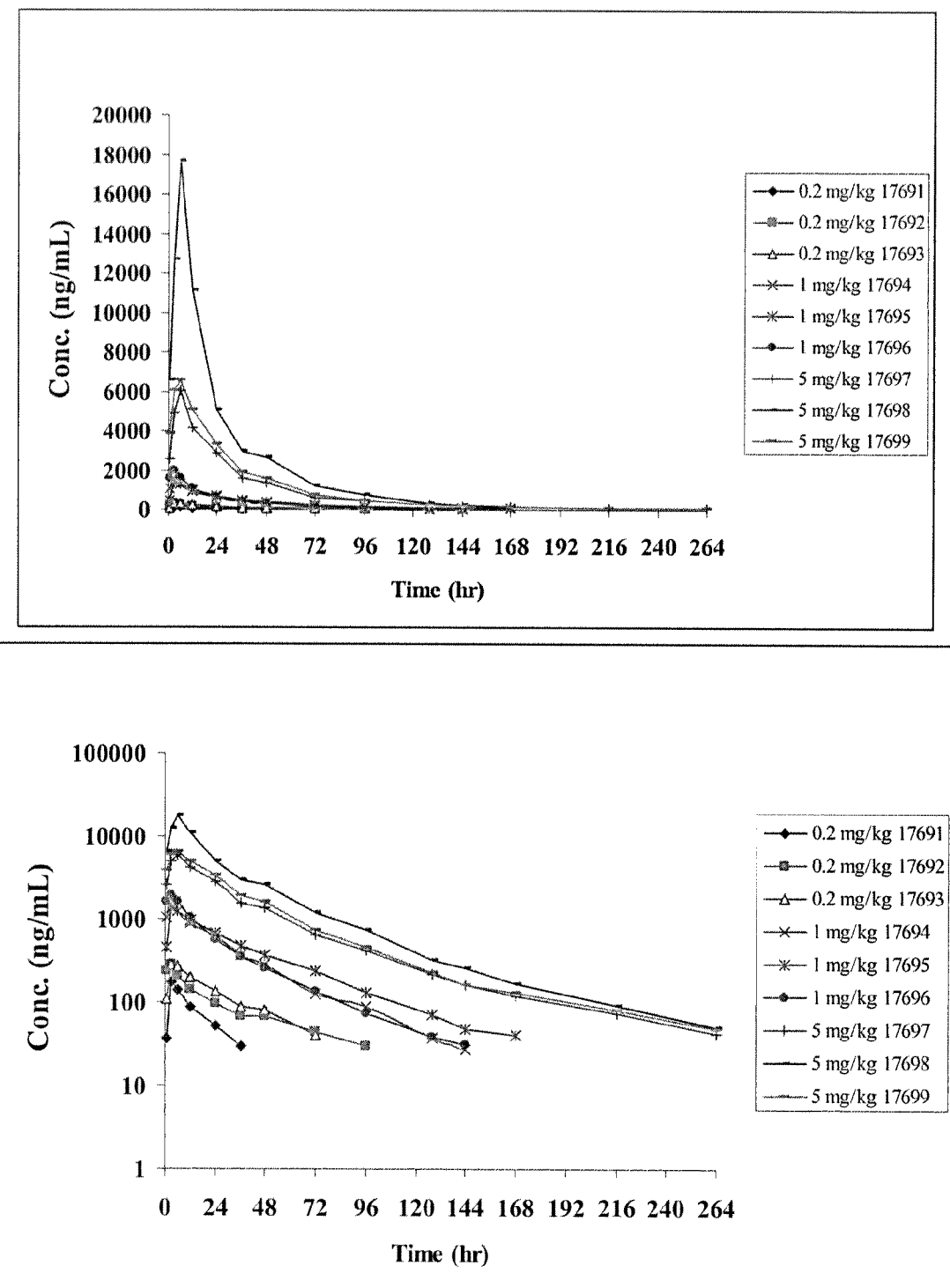
FIG. 2 shows AlbuBChE serum concentration-time profile in individual cynomolgus monkeys following a single IM administration of 0.2, 1 or 5 mg/kg AlbuBChE dose (top panel linear scale, lower panel semi-logarithmic scale).

The subject invention provides a method of attenuating a biological effect of a cocaine exposure in a primate comprising administering to the primate an amount of a fusion protein comprising (a) a mutant butyrylcholinesterase (BChE) polypeptide comprising the sequence
EDDIIIATKNGKVRGMNLTVEGGTV-
TAELGIPYAQPPLGRLRFKKPQSLTKWSDIWNA
TKYANSCCQNIDQSFPGFHGSEMWNPNT-
DLSEDCLYLNVWIPAPKPKNATVLIWIYGG
GFQTGTSSLHVYDGKFLARVERVIVVSM-
NYRVGALGFLALPGNPEAPGNMGLFDQQLA
LQWVQKNIAAFGGNPKSVTLFGESS-
GAASVSLHLLSPGSHSLFTRAILQSGSFNAPWA
VTSLYEARNRTLNLAKLTGCSRENETEI-
IKCLRNKDPQEILLNEAEVVPYGTPLGVNF
GPTVDGDFLTDMPDILLELGQFKKTQIL-
VGVNKDEGTWFLVGGAPGFSKDNNSIITRK
EFQEGLKIFFPGVSEFGKESILFHYTD-
WVDDQRPENYREALGDVVGDYNFICPALEFT
KKESEWGNNAFFYYFEHRSSKLPWPEW-
MGVMHGYEIEFVFGLPLERRDNYTKAEEILS
RSIVKRWANFAKYGNPNETQNNSTSW-
PVFKSTEQKYLTLNTESTRIMTKLRAQQCRFW
TSFFPKV (SEQ ID NO:1), (b) a human serum albumin (HSA) polypeptide comprising the sequence
DAHKSEVAHRFKDLGEENFKALV-
LIAFAQYLQQCPFEDHVKLVNEVTEFAK-
TCVADES AENCDKSLHTLFGDKLCTVATLRE-
TYGEMADCCAKQEPERNECFLQHKDDNPNLPR-
LV RPEVDVMCTAFHDNEETFLKKYLYEIARRH
PYFYAPELLFFAKRYKAAFTECCQAADK AACLL-
PKLDELRDEGKASSAKQRLKCASLQKF-
GERAFKAWAVARLSQRFPKAEFAEVS KLVTDLT-
KVHTECCHGDLLECADDRADLAKYICENQDSI-
SSKLKECCEKPLLEKSHCI AEVENDEMPADLPS-
LAADFVESKDVCKNYAEAKDVFLGMFLY-
EYARRHPDYSVVLLLR LAKTYETTLEKC-
CAAADPHECYAKVFDEFKPLVEEPQNLIKQNCE-
LFEQLGEYKFQNA LLVRYT-
KKVPQVSTPTLVEVSRNLGKVGSKCCKH-
PEAKRMPCAEDYLSVVLNQLCVLH EKTPVS-
DRVTKCCTESLVNRRPCFSALEVDETYVPKEF-
NAETFTFHADICTLSEKERQ IKKQTALVELVKH-
KPKATKEQLKAVMDDFAAFVEKCCKAD-
DKETCFAEEGKKLVAASQ AALGL (SEQ ID NO:2), and (c) a signal peptide comprising the sequence
MRPTWAWWLFLVLLLALWAPARG (SEQ ID NO:3),
wherein the amount of the fusion protein is effective to cause attenuation of the biological effect of the cocaine exposure in the primate.

In an embodiment of the method, fusion protein comprises the sequence
MRPTWAWWLFLVLLLALWAPARGEDDII-
IATKNGKVRGMNLTVFGGTVTAFLGIPYAQ
PPLGRLRFKKPQSLTKWSDIWNATKYAN- SCCQNIDQSFPGFHGSEMWNPNTDLSEDCL
YLNVWIPAPKPKNATVLIWIYGGGFQT-
GTSSLHVYDGKFLARVERVIVVSMNYRVGAL
GFLALPGNPEAPGNMGLFDQQLA-
LQWVQKNIAAFGGNPKSVTLFGESS-
GAASVSLHLL SPGSHSLFTRAILQSGSFNAP-
WAVTSLYEARNRTLNLAKLTGCSRENETEIIKCL
RNK DPQEILLNEAFVVPYGTPLGVNF-
GPTVDGDFLTDMPDILLELGQFKKTQIL-
VGVNKDE GTWFLVGGAPGFSKDNNSI-
ITRKEFQEGLKIFEPGVSEFGKESILFHYTDWV
DDQRPE NYREALGDVVGDYNFICPALEFTKKF-
SEWGNNAFFYYFEHRSSKLPWPEWMGVM-
HGYE IEFVFGLPLERRDNYTKAEEILSR-
SIVKRWANFAKYGNPNETQNNSTSWPVFKSTE
QK YLTLNTESTRIMTKLRAQQCRFWTSFFP-
KVDAHKSEVAHRFKDLGEENFKALVLIAFA
QYLQQCPFEDHVKLVNEVTEFAKTC-
VADESAENCDKSLHTLFGDKLCTVATLRETYGE
MADCCAKQEPERNECFLQHKDDNPNL-
PRLVRPEVDVMCTAFHDNEETFLKKYLYEIAR
RHPYFYAPELLFFAKRYKAAFTEC-
CQAADKAACLLPKLDELRDEGKAS-
SAKQRLKCAS LQKFGERAFKAWAVARLSQRFP-
KAEFAEVSKLVTDLTKVHTECCHGDLLECADD
RADL AKYICENQDSISSKLKECCEKPLLEKSH-
C1AEVENDEMPADLPSLAADFVESKDVCKNYAE-
AKDVFLGMELYEYARRHPDYSVVLLR-
LAKTYETTLEKCCAAADPHECYAKVFDE
FKPLVEEPQNLIKQNCELEEQLGEYK-
FQNALLVRYTKKVPQVSTPTLVEVSRNLGKVG
SKCCKHPEAKRMPCAEDYLSVVLNQLCV-
LHEKTPVSDRVTKCCTESLVNRRPCFSALE
VDETYVPKEFNAETFTEHADICTLSEK-
ERQIKKQTALVELVKHKPKATKEQLKAVMDD
FAAFVEKCCKADDKETCFAEE-
GKKLVAASQAALGL (SEQ ID NO:4).

In another embodiment of the method, the fusion protein is administered prior to the cocaine exposure.

In another embodiment, the fusion protein is administered up to one day prior to the cocaine exposure.

In another embodiment, the fusion protein is administered up to 216 hours prior to the cocaine exposure. The fusion protein may be administered 1, 2, 3, 4, 5, 6, 7, 8, or 9 days prior to the cocaine exposure.

In yet another embodiment of the method, the fusion protein is administered after the cocaine exposure. In a further embodiment, the fusion protein is administered up to six hours following the cocaine exposure. In another embodiment, the fusion protein is administered up to one hour after the cocaine exposure.

In yet another embodiment of the method, the cocaine exposure is a single cocaine exposure.

In yet another embodiment of the method, the cocaine exposure is a recurring cocaine exposure. In a further embodiment of the method, the recurring cocaine exposure is cocaine abuse or cocaine dependence.

In yet another embodiment of the method, the recurring cocaine exposure comprises at least six single cocaine exposures in a twelve month period.

In yet another embodiment of the method, the recurring cocaine exposure comprises at least twenty single cocaine exposures during the primate's lifetime.

In yet another embodiment of the method, the biological effect is caused by cocaine overdose in the primate and the attenuating is treating or preventing the biological effect.

In yet another embodiment of the method, the biological effect is an increase in blood pressure.

In a further embodiment of the method, the duration of the increase in blood pressure is reduced by 60-90%.

In a further embodiment of the method, the duration of the increase in blood pressure is reduced by about 78%.

In yet another embodiment of the method, the biological effect is an increase in heart rate or body temperature. In a further embodiment of the method, the degree of attenuation is 45%-70%. In a further embodiment of the method, the degree of attenuation is 57%.

In yet another embodiment of the method, the biological effect is cocaine seeking behavior in the primate.

In yet another embodiment of the method, the cocaine seeking behavior occurs during a period of cocaine abstinence following the cocaine exposure.

In yet another embodiment of the method, the cocaine seeking behavior follows a relapse.

In yet another embodiment of the method, administration of the fusion protein two hours before the relapse attenuates cocaine seeking behavior by the primate immediately following the relapse.

In yet another embodiment of the method, administration of the fusion protein two hours before the cocaine exposure results in a 50% to 100% reduction in the cocaine seeking behavior by the primate.

In yet another embodiment of the method, attenuation of cocaine seeking behavior is observed up to four days following administration of the fusion protein.

In yet another embodiment of the method, the administration of the fusion protein results in a lowering of total cocaine exposure in the primate than without the administration.

In yet another embodiment of the method, attenuating cocaine seeking behavior results in a period of cocaine abstinence in the primate. In a further embodiment of the method, the period of abstinence is 2 weeks to 3 weeks.

In yet another embodiment of the method, attenuating cocaine seeking behavior results in a larger proportion of days in which the primate is not exposed to cocaine than without the administration.

In yet another embodiment of the method, attenuating cocaine seeking behavior results in a larger number of consecutive days in which the primate is not exposed to cocaine than without the administration.

In yet another embodiment of the method, attenuating cocaine seeking behavior results in a lessening of severity of cocaine dependence or abuse as evaluated by the cocaine selective severity assessment (CSSA) or Diagnostic and Statistical Manual of Mental Disorders IV (DSM-IV).

In yet another embodiment of the method, the effective amount of the fusion protein is an amount which reduces the primate's serum cocaine level to about 0 ng/ml within about 30 minutes of a 1 mg/kg intravenous cocaine dose.

In yet another embodiment of the method, the administration of the fusion protein reduces the primate's serum cocaine level to less than 12% of the serum cocaine level without the administration within about 5 minutes of a 1 mg/kg intravenous cocaine dose.

In yet another embodiment of the method, the administration of the fusion protein reduces the primate's serum cocaine level to 7% of the serum cocaine level without the administration within about 5 minutes of a 1 mg/kg intravenous cocaine dose.

In yet another embodiment of the method, the fusion protein is administered only once, daily, semi-weekly, weekly, bi-weekly, or monthly.

In another embodiment, the fusion protein is administered weekly or twice weekly.

In another embodiment, the fusion protein is administered as a single dose following the cocaine exposure.

In another embodiment, the fusion protein is administered as a single dose following a cocaine overdose.

In yet another embodiment of the method, the fusion protein is administered by intramuscular injection or subcutaneous injection.

In yet another embodiment of the method, the fusion protein is in a formulation buffer comprising 10 mM sodium phosphate, 200 mM mannitol, 60 mM trehalose, and 0.01% (w/v) polysorbate 80, pH 7.2.

In yet another embodiment of the method, the fusion protein is present in the formulation at a concentration of at least 30 mg/ml.

In yet another embodiment of the method, attenuation of the biological effect is observed up to 72 hours after administration of the fusion protein.

In yet another embodiment of the method, the primate is a human.

In a further embodiment of the method, the cocaine exposure is a single cocaine exposure of 10 mg to 60 mg or a recurring cocaine exposure wherein each single cocaine exposure of the recurring cocaine exposure is 10 mg to 60 mg.

In yet another embodiment of the method, the effective amount of the fusion protein is an amount which reduces the human's serum cocaine level to about 0 ng/ml within about 30 minutes of a 40 mg intravenous cocaine dose.

In yet another embodiment of the method, the effective amount of the fusion protein is 0.06 mg/kg to 5 mg/kg. In another embodiment of the method, the effective amount of the fusion protein is 0.06 mg/kg, 0.3 mg/kg, 1.6 mg/kg, or 4.8 mg/kg.

In yet another embodiment of the method, the effective amount of the fusion protein is 50 mg to 300 mg. In another embodiment of the method, the effective amount of the fusion protein is 50 mg, 100 mg, 150 mg, or 300 mg.

An embodiment of the BChE-albumin fusion protein comprising the amino acid substitutions A227S, S315G, A356W, and Y360G is shown in FIG. 1 (SEQ ID NO: 4). The amino acid sequence shown in FIG. 1 comprises a heterologous signal peptide, shown by underlining, a BChE domain comprising amino acids E29 to V529 of human BChE, and human serum albumin (HSA), shown in italics. The amino acid substitutions A227S, S315G, A356W, and Y360G are shown in bold and are underlined in FIG. 1. The numbering of the substitutions is relative to that of full length BChE. The protein encoded by the amino acid sequence of FIG. 1 is referred to as "AlbuBChE" throughout this application.

It is understood that all combinations of the above described embodiments of the invention are within the scope of the invention.

As used herein, "primate" refers to any of an order of mammals that are characterized especially by advanced development of binocular vision, specialization of the appendages for grasping, and enlargement of the cerebral hemispheres and that include humans, apes, monkeys, and related forms.

As used herein, "degree of attenuation" refers to the decrease in a biological effect of cocaine exposure that is observed following administration of a BChE-albumin fusion protein as compared to the biological effect of cocaine exposure observed in the absence of the BChE-albumin fusion protein. The degree of attenuation is calculated by the following formula:

$$\text{degree of attenuation} = \frac{\Delta_{BChE-albumin\ absent} - \Delta_{BChE-albumin\ present}}{\Delta_{BChE-albumin\ absent}}$$

For example, if cocaine exposure raises a baseline temperature of 38° C. to 38.7° C. in the absence of a BChE-albumin fusion protein, and cocaine exposure raises a baseline temperature of 38° C. to 38.3° C. in the presence of a BChE-fusion protein, the degree of attenuation is 57.1% ((0.7° C.−0.3° C.)/0.7° C.).

As used herein, "a single cocaine exposure" refers to one exposure of cocaine isolated from any other exposure of cocaine. "A recurring cocaine exposure" refers to more than one single cocaine exposure. The recurring cocaine exposure may be a regular or an irregular pattern of single cocaine exposures beginning with the second or subsequent single cocaine exposure in the subject. An individual experiencing recurring cocaine exposure may meet the criteria for cocaine dependence or cocaine abuse of the Diagnostic and Statistical Manual of Mental Disorders IV (DSM-IV).

As used herein, the term "total cocaine exposure" refers to the aggregate cocaine exposure during a given time interval. Total cocaine exposure may be measured during or after a period of a treatment designed to attenuate cocaine seeking behavior or other biological effect of cocaine exposure.

As used herein, the term "a period of cocaine abstinence" refers to a period of time following cocaine exposure where the primate does not experience a new cocaine exposure.

As used herein, the term "relapse" refers to a cocaine exposure following a period of cocaine abstinence.

It is understood that where a parameter range is provided, all tenths of integers within that range are provided by the invention. For example, "0.2 mg/kg to 15 mg/kg" includes 0.2 mg/kg, 0.3 mg/kg, 0.4 mg/kg, 0.5 mg/kg etc. up to and including 15.0 mg/kg.

An animal dose may be converted to a human equivalent dose (HED) by using the conversion table found in the publication "Guidance for Industry: Estimating the Maximum Safe Starting Dose in Initial Clinical Trials for Therapeutics in Adult Healthy Volunteers," U.S. Department of Health and Human Services, Food and Drug Administration Center for Drug Evaluation and Research (CDER), July 2005. Doses for cynomolgus monkeys in mg/kg may be converted to an HED in mg/kg by dividing the cynomolgus monkey dose by 3.1. Doses for squirrel monkeys in mg/kg may be converted to an HED in mg/kg by dividing the squirrel monkey dose by 5.3.

LIST OF ABBREVIATIONS

| List of Abreviations | |
|---|---|
| $AUC_{(0-t)}$ | Area under the plasma concentration-time curve from time zero up to time of last detectable concentration (tz) |
| $AUC_{(0-\infty)}$ | Area under the plasma concentration-time curve from time zero to infinity |
| % $AUC_{ex}$ | Percentage of AUC that is due to extrapolation from tz to infinity |
| BChE | butyrycholinesterase |
| BQL | Below Quantitation Limit |
| CL | clearance |
| $C_{max}$ | maximum concentration |
| CocH | cocaine hydrolase |

-continued

| List of Abreviations | |
|---|---|
| ELISA | enzyme linked immunosorbent assay |
| GFR | glomerular filtration rate |
| hr | hour(s) |
| HRP | horseradish peroxidase |
| IM | intramuscular |
| IV | intravenous |
| LLOQ | lower limit of quantitation |
| min | minute(s) |
| NCA | noncompartmental analysis |
| NIDA | National Institute on Drug Abuse |
| PBS | phosphate buffered saline |
| PD | pharmacodynamics |
| PK | pharmacokinetics |
| RT | room temperature |
| Rsq | Coefficient of determination |
| % RSD | Percent Relative Standard Deviation |
| SD | Standard Deviation |
| SC | subcutaneous |
| SOP | standard operating protocol |
| $t_{1/2}$ | half-life of the terminal phase |
| $t_{max}$ | time of maximum concentration |
| $V_z$ | volume of distribution from the terminal phase |

The BChE-albumin fusion protein shown in FIG. 1 (AlbuBChE) was applied to trials as described in the examples below.

EXAMPLE 1

A Pharmacokinetic and Pharmacodynamic Study Following a Single Intramuscular Administration of AlbuBChE and Multiple Intravenous Doses of Cocaine to Cynomolgus Monkeys Objectives The objective of this trial was to determine the pharmacokinetic (PK) profile of AlbuBChE in male cynomolgus monkeys following a single intramuscular administration at 0.2, 1 or 5 mg/kg AlbuBChE dose levels and to determine AlbuBChE activity as a function of time by intravenous administration of 1 mg/kg dose of cocaine at 2, 48, 96, 120, and 240 hours after AlbuBChE dose administration.

Rationale

AlbuBChE is a fusion protein of human serum albumin (HSA) and a genetically modified form of human butyrylcholinesterase (BChE) that exhibits high catalytic efficiency for the hydrolysis of cocaine to benzoic acid. AlbuBChE is under development as a potential intervention in preventing relapse to drug-seeking behavior. Fusion of a protein to albumin has been shown to improve the pharmacokinetic properties of the protein by reducing the clearance and extending the half-life. A longer half-life is expected to translate into a longer dosing interval and better compliance with a drug regimen.

Rationale for Species Selection

Cynomolgus monkeys (*macaca mulatta*) were selected for this study based on anatomical, physiological, and biochemical similarities to humans, which may facilitate extrapolation of observed pharmacokinetic and pharmacodynamic properties to humans. Monkeys are known to express butyrylcholinesterase, which is a component of this drug. Monkeys are also physiologically responsive to cocaine.

Rationale for Dose Level and Route

In a previous study, AlbuBChE pharmacokinetic profile was evaluated in cynomolgus monkeys. In that study, the test article was administered SC (7.8, 2.4 and 0.78 mg/kg), IM (2.4 mg/kg) and IV (2.4 mg/kg). The pharmacokinetic properties of AlbuBChE were linear throughout the SC doses measured. The choice of IM for this study was based on the greater bioavailability in IM as compared to SC (79% and 35-39% respectively) observed in the previous study. In addition, AlbuBChE IM dose levels of 0.2, 1 and 5 mg/kg were selected to define AlbuBChE pharmacodynamic range in cynomolgus monkeys.

The dose of cocaine at 1 mg/kg IV was selected as a dose sufficiently high to yield a physiologically relevant response and achieve measurable concentration of cocaine in blood, while not excessively stimulating the animals.

The number of animals in each group is the minimum number of animals per group necessary for assessment of inter animal variability. As this is a pilot study, only one sex (males) was evaluated.

Test Solutions

The test article, AlbuBChE, was stored in a stock solution as a frozen liquid formulation containing 29.9 mg/mL at −70±15° C. Prior to dosing, the test article formulation was thawed at room temperature. When the test article formulation was completely thawed, the container was mixed by gentle inversion and diluted with the appropriate volume of test article diluent to achieve a concentration of 20 mg/mL. This formulation was serially diluted with the test article diluent to achieve concentrations of 4 and 0.8 mg/mL.

Cocaine hydrochloride, the pharmacodynamic test article, was purchased from Sigma. Dose levels were expressed as the hydrochloride salt.

Experimental Design

The study included a total of 11 naïve, adult male cynomolgus monkeys divided into four dose groups:

a control group of two cynomologus monkeys that only received a single IV dose of cocaine;

three dose groups that were treated with a single IM dose of AlbuBChE at 0.2, 1 or 5 mg/kg. Three naïve, adult male cynomolgus monkeys were used in each dose group. Following AlbuBChE treatment, a 1 mg/kg IV dose of cocaine was administered at 2, 48, 96, 120, and 240 hours after AlbuBChE dose administration.

A summary of the dose designation and dose levels can be found in Table 1. Individual doses were calculated based on body weights recorded on the day of dose administration. Animals were not fasted prior to dose administration.

TABLE 1

Group Designations and Dose Levels

| Group | Treatment | AlbuBChE Dose Level (mg/kg) | Dose Concentration (mg/mL) | Dose Volume (mL/kg) | Number of Animals |
|---|---|---|---|---|---|
| 1 | Single IV dose of Cocaine | 1 | 1.0 | 1 | 2 |
| 2 | Single IM dose of AlbuBChE | 0.2 | 0.8 | 0.25 | 3 |
| | Single IV dose of Cocaine at 2, 48, 96, 120, and 240 hours after AlbuBChE dose administration[1] | 1 | 1.0 | 1 | |

TABLE 1-continued

Group Designations and Dose Levels

| Group | Treatment | AlbuBChE Dose Level (mg/kg) | Dose Concentration (mg/mL) | Dose Volume (mL/kg) | Number of Animals |
|---|---|---|---|---|---|
| 3 | Single IM dose of AlbuBChE | 1 | 4 | 0.25 | 3 |
|   | Single IV dose of Cocaine at 2, 48, 96, 120, and 240 hours after AlbuBChE dose administration[1] | 1 | 1.0 | 1 | |
| 4 | Single IM dose of AlbuBChE | 5 | 20 | 0.25 | 3 |
|   | Single IV dose of Cocaine at 2, 48, 96, 120, and 240 hours after AlbuBChE dose administration[1] | 1 | 1.0 | 1 | |

[1]All times will be within ±5 minutes of the listed times

Samples Collection for AlbuBChE

A single intramuscular (IM) administration of AlbuBChE was administered on study day 1 and blood was collected at the time points outlined in Table 2. Approximately 0.5 mL of whole blood was collected from the femoral vein into serum separate tubes (SST).

TABLE 2

Pharmacokinetics for AlbuBChE

| Time Point | Sample Volume | Collection Device |
|---|---|---|
| Pre-dose, 1, 3, 6, 12, 24, 36, 48, 72, 96, 128, 144, 168, 216, and 264 hours post dose | ~0.5 mL | SST |

Samples Collection for Cocaine

Approximately 0.5 mL of whole blood was collected from the femoral vein at 5, 10, 15, 20, 30, 40 and 60 minutes following each dose of cocaine (Study Day 1 of the control group and Study Day 1 (2 hr), 3 (48 hr), 5 (96 hr), 6 (120 hr), and 11 (240 hr) post-AlbuBChE dose administration). Blood was placed into K2EDTA blood collection tubes with esterase inhibitor diisopropylfluorophosphate (DFP). Tubes were inverted several times and placed on wet ice upon collection. Samples were centrifuged at 2-8° C. within 45 minutes of collection. The resultant plasma was recovered and a single 200 µL aliquot of plasma was placed into polypropylene tubes. Plasma samples were frozen over dry ice and stored at −75±15° C.

Assay Methods

The following outline describes the ELISA-based assay employed in the measurement of AlbuBChE concentrations in monkey serum samples obtained pre-administration and at different times after administration.

Immulon 4 HBX plates are coated with 100 µL of anti-BChE mAb 002-01 (Abeam ab17246) at 1 ug/mL in PBS, overnight at 4° C. Blocking is done with 2% Casein in 1×PBS, 200 µL/well, 2 hours at room temperature. After washing, 100 µL of diluted serum samples are added to the plates along with standards. Standards are generated through 3.64 fold, serial dilution of AlbuBChE from 2000 to 3.1 ng/mL. Serum samples and standards are maintained at 10% serum by dilution with buffer containing pooled cynomolgus monkey serum. A wash step precedes detection with 100 µL of anti-HSA mAb-6502-HRP at 0.04 µg/mL for 1 hour. Wells are washed again, prior to developing with 100 µl of TMB substrate. After 15 minutes, the reaction is terminated with 100 µL/well of 1N H2SO4 and read on SpectraMax plate reader at 450/570 nm. Values for unknown serum samples are calculated by interpolation of standard curve generated by 4-parameter fit of AlbuBChE standards. The limit of quantitation in cynomolgus serum was 21.1 ng/mL.

LC-MS Quantitation of Cocaine in Serum

The following outline describes the LC-MS-based assay employed for the measurement of cocaine in plasma samples. Prior to MS analysis, plasma samples, calibration standards and controls were extracted using supported liquid extraction (SLE-ISOLUTE, Biotage). Twenty-five microliters of samples (25 µL) received 150 µl of 5% Ammonium hydroxide and 25 µl internal standard solution (Cocaine-d3). After mixing and transfer to SLE plate, samples were eluted with methylene chloride and evaporated to dryness. After resuspension in 50 µl of reconstitution solution—5% ACM in 10 mM ammonium acetate in water, 10 µl was injected onto Thermo Hypercarb column at 0.5 ml/min. Mobile phase was biphasic. Mass spectrophotometric detection was performed using Api 4000, APCI positive interface and Multiple Reaction Monitoring (MRM). Plasma concentrations of cocaine, benzoylecgonine and ecgonine methyl ester were determined using this assay.

PK Analysis of AlbuBChE

AlbuBChE pharmacokinetic parameter values were determined using serum concentration-time profiles for individual animals. The computer software WinNonlin Professional (Version 4.0.1 Pharsight Corporation, USA) was used. Specifically the model for non-compartmental analysis with extravascular input was applied. If there were fewer than 3 data points in the terminal phase of the serum concentration curve, a terminal phase half-life and PK parameters derived from the half-life were not calculated for that profile. Parameters analyzed include $t_{max}$, $C_{max}$, $t_{1/2}$, $AUC_{(0-t)}$ and $AUC_{(0-\infty)}$ were calculated.

PK Analysis of Cocaine

When the data permits, pharmacokinetic parameter values for cocaine and its metabolites were determined using plasma concentration-times profiles for individual animals at all the study days of cocaine administration. The computer software WinNonlin Professional (Version 4.0.1 Pharsight Corporation, USA) was used. Specifically the model for non-compartmental analysis with IV bolus input for cocaine and extravascular input for the metabolites. If there were fewer than 3 data points in the terminal phase of the plasma concentration curve, a terminal phase half-life and PK parameters derived from the half-life were not calculated for that profile.

PK/PD Analysis

AlbuBChE PK/PD relationship was defined using the computer software WinNonlin Professional (Version 4.0.1 Pharsight Corporation, USA). Specifically the direct sigmoidal inhibitory Effect $E_{max}$ model was use in which maximum effect ($E_{max}$) as measured by cocaine AUC was assumed at AlbuBChE concentration of zero. The model equation can be described as follows:

Inhibitory Effect Sigmoid $E$max, $C=0$ at $E_{max}$, $C=$infinity at $E_o$ $$E=E\text{max}-(E\text{max}-E0)*(C\text{Gamma}/(C\text{Gamma}+EC50**\text{Gamma}))$$

The sigmoidal model was selected due to the higher activity observed at the 48 hr timepoint compared to the 2 hr timepoint.

The PD parameter used in the analysis was cocaine AUC. PK parameters used in the model were AlbuBChE plasma concentrations at 2, 48, 96, 120, and 240 hr post-AlbuBChE dose. Due to the fact that AlbuBChE concentration was not measured at 2 hr post-AlbuBChE dose, the concentration at 3 hr postdose was used in the analysis with the assumptions that AlbuBChE concentration at 3 hr post AlbuBChE dose may reflect AlbuBChE conc. at 2 hr post AlbuBChE dose.

Statistical Methods

Summary statistics of the concentration profiles and OK parameter values by experimental group were calculated using the descriptive statistics function in WinNonlin. Statistical parameters reported are N, mean, SD and percent coefficient of variation (% CV).

Results

AlbuBChE Concentration Profile

Figure 3:
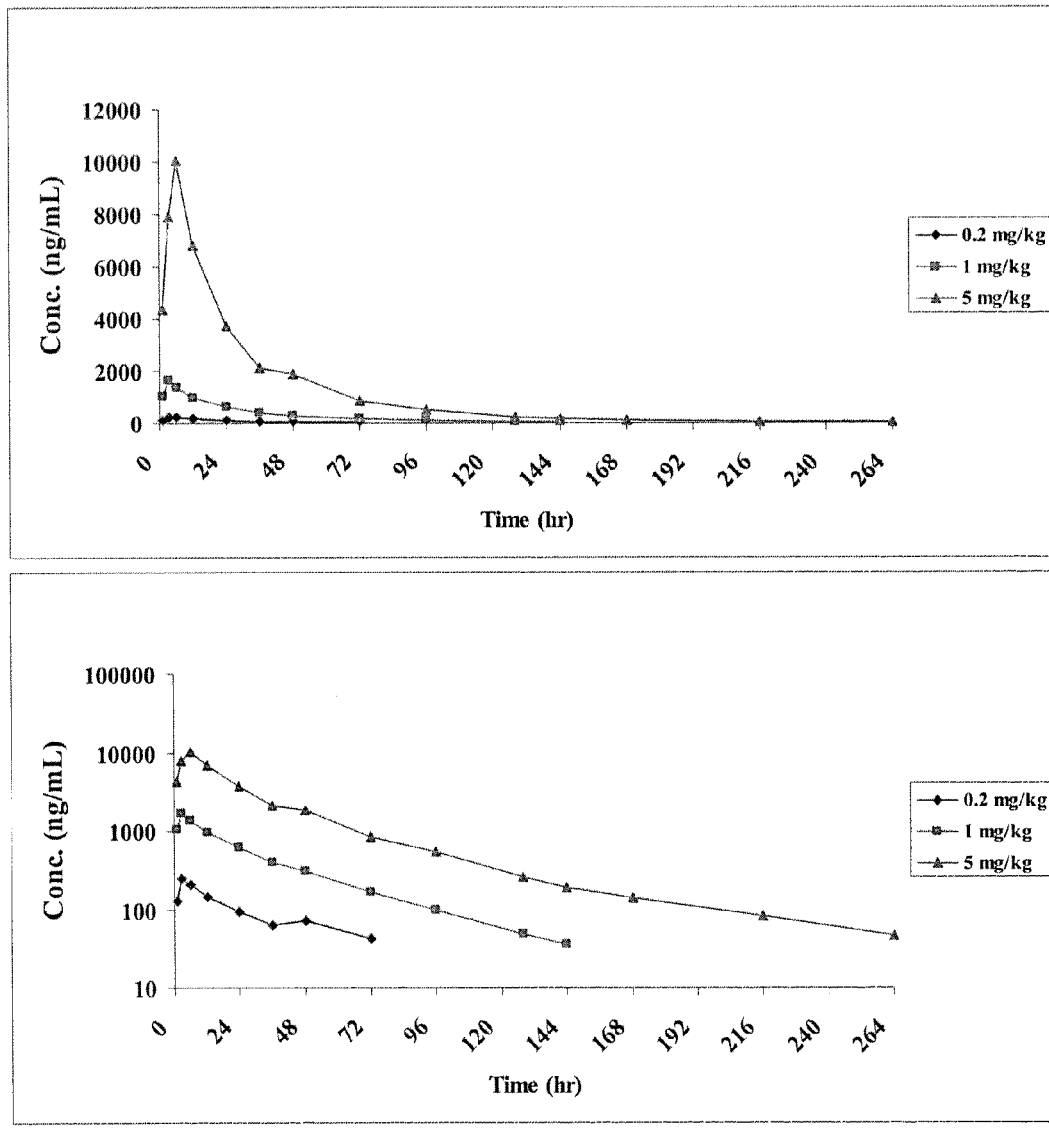
FIG. 3 shows mean AlbuBChE serum concentration-time profile in cynomolgus monkeys following a single IM administration of 0.2, 1 or 5 mg/kg AlbuBChE dose (top panel linear scale, lower panel semi-logarithmic scale).

AlbuBChE concentration-time data and summary statistics are listed in Tables 3 and 4. Individual animal AlbuBChE serum concentration-time profiles following a single AlbuBChE IM injection of 0.2, 1 or 5 mg/kg are shown in FIG. 2. Mean serum concentration-time profiles for the three AlbuBChE dose groups are shown in FIG. 3.

Following IM injection, all animals had measurable AlbuBChE concentrations. Inter-animals variability per dose group appears to be reasonable as indicated by % CV that ranged from 8.2 to 78.4 for all time points. AlbuBChE serum concentration increased with increasing dose.

TABLE 3

Individual and Mean AlbuBChE Serum Concentration (ng/mL) vs. time (hr) Profile in Cynomolgus Monkeys following a single IM administration of 0.2, 1 or 5 mg/kg/animal AlbuBChE dose.

| Time | AlbuBChE Dose: 0.2 mg/kg IM | | | Mean | | |
|---|---|---|---|---|---|---|
| (hr) | 17691 | 17692 | 17693 | (ng/mL) | SD | % CV |
| 0 | <LLOQ | <LLOQ | <LLOQ | <LLOQ | — | — |
| 1 | 37.1 | 235.4 | 111.0 | 128 | 100 | 78.4 |
| 3 | 176.1 | 278.5 | 280.7 | 245 | 59.8 | 24.4 |
| 6 | 144.0 | 212.1 | 272.4 | 210 | 64.2 | 30.7 |
| 12 | 88.4 | 143.1 | 197.9 | 143 | 54.8 | 38.3 |
| 24 | 52.3 | 95.2 | 135.7 | 94.4 | 41.7 | 44.2 |
| 36 | 29.8 | 68.3 | 87.4 | 61.8 | 29.3 | 47.4 |
| 48 | <LLOQ | 66.4 | 80.7 | 73.6 | n = 2 | — |
| 72 | <LLOQ | 44.5 | 39.5 | 42.0 | n = 2 | — |
| 96 | <LLOQ | 30.1 | <LLOQ | <LLOQ | — | — |
| 128 | <LLOQ | <LLOQ | <LLOQ | <LLOQ | — | — |
| 144 | <LLOQ | <LLOQ | <LLOQ | <LLOQ | — | — |
| 168 | <LLOQ | <LLOQ | <LLOQ | <LLOQ | — | — |
| 216 | <LLOQ | <LLOQ | <LLOQ | <LLOQ | — | — |
| 264 | <LLOQ | <LLOQ | <LLOQ | <LLOQ | — | — |

TABLE 3-continued

Individual and Mean AlbuBChE Serum Concentration (ng/mL) vs. time (hr) Profile in Cynomolgus Monkeys following a single IM administration of 0.2, 1 or 5 mg/kg/animal AlbuBChE dose.

| Time | AlbuBChE Dose: 1.0 mg/kg IM | | | Mean | | |
|---|---|---|---|---|---|---|
| (hr) | 17694 | 17695 | 17696 | (ng/mL) | SD | % CV |
| 0 | <LLOQ | <LLOQ | <LLOQ | <LLOQ | — | — |
| 1 | 1058.9 | 462.4 | 1598.6 | 1040 | 568 | 54.6 |
| 3 | 1665.5 | 1374.0 | 1956.0 | 1665 | 291.0 | 17.5 |
| 6 | 1269.3 | 1266.3 | 1596.1 | 1377 | 189.6 | 13.8 |
| 12 | 884.3 | 968.1 | 1049.5 | 967 | 82.6 | 8.5 |
| 24 | 630.1 | 673.8 | 572.1 | 625 | 51.0 | 8.2 |
| 36 | 373.4 | 471.7 | 348.2 | 398 | 65.3 | 16.4 |
| 48 | 289.4 | 362.7 | 264.0 | 306 | 51.1 | 16.7 |
| 72 | 122.1 | 235.0 | 133.0 | 163 | 62.3 | 38.1 |
| 96 | 87.0 | 131.7 | 75.3 | 98.0 | 29.8 | 30.4 |
| 128 | 36.2 | 72.0 | 38.1 | 48.8 | 20.1 | 41.3 |
| 144 | 27.4 | 47.7 | 31.5 | 35.5 | 10.7 | 30.2 |
| 168 | <LLOQ | 39.5 | <LLOQ | <LLOQ | — | — |
| 216 | <LLOQ | <LLOQ | <LLOQ | <LLOQ | — | — |
| 264 | <LLOQ | <LLOQ | <LLOQ | <LLOQ | — | — |

| Time | 5.0 mg/kg IM | | | Mean | | |
|---|---|---|---|---|---|---|
| (hr) | 17697 | 17698 | 17699 | (ng/mL) | SD | % CV |
| 0 | <LLOQ | <LLOQ | <LLOQ | <LLOQ | — | — |
| 1 | 2580.0 | 6570.9 | 3821.0 | 4324 | 2042 | 47.2 |
| 3 | 4899.0 | 12683.9 | 6024.0 | 7869 | 4207.6 | 53.5 |
| 6 | 6016.0 | 17686.8 | 6530.3 | 10078 | 6594.7 | 65.4 |
| 12 | 4178.0 | 11105.8 | 5091.0 | 6792 | 3764.0 | 55.4 |
| 24 | 2836.0 | 5034.0 | 3325.0 | 3732 | 1154.1 | 30.9 |
| 36 | 1572.0 | 2929.0 | 1901.0 | 2134 | 707.9 | 33.2 |
| 48 | 1329.7 | 2644.4 | 1604.9 | 1860 | 693.4 | 37.3 |
| 72 | 637.7 | 1190.8 | 723.6 | 851 | 297.7 | 35.0 |
| 96 | 415.1 | 732.6 | 454.7 | 534.1 | 173.0 | 32.4 |
| 128 | 217.2 | 325.9 | 224.3 | 255.8 | 60.8 | 23.8 |
| 144 | 158.4 | 254.7 | 163.3 | 192.1 | 54.2 | 28.2 |
| 168 | 118.9 | 165.5 | 130.4 | 138.3 | 24.3 | 17.6 |
| 216 | 73.7 | 91.6 | 79.4 | 81.6 | 9.14 | 11.2 |
| 264 | 41.9 | 50.9 | 47.2 | 46.7 | 4.52 | 9.69 |

— Not applicable
LLOQ 27.2 ng/ml

TABLE 4

Summary of Mean AlbuBChE Serum Concentration (ng/ml) vs. time (hr) in Cynomolgus Monkeys following a single IM administration of 0.2, 1, or 5 mg/kg/animal AlbuBChE dose.

| Time (hr) | 0.2 mg/kg | 1 mg/kg | 5 mg/kg |
|---|---|---|---|
| 1 | 128 | 1040 | 4324 |
| 3 | 245 | 1665 | 7869 |
| 6 | 210 | 1377 | 10078 |
| 12 | 143 | 967 | 6792 |
| 24 | 94.4 | 625 | 3732 |
| 36 | 61.8 | 398 | 2134 |
| 48 | 73.6 | 306 | 1860 |
| 72 | 42.0 | 163 | 851 |
| 96 | — | 98.0 | 534 |
| 128 | — | 48.8 | 256 |
| 144 | — | 35.5 | 192 |
| 168 | — | — | 138 |
| 216 | — | — | 81.6 |
| 264 | — | — | 46.7 |

— Not applicable
LLOQ 27.2 ng/ml

Concentration Profile of Cocaine, Benzoylecgonine and Ecgonine methyl ester

Figure 4A:
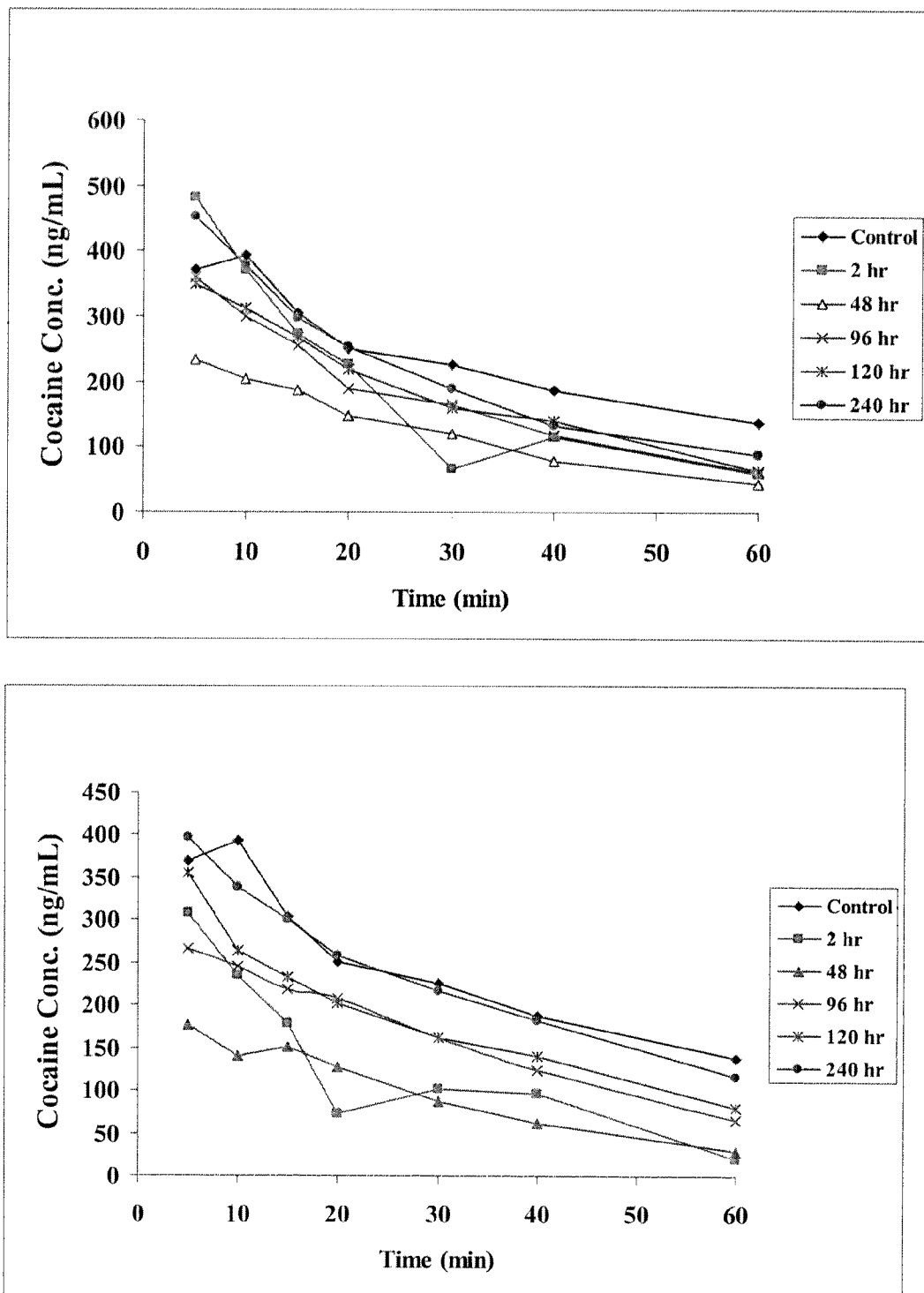
FIG. 4 shows mean cocaine concentration vs. time in control animals (n=2) and as a function of time post-AlbuBChE dose (n=3).
Figure 4B:
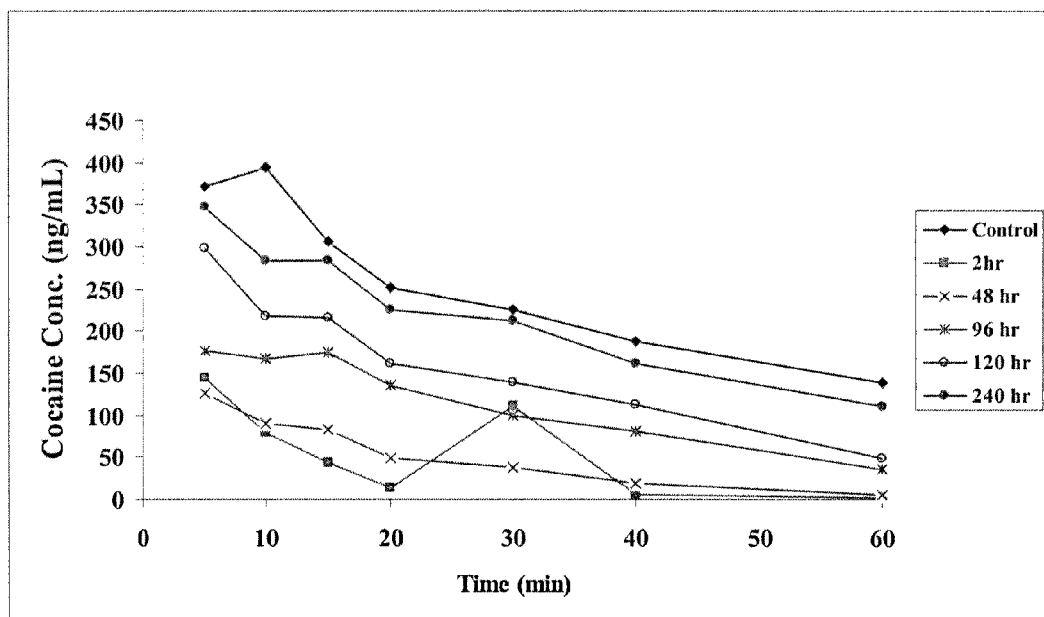

LC/MS analysis was performed on all samples to analyze for cocaine, benzoylecgonine and ecgonine methyl ester levels in monkey plasma. Mean plasma concentration-time profiles in control animals and following 0.2, 1, or 5 mg/kg can be found in Tables 5, 6, and 7 and FIGS. 4, 5 and 6 for cocaine, benzoylecgonine and ecgonine methyl ester, respectively.

Figure 7:
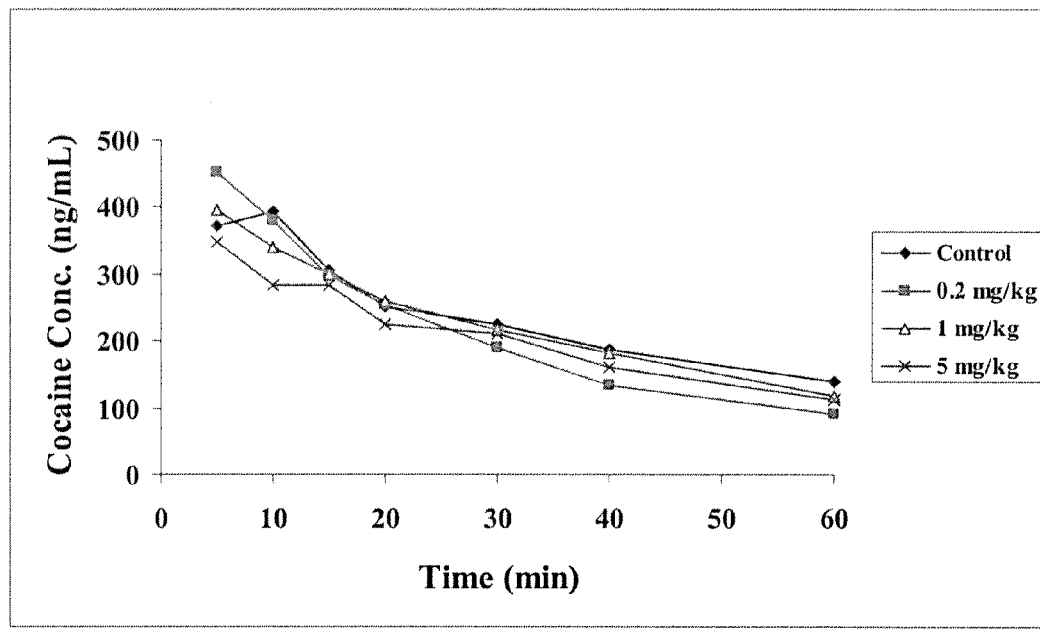
FIG. 7 shows a comparison of mean cocaine concentration-time profile for Day 1 cocaine control group with Day 11 (240 hr) post-AlbuBChE administration at 0.2, 1 or 5 mg/kg.

In general, cocaine plasma concentrations appear to decrease as a function of AlbuBChE dose and increase as a function of time post-AlbuBChE administration. Cocaine concentrations at 240 hr post-AlbuBChE administration appears to be in the same range as Day 1 cocaine control group (FIG. 7). This suggests that AlbuBChE was not active at 240 hr post-AlbuBChE administration of 0.2, 1 or 5 mg/kg. This also indicates that cocaine kinetics do not show time dependent kinetics in cynomolgus monkeys making the comparison of Day 1 single IV dose cocaine control to the multiple dose cocaine profile following AlbuBChE administration feasible.

As one might expect based on cocaine metabolic pathway (FIG. 9), benzoylecgonine plasma concentrations appear to decrease as a function of AlbuBChE dose and increase as a function of time post-AlbuBChE administration.

Figure 9:
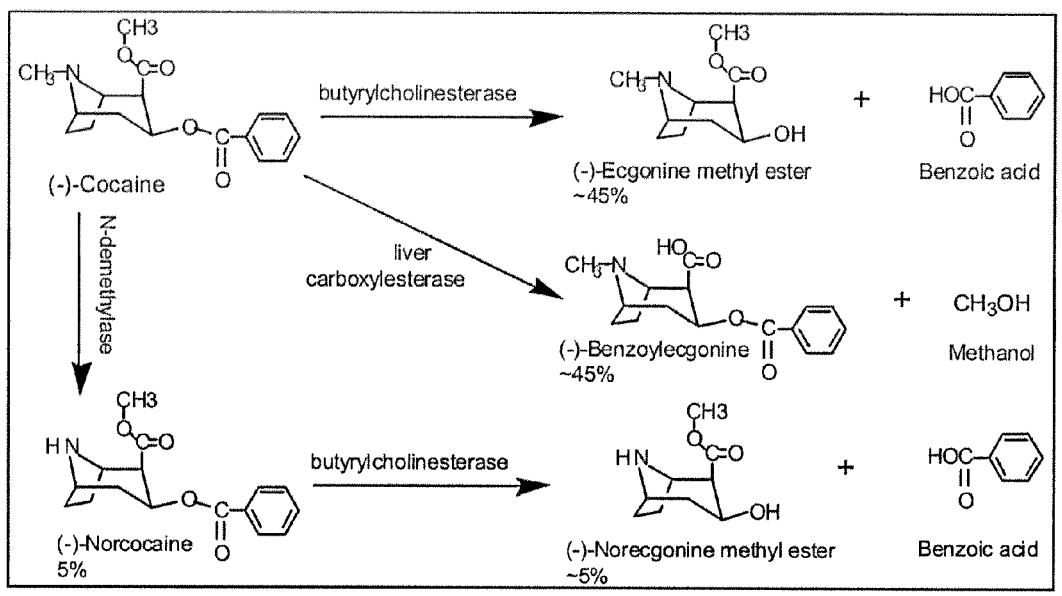
FIG. 9 shows cocaine metabolic pathways.
Figure 10:
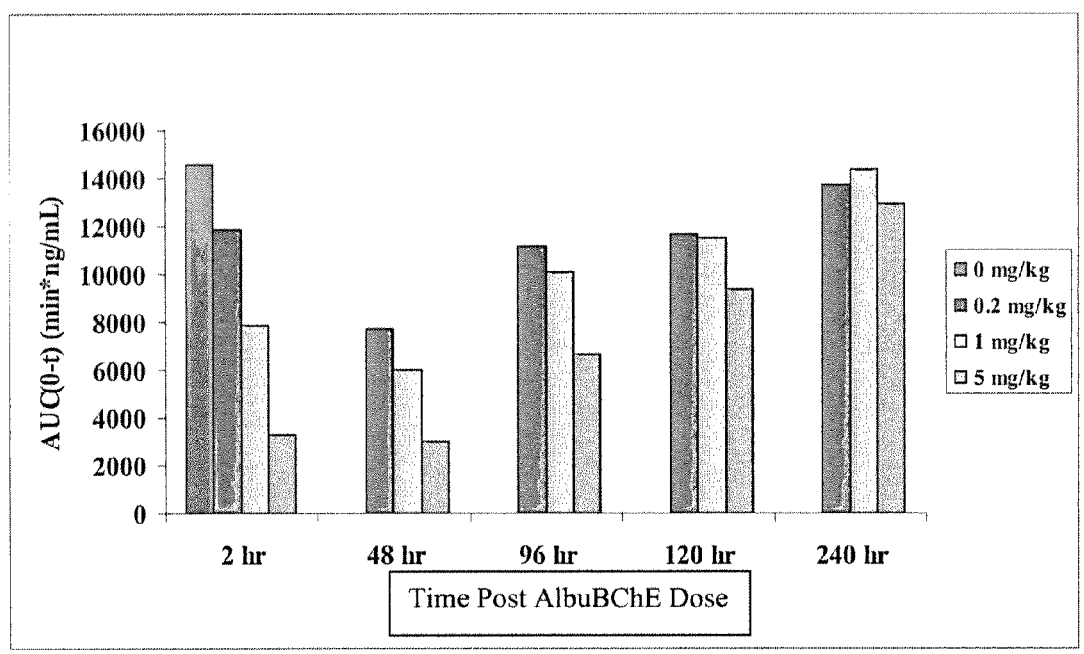
FIG. 10 shows mean cocaine $AUC_{(0-t)}$ following 1 mg/kg IV cocaine dose in control animals (n=2) and as a function of time post-AlbuBChE dose (n=3).

Theoretically, plasma concentration of ecgonine methyl ester should increase following AlbuBChE administration (FIG. 9). This increase was only evident at the cocaine dose administered at 2 hr post-AlbuBChE administration for all three AlbuBChE dose levels. Ecgonine methyl ester plasma concentration could not be easily distinguished from control following cocaine administration at 48, 96, 120 or 240 hr post-AlbuBChE administration.

TABLE 5

Mean Cocaine Plasma Concentration (ng/mL) vs. time (min) in Cynomolgus monkeys following cocaine IV dose of 1 mg/kg in control animals (n = 2) or at 2, 48, 72, 96, 120 and 240 hr post-AlbuBChE IM dose of 0.2, 1, or 5 mg/kg (n = 3 per dose group).

| Time (min) | Control Day 1 | 2 hr | 48 hr | 96 hr | 120 hr | 240 hr |
|---|---|---|---|---|---|---|
| Control and 0.2 mg/kg AlbuBChE Dose | | | | | | |
| 5 | 371 | 481 | 235 | 360 | 349 | 453 |
| 10 | 393 | 370 | 203 | 301 | 312 | 379 |
| 15 | 305 | 273 | 187 | 255 | 267 | 297 |
| 20 | 251 | 227 | 146 | 189 | 218 | 254 |
| 30 | 226 | 67.0 | 121 | 165 | 160 | 189 |
| 40 | 188 | 115 | 77.8 | 118 | 141 | 133 |
| 60 | 138 | 58.6 | 43.2 | 60.5 | 64.7 | 89.5 |

| Time (min) | Control | 2 hr | 48 hr | 96 hr | 120 hr | 240 hr |
|---|---|---|---|---|---|---|
| Control and 1 mg/kg AlbuBChE Dose | | | | | | |
| 5 | 371 | 308 | 176 | 265 | 356 | 397 |
| 10 | 393 | 235 | 140 | 245 | 263 | 340 |
| 15 | 305 | 179 | 152 | 218 | 233 | 300 |
| 20 | 251 | 73.7 | 128 | 208 | 202 | 259 |
| 30 | 226 | 102 | 87.0 | 162 | 161 | 218 |
| 40 | 188 | 96.9 | 62.3 | 123 | 141 | 181 |
| 60 | 138 | 19.7 | 29.1 | 64.8 | 79.7 | 117 |
| Control and 5 mg/kg AlbuBChE Dose | | | | | | |
| 5 | 371 | 145 | 126 | 176 | 298 | 346 |
| 10 | 393 | 77.9 | 89.9 | 166 | 217 | 283 |
| 15 | 305 | 43.5 | 82.7 | 174 | 216 | 283 |
| 20 | 251 | 12.8 | 49.5 | 136 | 161 | 226 |
| 30 | 226 | 110 | 36.7 | 99.0 | 139 | 211 |
| 40 | 188 | 4.96 | 18.9 | 80.6 | 113 | 161 |
| 60 | 138 | 2.26 | 5.74 | 35.2 | 49.5 | 111 |

TABLE 6

Mean Benzoylecgonine Plasma Concentration (ng/mL) vs. time (min) in Cynomolgus monkeys following cocaine IV dose of 1 mg/kg in control animals (n = 2) or at 2, 48, 72, 96, 120 and 240 hr post-AlbuBChE IM dose of 0.2, 1, or 5 mg/kg (n = 3 per dose group).

| Time (min) | Day 1 Control | 2 hr | 48 hr | 96 hr | 120 hr | 240 hr |
|---|---|---|---|---|---|---|
| Control and 0.2 mg/kg AlbuBChE Dose | | | | | | |
| 5 | 47.6 | 50.6 | 27.3 | 49.7 | 55.1 | 53.5 |
| 10 | 65.4 | 49.7 | 29.4 | 47.7 | 46.9 | 53.3 |
| 15 | 63.0 | 50.4 | 29.0 | 52.6 | 53.1 | 62.9 |
| 20 | 72.0 | 65.1 | 28.2 | 55.1 | 55.9 | 63.7 |
| 30 | 82.4 | 28.6 | 37.1 | 56.5 | 64.2 | 69.8 |
| 40 | 87.2 | 58.0 | 36.9 | 55.2 | 61.4 | 74.5 |
| 60 | 96.9 | 60.5 | 35.6 | 57.8 | 66.2 | 80.9 |
| Control and 1 mg/kg AlbuBChE Dose | | | | | | |
| 5 | 47.6 | 30.1 | 24.0 | 43.9 | 37.2 | 40.0 |
| 10 | 65.4 | 33.2 | 23.7 | 41.2 | 38.9 | 47.2 |
| 15 | 63.0 | 32.5 | 24.9 | 40.0 | 42.2 | 55.0 |
| 20 | 72.0 | 32.5 | 26.7 | 43.7 | 40.2 | 56.7 |
| 30 | 82.4 | 28.9 | 29.8 | 47.4 | 51.3 | 64.6 |
| 40 | 87.2 | 38.4 | 29.6 | 46.7 | 50.9 | 68.3 |
| 60 | 96.9 | 29.6 | 29.8 | 49.6 | 54.4 | 75.2 |
| Control and 5 mg/kg AlbuBChE Dose | | | | | | |
| 5 | 47.6 | 22.3 | 20.0 | 44.2 | 44.6 | 44.9 |
| 10 | 65.4 | 23.7 | 21.0 | 43.5 | 47.5 | 56.4 |
| 15 | 63.0 | 22.0 | 24.4 | 49.7 | 50.3 | 71.9 |
| 20 | 72.0 | 22.9 | 23.7 | 51.1 | 57.3 | 83.4 |
| 30 | 82.4 | 31.1 | 25.9 | 56.1 | 63.6 | 88.4 |
| 40 | 87.2 | 21.3 | 25.5 | 57.7 | 69.5 | 101 |
| 60 | 96.9 | 20.1 | 24.4 | 60.5 | 69.2 | 108 |

TABLE 7

Ecgonine Methyl Ester Plasma Concentration (ng/mL) vs. time (min) in Cynomolgus monkeys following cocaine IV dose of 1 mg/kg in control animals (n = 2) or at 2, 48, 72, 96, 120 and 240 hr post-AlbuBChE IM dose of 0.2, 1, or 5 mg/kg (n = 3 per dose group).

| Time (min) | Day 1 Control | 2 hr | 48 hr | 96 hr | 120 hr | 240 hr |
|---|---|---|---|---|---|---|
| Control and 0.2 mg/kg AlbuBChE Dose | | | | | | |
| 5 | 24.4 | 51.6 | 21.1 | 26.4 | 18.9 | 20.1 |
| 10 | 34.5 | 81.9 | 19.5 | 39.4 | 28.9 | 23.1 |
| 15 | 57.4 | 83.2 | 23.9 | 24.5 | 27.6 | 25.1 |
| 20 | 39.0 | 154 | 25.8 | 29.8 | 34.5 | 28.3 |
| 30 | 77.6 | 261 | 33.9 | 49.8 | 136 | 33.9 |
| 40 | 60.8 | 120 | 50.7 | 50.2 | 98 | 38.8 |
| 60 | 80.9 | 120 | 37.0 | 43.4 | 82.9 | 41.4 |
| Control and 1 mg/kg AlbuBChE Dose | | | | | | |
| 5 | 24.4 | 235 | 201 | 138 | 42.7 | 92.7 |
| 10 | 34.5 | 227 | 32.2 | 39.8 | 27.4 | 21.9 |
| 15 | 57.4 | 276 | 48.2 | 42.9 | 37.8 | 25.9 |
| 20 | 39.0 | 301 | 56.2 | 47.3 | 31.8 | 29.5 |
| 30 | 77.6 | 291 | 63.8 | 57.3 | 104 | 41.3 |
| 40 | 60.8 | 202 | 64.9 | 64.4 | 68.6 | 51.8 |
| 60 | 80.9 | 189 | 57.3 | 59.9 | 76.8 | 54.3 |
| Control and 5 mg/kg AlbuBChE Dose | | | | | | |
| 5 | 24.4 | 337 | 119 | 100 | 45.5 | 127 |
| 10 | 34.5 | 321 | 68.9 | 60.9 | 46.0 | 26.1 |
| 15 | 57.4 | 363 | 102 | 82.2 | 96.5 | 30.7 |
| 20 | 39.0 | 331 | 107 | 104 | 60.1 | 35.1 |
| 30 | 77.6 | 266 | 108 | 111 | 79.9 | 49.6 |
| 40 | 60.8 | 308 | 106 | 126 | 122 | 53.1 |
| 60 | 80.9 | 248 | 108 | 127 | 187 | 58.0 |

Pharmacokinetic Analysis of AlbuBChE

AlbuBChE pharmacokinetic parameter values following a single IM dose of 0.2, 1 or 5 mg/kg AlbuBChE dose in individual animals and descriptive statistics per group can be found in Table 8. Mean PK parameter values for AlbuBChE following IM dosing at 0.2, 1 or 5 mg/kg are summarized in Table 9.

In general absorption from IM site of administration was rapid with measurable concentrations observed at the first sample collected (1 hr postdose). Maximum concentration was observed at 3 hr for the 0.2 and 1 mg/kg dose level. $T_{max}$ values was slightly longer (6 hr) for the 5 mg/kg dose.

AlbuBChE exposure increased with increasing dose. Dose normalized $C_{max}$ and ADC values appear to increase as a function of dose suggesting a more than proportional increase in exposure as a function of dose. This was also accompanied with a increase in terminal elimination t½ as a function of dose particularly between 1 and 5 mg/kg dose levels where t½ value almost doubled.

Cocaine pharmacokinetic profile was well characterized for all dose groups and time points with one exception: plasma concentration-time profile for the cocaine dose administered at 2 hr post-AlbuBChE dose was variable for all dose groups. As such, the terminal elimination t½ could not be accurately characterized in most of the animals on this cocaine dosing occasion.

Cocaine $AUC_{(0-t)}$ appears to decrease as a function of AlbuBChE dose and increase as a function of time post-AlbuBChE administration. Similarly, cocaine systemic plasma clearance appears to increase as a function of AlbuBChE dose and return to control values as a function of time post-AlbuBChE dose. At 240 hr post-AlbuBChE administration cocaine AUC and clearance appear to be in the same range as Day 1 cocaine control group.

TABLE 8

Individual and Mean AlbuBChE Pharmacokinetic Parameter Values in Cynomolgus Monkeys following a single IM administration of 0.2, 1 or 5 mg/kg/animal AlbuBChE dose.

| Animal # | $R_{sq}$ | No. Points Lambda-z | t½ (hr) | $T_{max}$ (hr) | $C_{max}$ (ng/mL) | $AUC_{(0-t)}$ (hr * ng/mL) | $AUC_{(0-\infty)}$ (hr * ng/mL) | AUC % Extrap |
|---|---|---|---|---|---|---|---|---|
| *0.2 mg/kg AlbuBChE Dose* | | | | | | | | |
| 17691 | 1.00 | 3 | 15.3 | 3 | 176 | 2746 | 3404 | 19.3 |
| 17692 | 1.00 | 3 | 42.1 | 3 | 279 | 7878 | 9704 | 18.8 |
| 17693 | 0.980 | 7 | 24.4 | 3 | 281 | 8479 | 9867 | 14.1 |
| | | Mean | 27.2 | | 245 | 6368 | 7658 | 17.4 |
| | | SD | 13.6 | | 59.8 | 3151 | 3686 | 2.90 |
| | | % CV | 50.0 | | 24.4 | 49.5 | 48.1 | 16.7 |
| *1 mg/kg AlbuBChE Dose* | | | | | | | | |
| 17694 | 0.990 | 6 | 28.4 | 3 | 1666 | 43128 | 44251 | 2.54 |
| 17695 | 0.992 | 8 | 34.3 | 3 | 1374 | 51298 | 53255 | 3.67 |
| 17696 | 0.992 | 6 | 30.3 | 3 | 1956 | 46185 | 47564 | 2.90 |
| | | Mean | 31.0 | | 1665 | 46871 | 48357 | 3.04 |
| | | SD | 3.03 | | 291 | 4128 | 4554 | 0.581 |
| | | % CV | 9.76 | | 17.5 | 8.81 | 9.42 | 19.1 |
| *5 mg/kg AlbuBChE Dose* | | | | | | | | |
| 17697 | 0.999 | 4 | 63.4 | 6 | 6016 | 201754 | 205584 | 1.86 |
| 17698 | 1.00 | 3 | 56.4 | 6 | 17687 | 437848 | 441992 | 0.938 |
| 17699 | 1.00 | 3 | 65.5 | 6 | 6530 | 235983 | 240442 | 1.85 |
| | | Mean | 61.8 | | 10078 | 291862 | 296006 | 1.55 |
| | | SD | 4.73 | | 6595 | 127581 | 127623 | 0.532 |
| | | % CV | 7.66 | | 65.4 | 43.7 | 43.1 | 34.3 |

TABLE 9

Mean Pharmacokinetic parameter values for AlbuBChE following a single IM injection in cynomolgus monkeys at 0.2, 1 or 5 mg/kg.

| | AlbuBChE Dose | | |
|---|---|---|---|
| | 0.2 mg/kg IM | 1.0 mg/kg IM | 5.0 mg/kg IM |
| t½ (hr) | 27.2 | 31.0 | 61.8 |
| $t_{max}$ (hr) | 3 | 3 | 6 |
| $C_{max}$ (ng/mL) | 245 | 1665 | 10078 |
| $AUC_{(0-t)}$ (hr*ng/mL) | 6368 | 46871 | 291862 |
| $AUC_{(0-\infty)}$ (hr*ng/mL) | 7658 | 48357 | 296006 |
| AUC % Extrap | 17.4 | 3.04 | 1.55 |
| Dose Normalized $C_{max}$ | 1226 | 1665 | 2016 |
| Dose Normalized $AUC_{(0-\infty)}$ | 38292 | 48357 | 59201 |

Pharmacokinetic Analysis of Cocaine and Metabolites

Summary table of mean cocaine pharmacokinetic values per dose group are presented in Table 10.

For all three AlbuBChE dose levels, maximum AlbuBChE effect on cocaine clearance or AUC was observed at 48 hr postdose. The duration of effect was related to AlbuBChE dose levels. Following the 5 mg/kg dose, AlbuBChE effect on cocaine AUC and clearance was evident up to 120 hr postdose. At the 1 mg/kg dose, AlbuBChE effect on cocaine AUC or clearance may still be evident at 96 to 120 hr post-AlbuBChE dose relative to control or the 240 hr values. As AlbuBChE dose decreased to 0.2 mg/kg, so did the duration of effect with 48 hr being the last time point with elevated cocaine clearance. Based on this data, a once or twice weekly dosing regimen of AlbuBChE is likely.

Figure 5A:
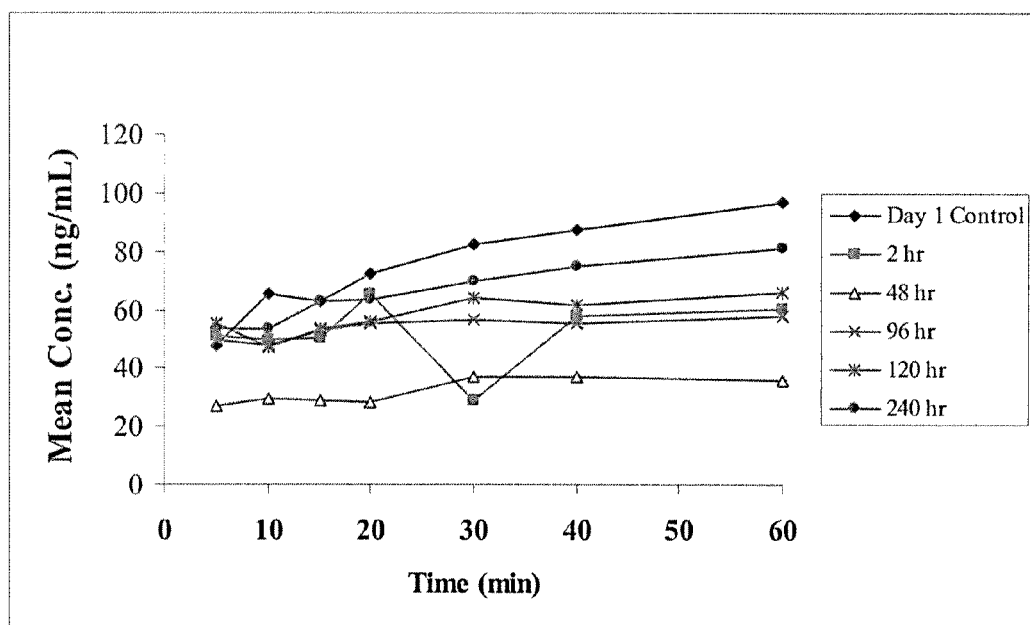
FIG. 5 shows mean benzoylecgonine concentration vs. time in control animals (n=2) and as a function of time post-AlbuBChE dose (n=3).
Figure 5B:
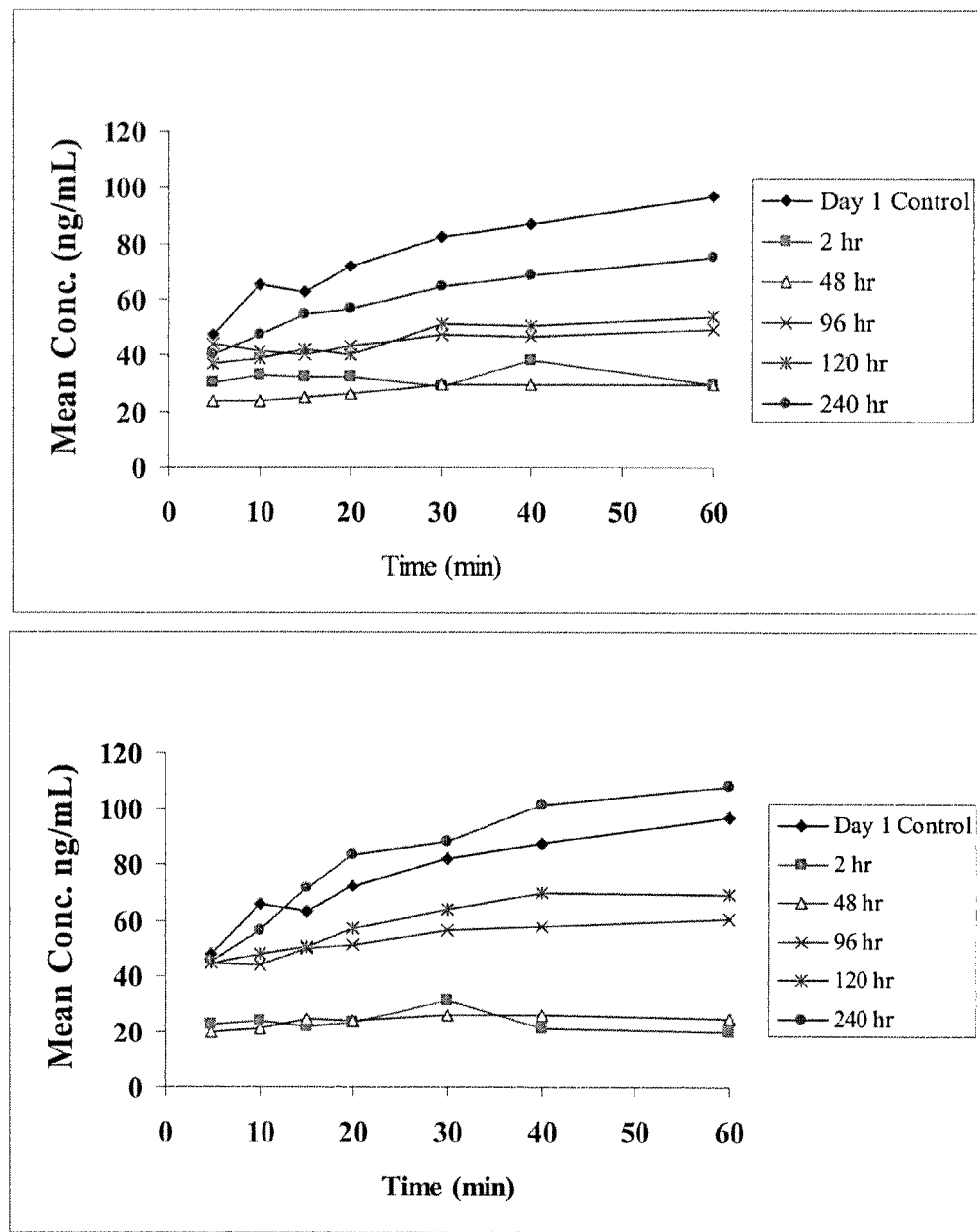
Figure 11:
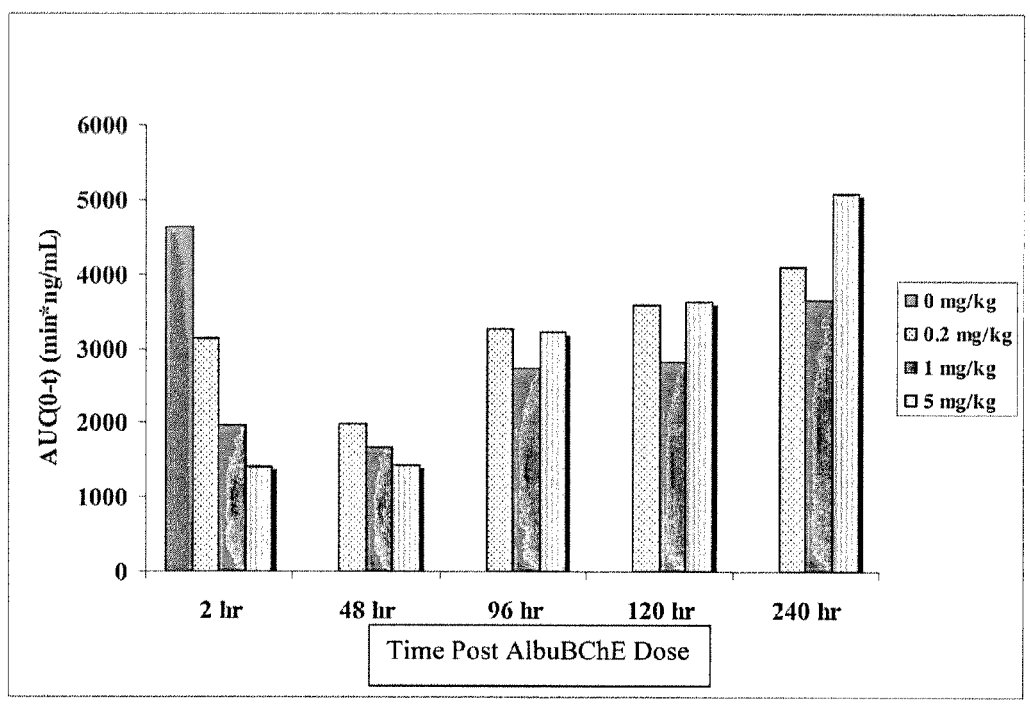
FIG. 11 shows mean benzoylecgonine $AUC_{(0-t)}$ following 1 mg/kg IV cocaine dose in control animals (n=2) and as a function of time post-AlbuBChE dose (n=3).

As can be observed in FIG. 5, the concentration-time profile of benzoylecgonine did not did not include a terminal elimination phase. As such, pharmacokinetic characterization of benzoylecgonine was limited to characterization of $AUC_{(0-t)}$. Summary table of mean AUC values as a function of AlbuBChE dose and time post-AlbuBChE dose in comparison with cocaine control group can be found in Table 11. Consistent with cocaine metabolic pathway (FIG. 9), benzoylecgonine AUC decreased as a function of AlbuBChE dose and increase as a function of time post-AlbuBChE administration as shown in FIG. 11.

Figure 6A:
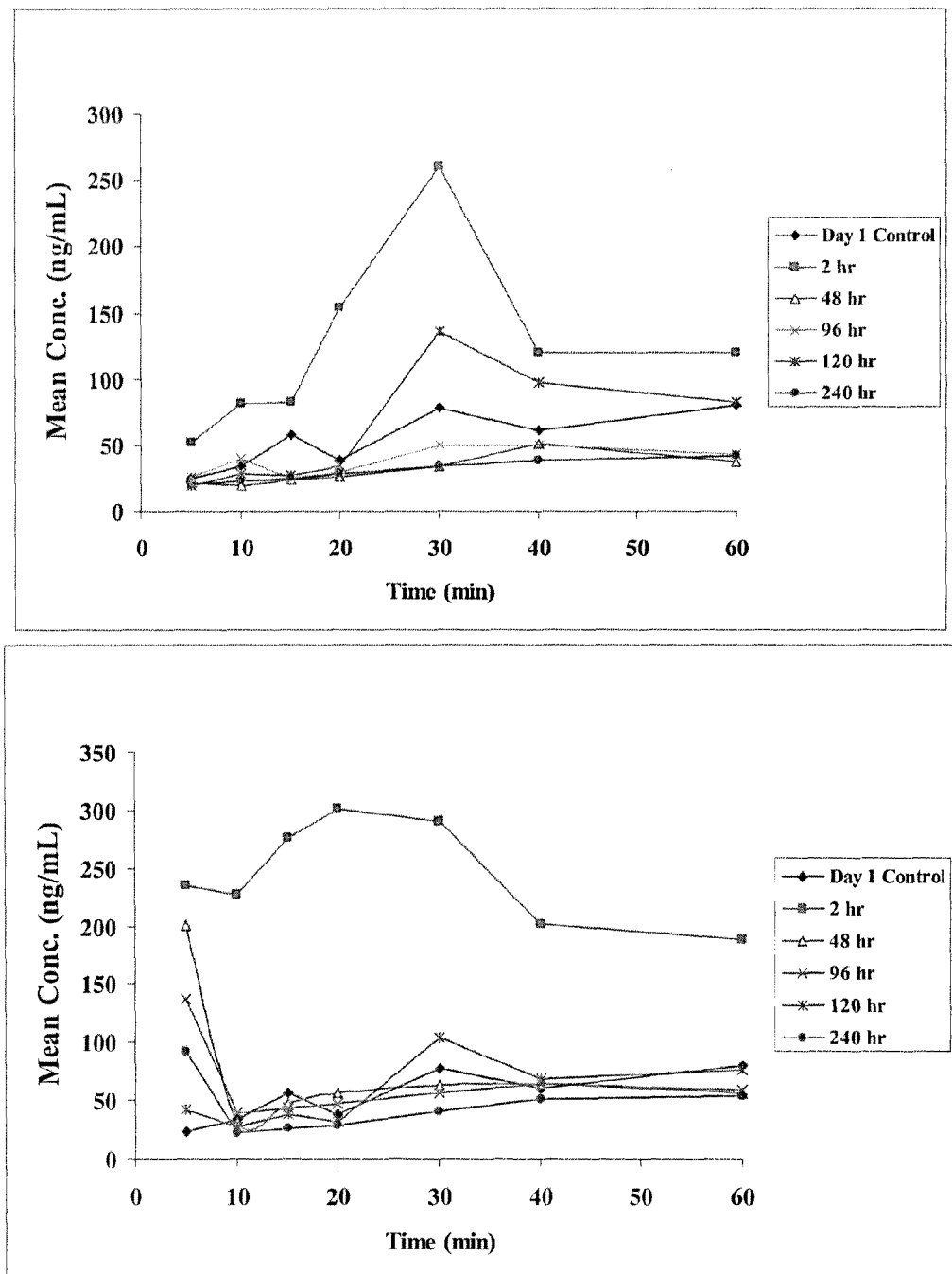
FIG. 6 shows mean ecgonine methyl ester concentration vs. time in control animals (n=2) and as a function of time post-AlbuBChE dose (n=3).
Figure 6B:
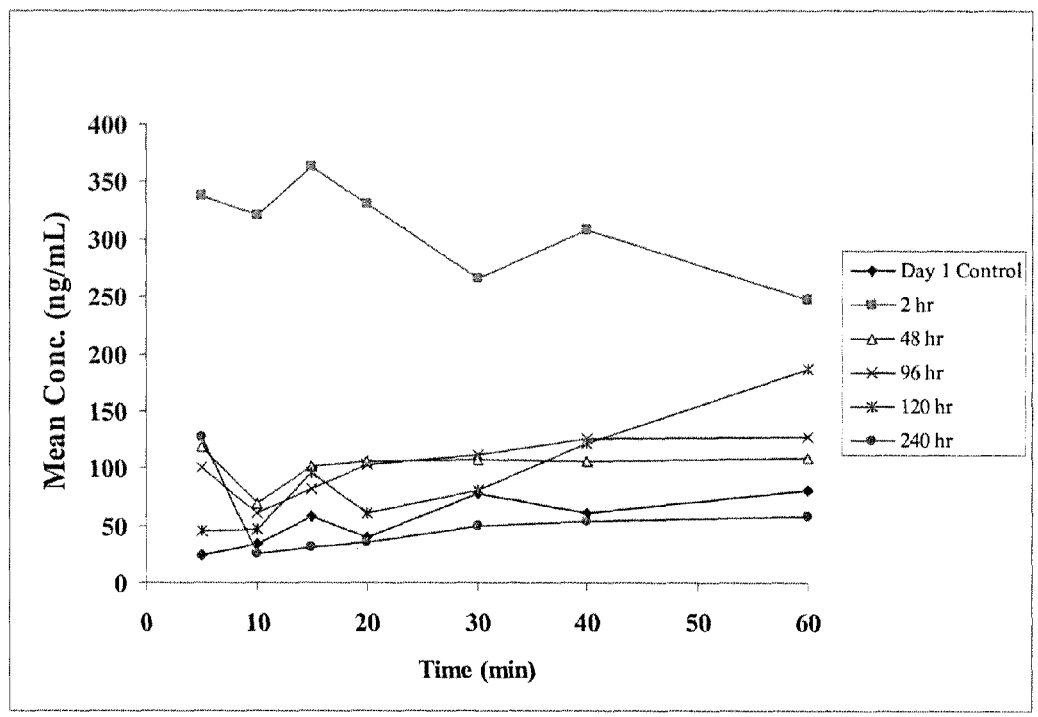

As can be observed in FIG. 6, the concentration-time profile of ecgonine methyl ester was flat and did not did not include a terminal elimination phase. As such, no pharmacokinetic characterization of ecgonine methyl ester was conducted. Theoretically, ecgonine methyl ester AUC should increase following AlbuBChE administration (FIG. 9). This increase was only evident at the cocaine dose administered at 2 hr post-AlbuBChE administration for all three AlbuBChE dose levels. AlbuBChE effect on ecgonine methyl ester could not be easily distinguished from control following cocaine administration at 48, 96, 120 or 240 hr post-AlbuBChE administration.

TABLE 10

Mean cocaine pharmacokinetic parameter values in Cynomolgus Monkeys following 1 mg/kg cocaine IV dose in control animals (n = 2) or at 2, 48, 72, 96, 120 and 240 hr post-AlbuBChE IM dose of 0.2, 1, or 5 mg/kg (n = 3 per dose group).

| Study Time (hr) | AlbuBChE Dose (mg/kg) | $t_{1/2}$ (min) | $C_0$ (ng/mL) | $AUC_{(0-t)}$ (min * ng/mL) | $AUC_{(0-\infty)}$ (min * ng/mL) | AUC % Extrap | Cl (mL/min/kg) | $V_{ss}$ (mL/kg) |
|---|---|---|---|---|---|---|---|---|
| Day 1 | Control | 41.8 | 371 | 14604 | 23407 | 35.4 | 48.5 | 2679 |
| 2 | 0.2 | NA | 628 | 11878 | NA | NA | NA | NA |
| 48 | 0.2 | 21.2 | 274 | 7713 | 9094 | 15.1 | 110 | 3503 |
| 96 | 0.2 | 21.1 | 451 | 11145 | 13008 | 14.9 | 78.1 | 2506 |
| 120 | 0.2 | 23.0 | 391 | 11611 | 14059 | 16.1 | 72.5 | 2338 |
| 240 | 0.2 | 29.2 | 549 | 13693 | 17650 | 21.6 | 57.4 | 2181 |
| 2 | 1 | NA | 422 | 7880 | NA | NA | NA | NA |
| 48 | 1 | 19.0 | 226 | 5965 | 6764 | 11.9 | 150 | 4304 |
| 96 | 1 | 23.9 | 288 | 10044 | 12313 | 18.4 | 81.6 | 2940 |
| 120 | 1 | 28.6 | 491 | 11526 | 14838 | 22.4 | 67.4 | 2687 |
| 240 | 1 | 31.0 | 467 | 14364 | 19623 | 26.7 | 51.1 | 2288 |
| 2 | 5 | NA | 271 | 3289 | NA | NA | NA | NA |
| 48 | 5 | 11.4 | 177 | 3015 | 3110 | 3.0 | 325 | 5729 |
| 96 | 5 | 21.3 | 190 | 6624 | 7729 | 14.2 | 129 | 4111 |
| 120 | 5 | 22.3 | 411 | 9378 | 11046 | 14.5 | 93.0 | 2857 |
| 240 | 5 | 33.8 | 424 | 12952 | 18578 | 29.2 | 55.6 | 2637 |

NA Not applicable or not determined because data did not permit.

TABLE 11

Summary Table of Mean Benzoylecgonine $AUC_{(0-t)}$ (min*ng/mL) in control animals and as a function of time post-AlbuBChE dose.

| | 2 hr | 48 hr | 96 hr | 120 hr | 240 hr |
|---|---|---|---|---|---|
| Control | 4641 | — | — | — | — |
| 0.2 mg/kg | 3136 | 1989 | 3270 | 3583 | 4089 |
| 1 mg/kg | 1960 | 1668 | 2741 | 2809 | 3660 |
| 5 mg/kg | 1405 | 1441 | 3222 | 3624 | 5088 |

PK/PD Analysis

Based on the mechanism of action of AlbuBChE it was anticipated that a direct effect inhibitory Emax model would be able to characterize the PK/PD relationship of AlbuBChE and cocaine.

Figure 8:
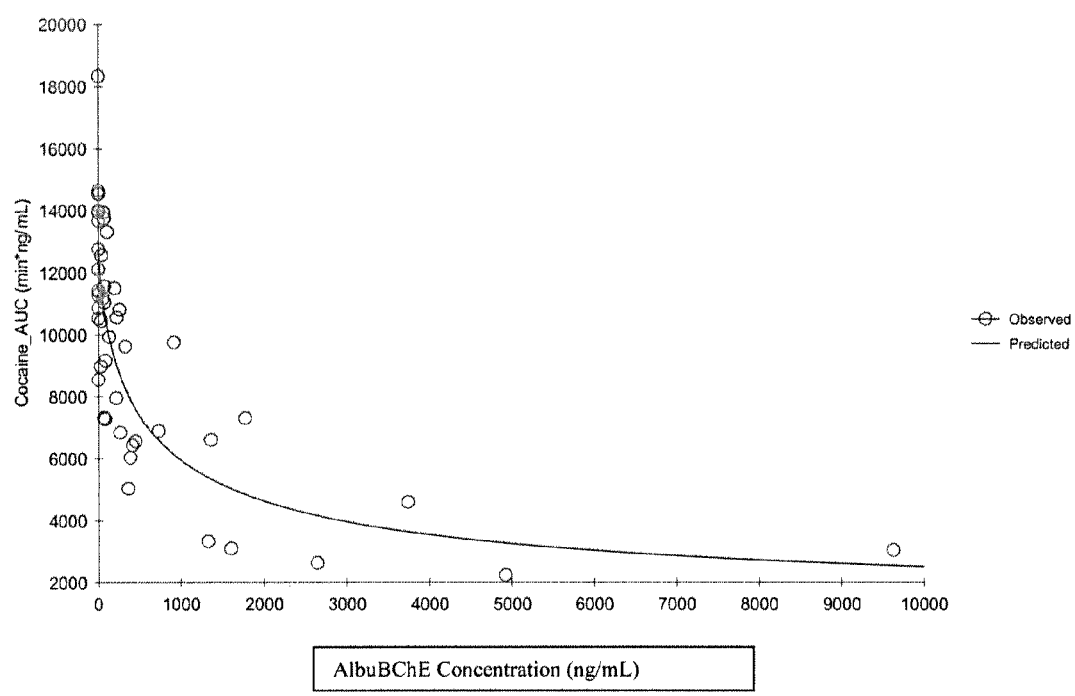
FIG. 8 shows AlbuBChE PK/PD analysis in cynomolgus monkeys following a single IM administration of 0.2, 1 or 5 mg/kg AlbuBChE dose. Cocaine was administered IV at a dose of 1 mg/kg in control animals or at 2, 48, 96, 120 and 240 hr post-AlbuBChE dose.

PK and PD data used in the analysis are shown in Table 12. The fit resulting from the direct Sigmoidal inhibitory Effect Emax model are shown in FIG. 8.

The data clearly shows the inverse relationship between AlbuBChE serum concentration and cocaine exposure. AlbuBChE serum concentration that may result in 50% decrease in cocaine concentration (EC50) was estimated by the model to be ~600 ng/mL. $E_{max}$, $E_0$, and Gamma values were 12909 (min*ng/mL), 1096 (min*ng/mL), and 0.708, respectively.

TABLE 12

AlbuBChE PK/PD analysis Cynomolgus Monkeys following a single IM administration of 0.2, 1 or 5 mg/kg AlbuBChE dose. Cocaine was administered IV at a dose of 1 mg/kg in control animals or at 2, 48, 96, 120 and 240 hr post-AlbuBChE dose.

| Animal ID | AlbuBChE IM Dose (mg/kg) | Time (hr) | AlbuBChE Conc. (ng/mL) | Cocaine $AUC_{(0-t)}$ (min * ng/mL) |
|---|---|---|---|---|
| 17689 | 0 | 2 | 0 | 18335 |
| 17690 | 0 | 2 | 0 | 10872 |
| 17691 | 0.2 | 2 | 107 | 13317 |
| 17692 | 0.2 | 2 | 257 | 10812 |
| 17693 | 0.2 | 2 | 196 | 11504 |
| 17694 | 1 | 2 | 1362 | 6597 |

TABLE 12-continued

AlbuBChE PK/PD analysis Cynomolgus Monkeys following a single IM administration of 0.2, 1 or 5 mg/kg AlbuBChE dose. Cocaine was administered IV at a dose of 1 mg/kg in control animals or at 2, 48, 96, 120 and 240 hr post-AlbuBChE dose.

| Animal ID | AlbuBChE IM Dose (mg/kg) | Time (hr) | AlbuBChE Conc. (ng/mL) | Cocaine $AUC_{(0-t)}$ (min * ng/mL) |
|---|---|---|---|---|
| 17695 | 1 | 2 | 918 | 9746 |
| 17696 | 1 | 2 | 1777 | 7297 |
| 17697 | 5 | 2 | 3740 | 4594 |
| 17698 | 5 | 2 | 9627 | 3039 |
| 17699 | 5 | 2 | 4923 | 2234 |
| 17691 | 0.2 | 48 | 0 | 8550 |
| 17692 | 0.2 | 48 | 66.4 | 7315 |
| 17693 | 0.2 | 48 | 80.7 | 7276 |
| 17694 | 1 | 48 | 389 | 6025 |
| 17695 | 1 | 48 | 363 | 5033 |
| 17696 | 1 | 48 | 264 | 6839 |
| 17697 | 5 | 48 | 1330 | 3323 |
| 17698 | 5 | 48 | 2644 | 2628 |
| 17699 | 5 | 48 | 1605 | 3095 |
| 17691 | 0.2 | 96 | 0 | 13936 |
| 17692 | 0.2 | 96 | 30 | 8978 |
| 17693 | 0.2 | 96 | 0 | 10522 |
| 17694 | 1 | 96 | 87 | 9166 |
| 17695 | 1 | 96 | 132 | 9925 |
| 17696 | 1 | 96 | 75 | 11042 |

TABLE 12-continued

AlbuBChE PK/PD analysis Cynomolgus Monkeys following
a single IM administration of 0.2, 1 or 5 mg/kg AlbuBChE dose.
Cocaine was administered IV at a dose of 1 mg/kg in control
animals or at 2, 48, 96, 120 and 240 hr post-AlbuBChE dose.

| Animal ID | AlbuBChE IM Dose (mg/kg) | Time (hr) | AlbuBChE Conc. (ng/mL) | Cocaine $AUC_{(0-t)}$ (min * ng/mL) |
|---|---|---|---|---|
| 17697 | 5 | 96 | 415 | 6428 |
| 17698 | 5 | 96 | 733 | 6887 |
| 17699 | 5 | 96 | 455 | 6556 |
| 17691 | 0.2 | 120 | 0 | 11293 |
| 17692 | 0.2 | 120 | 0 | 11428 |
| 17693 | 0.2 | 120 | 0 | 12111 |
| 17694 | 1 | 120 | 36 | 10451 |
| 17695 | 1 | 120 | 72 | 11561 |
| 17696 | 1 | 120 | 38 | 12568 |
| 17697 | 5 | 120 | 217 | 7954 |
| 17698 | 5 | 120 | 326 | 9620 |
| 17699 | 5 | 120 | 224 | 10560 |
| 17691 | 0.2 | 240 | 0 | 13669 |
| 17692 | 0.2 | 240 | 0 | 12762 |
| 17693 | 0.2 | 240 | 0 | 14649 |
| 17694 | 1 | 240 | 0 | 14533 |
| 17695 | 1 | 240 | 0 | 13998 |
| 17696 | 1 | 240 | 0 | 14560 |
| 17697 | 5 | 240 | 58 | 11173 |
| 17698 | 5 | 240 | 71 | 13745 |
| 17699 | 5 | 240 | 63 | 13937 |

PK parameters: AlbuBChE plasma concentrations per animals at 3[#], 48, 96, 120 and 240 hr post-AlbuBChE dose.
PB parameter: cocaine $AUC_{(0-t)}$ per animal at 2, 48, 96, 120 and 240 hr post-AlbuBChE dose.
[#]AlbuBChE concentration was not measured at 2 hr post-AlbuBChE dose, the 3 hr post-AlbuBChE dose was used in the analysis.

Animal Observations

The animals were observed throughout the study. There were no deaths during the study, and there were no clinical or cageside observations associated with administration of AlbuBChE at either dose. Administration of cocaine at a dose of 1 mg/kg without pre-treatment with the test article resulted in hyperactivity and increased respiratory rate with abdominal breathing. Cocaine-related observations were not observed for five days following pre-treatment with the test article at AlbuBChE doses ranging from 0.2 to 5 mg/kg but returned on study days 6 and 11.

Conclusions

AlbuBChE was well tolerated in cyomolgus monkeys following a single IM dose of 0.2, 1 or 5 mg/kg.

AlbuBChE absorption from IM site of administration was rapid. $T_{max}$ was observed at 3 hr for the 0.2 and 1 mg/kg and 6 hr for the 5 mg/kg dose. AlbuBChE exposure appears to increase in a more than proportional manner as a function of dose. Terminal elimination t½ increased from 31 to 62 hr between 1 and 5 mg/kg dose levels.

Cocaine was administered to control animals on Day 1 and at 2, 48, 96, 120 and 240 hr post-AlbuBChE dose. After each cocaine administration, multiple samples were drawn with the objective of determining the pharmacokinetic profile in response to decreasing serum levels of AlbuBChE. Cocaine $AUC_{(0-t)}$ decreased as a function of AlbuBChE dose and increase as a function of time post-AlbuBChE administration.

The duration of effect was related to AlbuBChE dose levels. AlbuBChE effect on cocaine AUC and clearance was evident up to 120 hr for 5 mg/kg dose, 96-120 hr for 1 mg/kg dose and 48 hr for the 0.2 mg/kg dose. Based on this data, a once or twice weekly dosing regimen of AlbuBChE is likely.

PK/PD relationship in cynomolgus monkeys appears to indicate an inverse relationship between AlbuBChE serum concentration and cocaine exposure. AlbuBChE serum concentration that may result in 50% decrease in cocaine concentration ($EC_{50}$) was estimated by the direct Sigmoidal Inhibitory Effect E, model model to be ~600 ng/mL.

EXAMPLE 2

AlbuBChE Pharmacokinetic Pharmacodynamic (PK/PD) Study in Squirrel Monkeys

Objective

To evaluate AlbuBChE pharmacokinetics and pharmacodynamics following a single 5 mg/kg intramuscular injection of AlbuBChE to Squirrel monkeys. AlbuBChE pharmacodynamic effect was measured following cocaine IV administration at a dose of 1 mg/kg in control animals or at 2, 72 and 96 hr post-AlbuBChE dose.

Study Design

Dose Level: AlbuBChE dose level of 5 mg/kg was selected based upon prior studies in Cynomolgous monkeys in which this dose level was found to be effective in decreasing cocaine exposure. Cocaine IV dose of 1 mg/kg was based on literature reports that such dose is sufficient to cause an effect in monkeys without causing excessive hyperactivity. The IM route of administration for AlbuBChE dosing was selected because this is an intended route of administration to humans.

TABLE 13

| Test System and Neat Materials | |
|---|---|
| Species | Primate -Squirrel - non-naïve ~0.8-1.2 kg |
| Wash out Period | ~1 week |
| In Life Period | 1 week, not including wash out |
| Number of Animals/Sex/Group | 3 males for AlbuBChE dose group<br>2 Control with vehicle |
| Number of Groups (including Control) | 1 dose groups + Control |
| Total number of animals on study | 5 |
| Test Article | AlbuBChE stock formulation was stored in a freezer (−75 ± 15° C.) and protected from light. |
| Pharmacodynamic Test Article | Cocaine hydrochloride was stored under ambient conditions protected from light. |
| Formulation Procedures | The AlbuBChE stock formulation was thawed at room temperature and once thawed was inverted gently. The stock was diluted with Formulation Buffer to achieve a concentration of 20 mg/mL.<br>The cocaine hydrochloride formulation was prepared by adding the required amount of cocaine hydrochloride to the formulation container, adding the required amount of |

TABLE 13-continued

Test System and Neat Materials saline to the container, and stirring until a clear formulation was observed. The final concentration was expressed as the hydrochloride salt. The formulation was filtered through a 0.22-μm PVDF syringe filter. The formulation was stored at −75 ± 15° C. until needed.

TABLE 14

Group Designation and Dosage Levels

| Group | Treatment | Dose Level (mg/kg) | Dose Concentration (mg/mL) | Dose Volume (mL/kg) | Number of Animals |
|---|---|---|---|---|---|
| 1 | Single IV dose of Cocaine | 1 | 1.0 | 1 | 2 |
| 2 | Single IM dose of AlbuBChE | 5 | 20 | 0.25 | 3 |
|   | Single IV dose of Cocaine at 2, 72 and 96 hours after AlbuBChE dose administration | 1 | 1.0 | 1 |  |

AlbuBChE Pharmacokinetic Samples

Blood samples (0.4 mL) were collected from the femoral vein and placed into serum separator tubes (SST) at pre-dose, 24, 72, 96 & 336 hrs post-dose (samples collected at 336 hr (14 days) post-dose were intended to evaluate immunogenicity. The samples were also analyzed for AlbuBChE concentration). Tubes were maintained at room temperature for at least 1 hour, but not to exceed 4 hours prior to centrifugation. Samples were centrifuged and at least 200 μL of serum was harvested and maintained on dry ice prior to storage at approximately −70° C.

Cocaine Pharmacokinetic Samples

Approximately 0.4 mL of whole blood was collected from the femoral vein after every cocaine dose at 5 and 30 minutes postdose. Blood was placed into $K_2$EDTA blood collection tubes with esterase inhibitor (diisopropylfluorophosphate (DFP). Tubes were inverted several times and placed on wet ice upon collection. Samples were centrifuged at 2-8° C. within 45 minutes of collection. The resultant plasma will be recovered and a single 200 μL aliquot of plasma was placed into polypropylene tubes. Plasma samples was frozen over dry ice and stored at approximately −70° C.

AlbuBChE Sample Analysis

The following paragraph briefly describes the ELISA based assay employed in the measurement of AlbuBChE concentrations in serum samples.

Immulon 4 HBX plates are coated with 100 ul of anti-human BChE mAb 002-01 (Abcam ab17246) at 1 μg/mL in PBS, overnight at 4 C. Blocking is done with 2% casein in phosphate buffered saline (PBS), 200 μL/well, 2 hours at room temperature. After washing, 100 μL of diluted serum samples are added to the plates along with standards. Standards are generated through 2.6 fold, serial dilution of AlbuBChE from 420 to 5.2 ng/mL. Serum samples and standards are maintained at 10% serum by dilution with buffer containing pooled cynomolgus monkey serum. A wash step precedes detection with 100 μl of anti-HSA mAb-6502-HRP at 0.04 μg/mL for 1 hour. Wells are washed again, prior to developing with 100 μl, of tetramethylbenzidine substrate. After 15 minutes the reaction is terminated with 100 μL/well of 1N $H_2SO_4$ and read on SpectraMax plate reader at 450/570 nm. Values for unknown serum samples are calculated by interpolation of standard curve generated by 5-parameter fit of AlbuBChE standards. Serum samples collected at predose and on Day 14 postdose were also analyzed for immunogenicity.

AlbuBChE Pharmacokinetic and PK/PD Analysis

AlbuBChE pharmacokinetic parameter values were determined using serum concentration-time profiles for individual animals. The computer software WinNonlin Professional (Version 4.0.1 Pharsight Corporation, USA) was used. Specifically the model for non-compartmental analysis with extravascular input was applied.

In spite of the limited amount of data, an attempt was made to characterize PK/PD relationship. The computer software WinNonlin Professional (Version 4.0.1 Pharsight Corporation, USA) was used. Specifically the direct Inhibitory Effect $E_{max}$ model was use in which $E_{max}$ was assumed at AlbuBChE concentration of zero. The model equation can be described as follows:

$$E = E_{max} * (1 - (C/(C + EC50)))$$

The PD parameter used in the analysis was cocaine plasma concentration at 5 min post-cocaine dose. PK parameters used in the model were AlbuBChE plasma concentrations at 2, 72 and 96 hr post-AlbuBChE dose. Due to the fact that AlbuBChE concentration was not measured at 2 hr post-AlbuBChE dose, the 1st time sample collected was used in the analysis (24 hr post-AlbuBChE dose) with the assumptions that AlbuBChE concentration at 24 hr post AlbuBChE dose may reflect AlbuBChE concentration at 2 hr post AlbuBChE dose. Due to the limited data and the assumptions used in the analysis, parameter values from this PK/PD analysis need to be viewed as approximate estimates.

Results

AlbuBChE

Figure 12:
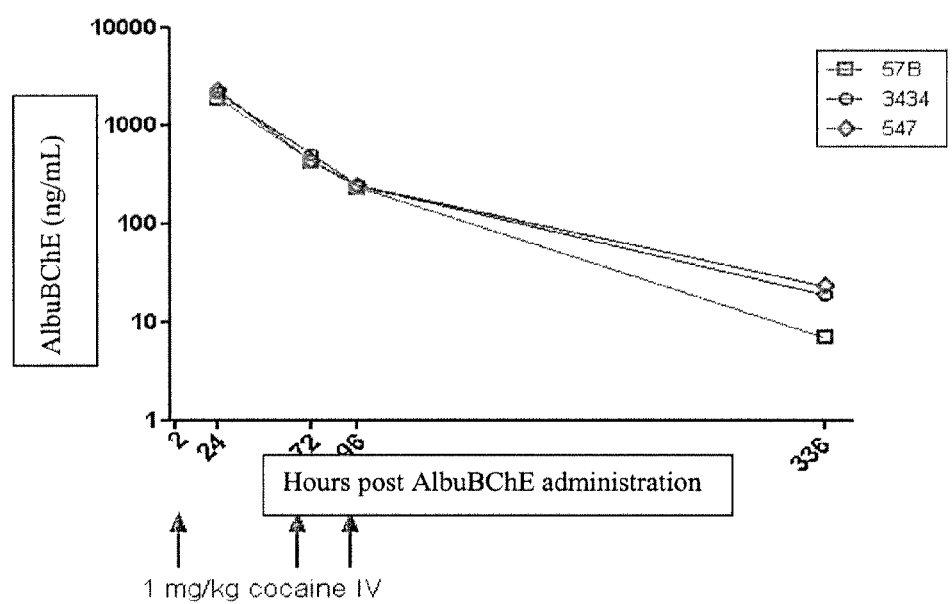
FIG. 12 shows AlbuBChE serum concentration-time profile in individual squirrel monkeys following a single IM administration of 5 mg/kg AlbuBChE dose (semi-logarithmic scale).

Table 15 and FIG. 12 provide AlbuBChE serum concentration-time profiles in three male Squirrel monkeys following a single intramuscular administration of 5 mg/kg AlbuBChE dose. Table 16 summarizes AlbuBChE Squirrel monkeys pharmacokinetic parameter values.

AlbuBChE terminal elimination slope was well characterized as indicated by Rsq values being higher than 0.9. Area under the curve was also well characterized as indicated by % AUC extrapolated being less than 20%. The initial absorption phase of AlbuBChE concentration-time profile was not characterized since the first sample was collected at 24 hr post-dose. As such, $T_{max}$ and $C_{max}$ reported are apparent since actual $T_{max}$ can be expected to occur between 3 and 6 hr. AlbuBChE exposure was consistent for the three animals, with differences in levels only clearly evident after 2 weeks. For example, AUC values for the three animals were in a tight range with % CV of ~7%. AlbuBChE terminal elimination t½ was estimated to range from 45.5 to 65.5 hr (average half-life of 56.6 hours).

TABLE 15

AlbuBChE Serum Concentration (ng/mL) vs. time (hr) Profile
in individual Squirrel Monkeys following a single IM
administration of 5 mg/kg/animal AlbuBChE dose.

| Time (hr) | MKY 547 | MKY 3434 | MKY 53B |
|---|---|---|---|
| 0 | <LLOD | <LLOD | <LLOD |
| 24 | 2340.2 | 2296.7 | 2036.7 |
| 72 | 436.9 | 517.7 | 433.7 |
| 96 | 247.5 | 247.5 | 233.5 |
| 336 | 23.4 | 19.0 | 7.0 |

TABLE 16

AlbuBChE Pharmacokinetic Parameter Values in
individual Squirrel Monkeys following a single IM
administration of 5 mg/kg/animal AlbuBChE dose.

| MKY ID | Rsq | No. Points Lambda-z | $t^{1/2}$ (hr) | Tmax (hr) | Cmax (ng/mL) | AUC(0-t) (hr * ng/mL) | AUC(0-∞) (hr * ng/mL) | AUC % Extrap |
|---|---|---|---|---|---|---|---|---|
| 547 | 0.990 | 3 | 65.5 | 24 | 2340 | 135454 | 137666 | 1.61 |
| 3434 | 0.983 | 3 | 58.8 | 24 | 2297 | 136268 | 137881 | 1.17 |
| 53B | 0.997 | 3 | 45.5 | 24 | 2037 | 120596 | 121056 | 0.380 |
| | | | | | Mean | 130773 | 132201 | |
| | | | | | SD | 8822 | 9652 | |
| | | | | | % CV | 6.75 | 7.30 | |

Cocaine and Metabolites

Cocaine was administered IV at a dose of 1 mg/kg in control animals (n=2) or at 2, 72 and 96 hr post-AlbuBChE dose (n=3). The bioanalytical method measured the plasma concentration of cocaine and two of its metabolites: ecgonine methyl ester and benzoylecgonine. Cocaine metabolic pathway is shown in FIG. 9, ecgonine methyl ester metabolite is formed directly from cocaine through the butrylcholine esterase enzyme. As such, this metabolite can be predicted to increase following AlbuBChE administration.

Figure 13:
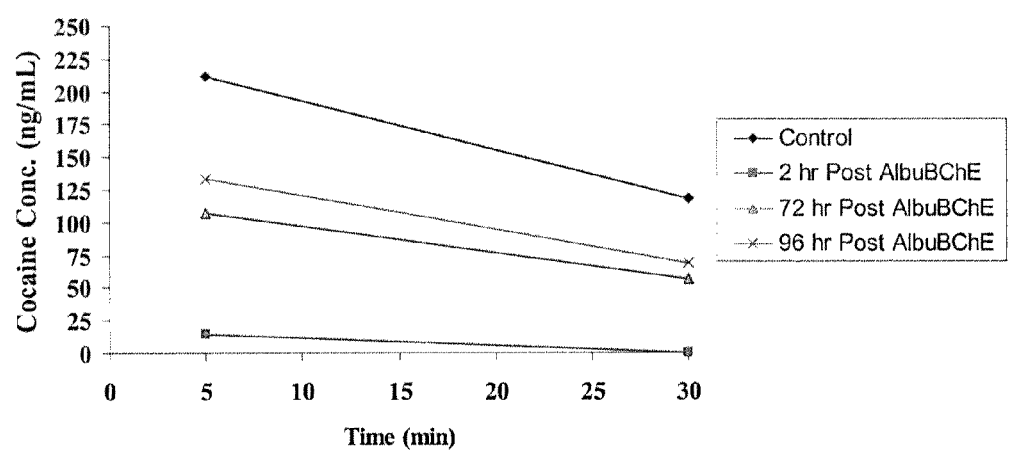
FIG. 13 shows mean cocaine concentration vs. time in control animals (n=2) and as a function of time post-AlbuBChE dose (n=3).

Individual and mean cocaine plasma concentration (ng/mL) vs. time (hr) data in control and AlbuBChE treated Squirrel monkeys are shown in Table 17. A summary of the mean cocaine concentrations vs. time are shown in FIG. 13. Highest cocaine concentrations were observed in the control animals. The lowest cocaine levels were observed at 2 hr following AlbuBChE administration reaching values that are approximately 7% of control. Cocaine concentrations increased as a function of time post-AlbuBChE administration yet even at 96 hr post-AlbuBChE administration, cocaine concentration were still 60% of control animals.

Figure 14:
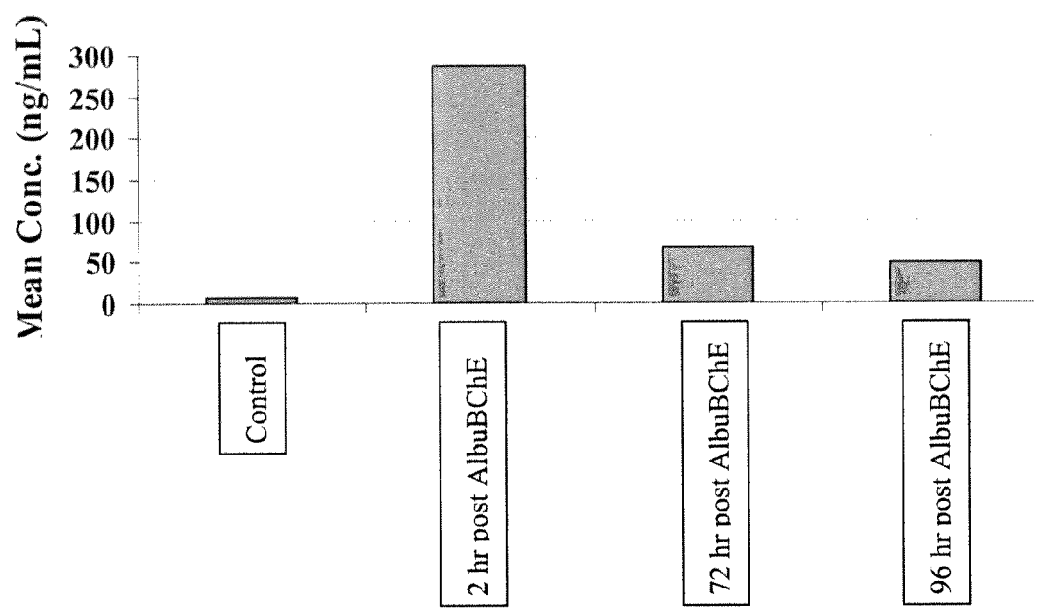
FIG. 14 shows mean ecgonine methyl ester concentration at 5 min following 1 mg/kg IV cocaine dose in control animals (n=2) and as a function of time post-AlbuBChE dose (n=3).

Individual and mean ecgonine methyl ester plasma concentration (ng/mL) vs. time (hr) data in control and AlbuBChE treated Squirrel monkeys are shown in Table 18. A summary of the mean ecgonine methyl ester concentrations are shown in FIG. 14. As expected, ecgonine methyl ester concentration at 5 min after cocaine administration were low in the control animals. The values were ~40 fold higher in the AlbuBChE treated animals with the highest concentrations observed at 2 hr post-AlbuBChE dose. Ecgonine methyl ester concentrations decreased as a function of time post-AlbuBChE administration yet even at 96 hr post-AlbuBChE administration, ecgonine methyl ester concentration were still higher than in the control animals.

Figure 15:
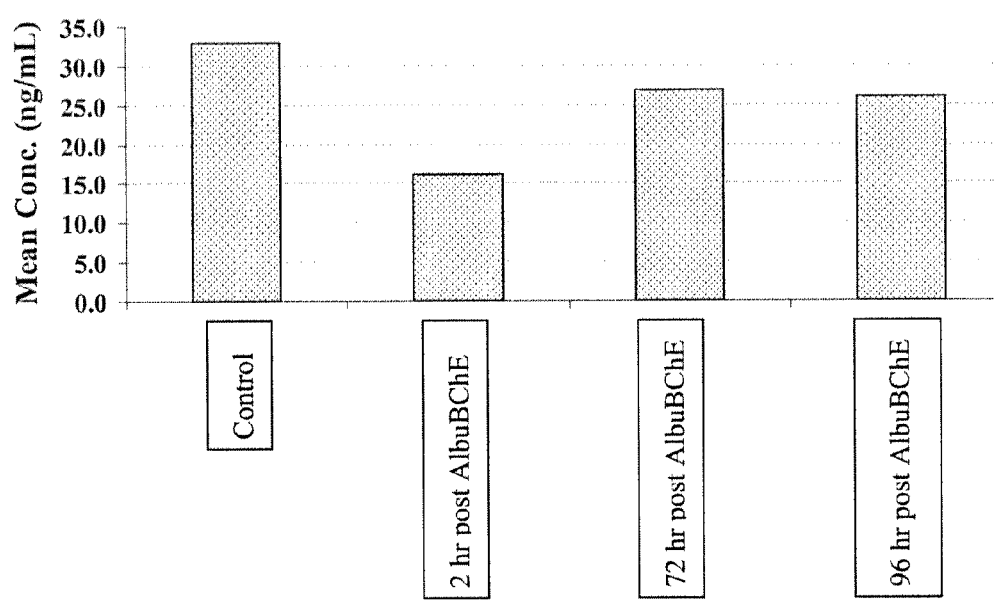
FIG. 15 shows mean benzoylecgonine concentration at 5 min following 1 mg/kg IV cocaine dose in control animals (n=2) and as a function of time post-AlbuBChE dose (n=3).

Individual and mean benzoylecgonine plasma concentration (ng/mL) vs. time (hr) data in control and AlbuBChE treated Squirrel monkeys are shown in Table 19. A summary of the mean benzoylecgonine concentrations are shown in FIG. 15. As illustrated, AlbuBChE effect on the cocaine metabolite benzoylecgonine was less pronounced.

Figure 16:
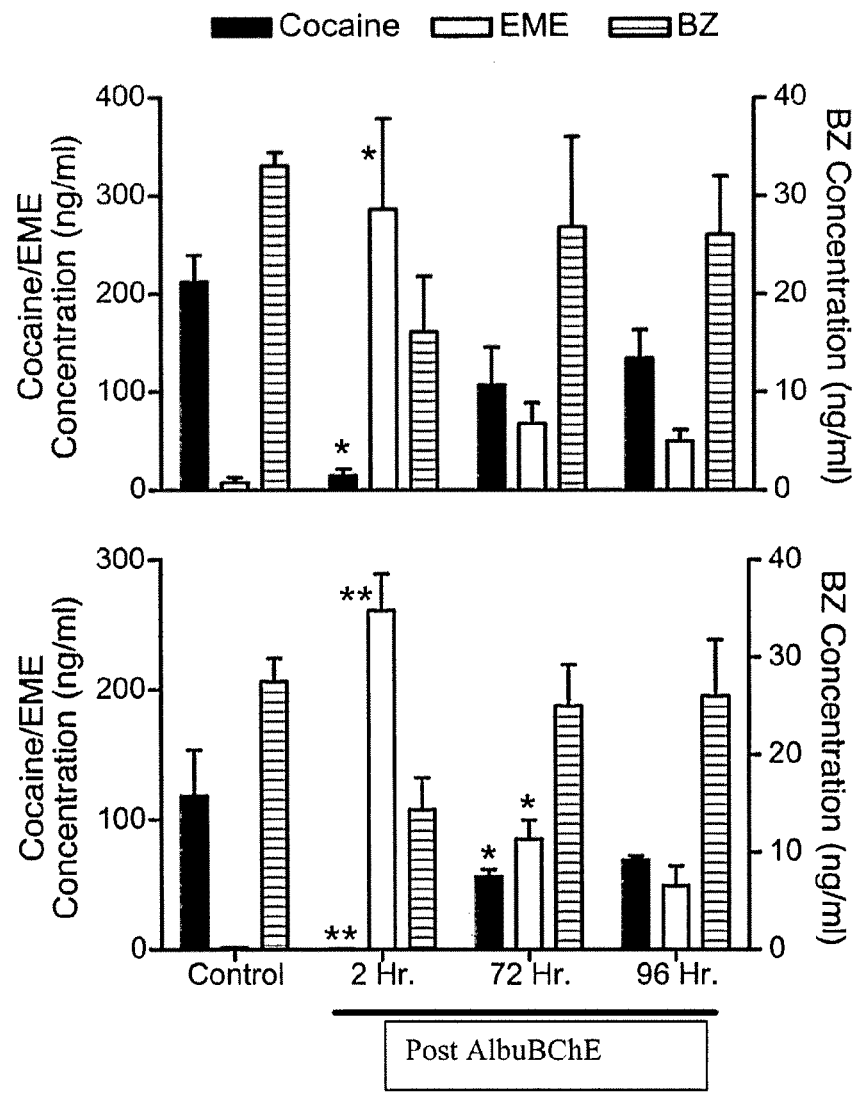
FIG. 16 shows a summary of squirrel monkey blood levels of cocaine and the cocaine metabolites ecgonine methyl ester (EME) and benzoylecgonine (BZ) at 5 minutes (top panel) and 30 minutes (bottom panel) following cocaine injection.

FIG. 16 shows a summary of the blood levels of cocaine and the cocaine metabolites ecgonine methyl ester (EME) and benzoylecgonine (BZ) at 5 and 30 min following the cocaine injection. Compared to a control cocaine injection following administration of vehicle, 2 hours following administration of AlbuBChE cocaine blood levels were significantly reduced at both the 5- and 30-min time points ($F_{3,7}$=7.34, p<0.05 and $F_{3,7}$=14.4, p<0.005 respectively). Seventy-two hours following AlbuBChE cocaine levels were still significantly below control levels 30-min post cocaine. The effects of AlbuBChE were not significant at either 5 or 30 min time point 96 hours following administration. The effects of AlbuBChE on EME levels were similar, but in the opposite direction to those of cocaine. Blood levels of EME were elevated at both the 5- and 30 min time point 2 hr following AlbuBChE administration ($F_{3,7}$=5.6, p<0.05 and $F_{3,7}$=33.3, p<0.001). Blood levels of EME remained significantly elevated at 72 hours following AlbuBChE for the 30 min time point. While blood levels of BZ appeared to be slightly reduced 2 hr following AlbuBChE, these effects were not significant.

TABLE 17

Cocaine Plasma Concentration (ng/mL) vs. time (hr)
in individual Squirrel Monkeys following a single IM
administration of 5 mg/kg AlbuBChE dose. Cocaine was
administered IV at a dose of 1 mg/kg in control animals (n = 2)
or at 2, 72 and 96 hr post-AlbuBChE dose (n = 3).

| Time Post-AlbuBChE Dose | MKY 547 | MKY 3434 | MKY 53B | Mean | SD | % CV |
|---|---|---|---|---|---|---|
| Cocaine Concentration at 5 min following Cocaine dose at 2, 72 and 96 hr post-AlbuBChE Dose | | | | | | |
| 2 | 0.575 | 20.0 | 22.4 | 14.3 | 12.0 | 83.5 |
| 72 | 41.3 | 176 | 104 | 107 | 67.4 | 62.9 |
| 96 | 97.9 | 191 | 112 | 134 | 50.2 | 37.5 |
| Cocaine Concentration at 30 min following Cocaine dose at 2, 72 and 96 hr post-AlbuBChE Dose | | | | | | |
| 2 | 0.581 | 0.115 | 0.261 | 0.319 | 0.238 | 74.7 |
| 72 | 65.0 | 57.9 | 44.9 | 55.9 | 10.2 | 18.2 |
| 96 | 62.9 | 75.6 | 67.1 | 68.5 | 6.47 | 9.44 |

TABLE 17-continued

Cocaine Plasma Concentration (ng/mL) vs. time (hr) in individual Squirrel Monkeys following a single IM administration of 5 mg/kg AlbuBChE dose. Cocaine was administered IV at a dose of 1 mg/kg in control animals (n = 2) or at 2, 72 and 96 hr post-AlbuBChE dose (n = 3).

Cocaine Concentration at 5 and 30 min following cocaine dose in control animals

| Time post cocaine dose | MKY 548 | MKY 27B | Mean |
|---|---|---|---|
| 5 min | 185 | 239 | 212 |
| 30 min | 82.6 | 154 | 118 |

Summary Table of Mean Cocaine Concentration vs. time in control animals and as a function of time post-AlbuBChE dose

| Time Post Cocaine (min) | Control | 2 hr Post-AlbuBChE | 72 hr Post-AlbuBChE | 96 hr Post-AlbuBChE |
|---|---|---|---|---|
| 5 | 212 | 14.3 | 107 | 134 |
| 30 | 118 | 0.319 | 55.9 | 68.5 |

<LLOQ (1 ng/mL)

TABLE 18

Ecgonine Methyl Ester Plasma Concentration (ng/mL) vs. time (hr) in individual Squirrel Monkeys following a single IM administration of 5 mg/kg AlbuBChE dose. Cocaine was administered IV at a dose of 1 mg/kg in control animals (n = 2) or at 2, 72 and 96 hr post-AlbuBChE dose (n = 3).

| Time Post-AlbuBChE Dose | MKY 547 | MKY 3434 | MKY 53B | Mean | SD | % CV |
|---|---|---|---|---|---|---|
| Ecgonine Methyl Ester Concentration at 5 min following Cocaine dose at 2, 72 and 96 hr post-AlbuBChE Dose | | | | | | |
| 2 | 109 | 417 | 333 | 286 | 159 | 55.6 |
| 72 | 29.3 | 101 | 73.2 | 67.8 | 36.2 | 53.3 |
| 96 | 40.5 | 72.3 | 35.8 | 49.5 | 19.9 | 40.1 |
| Ecgonine Methyl Ester Concentration at 30 min following Cocaine dose at 2, 72 and 96 hr post-AlbuBChE Dose | | | | | | |
| 2 | 252 | 314 | 218 | 261 | 48.7 | 18.6 |
| 72 | 61.3 | 112 | 81.7 | 85.0 | 25.5 | 30.0 |
| 96 | 25.7 | 76.8 | 45.2 | 49.2 | 25.8 | 52.4 |

Ecgonine Methyl Ester Concentration at 5 and 30 min following cocaine dose in control animals

| Time post cocaine dose | MKY 548 | MKY 27B | Mean |
|---|---|---|---|
| 5 min | 1.61 | 12.8 | 7.21 |
| 30 min | 1.27 | 1.34 | 1.31 |

Summary Table of Mean Ecgonine Methyl Ester Concentration vs. time in control animals and as a function of time post-AlbuBChE dose

| Time Post Cocaine (min) | Control | 2 hr Post-AlbuBChE | 72 hr Post-AlbuBChE | 96 hr Post-AlbuBChE |
|---|---|---|---|---|
| 5 | 7.21 | 286 | 67.8 | 49.5 |
| 30 | 1.31 | 261 | 85.0 | 49.2 |

<LLOQ (1 ng/mL)

TABLE 19

Benzoylecgonine Plasma Concentration (ng/mL) vs. time (hr) in individual Squirrel Monkeys following a single IM administration of 5 mg/kg AlbuBChE dose. Cocaine was administered IV at a dose of 1 mg/kg in control animals (n = 2) or at 2, 72 and 96 hr post-AlbuBChE dose (n = 3).

| Time Post-AlbuBChE Dose | MKY 547 | MKY 3434 | MKY 53B | Mean | SD | % CV |
|---|---|---|---|---|---|---|
| Benzoylecgonine Concentration at 5 min following Cocaine dose at 2, 72 and 96 hr post-AlbuBChE Dose | | | | | | |
| 2 | 4.83 | 23.3 | 20.1 | 16.1 | 9.87 | 61.4 |
| 72 | 9.93 | 41.7 | 28.8 | 26.8 | 16.0 | 59.6 |
| 96 | 15.5 | 36.2 | 26.3 | 26.0 | 10.4 | 39.8 |
| Benzoylecgonine Concentration at 30 min following Cocaine dose at 2, 72 and 96 hr post-AlbuBChE Dose | | | | | | |
| 2 | 11.1 | 20.8 | 10.9 | 14.3 | 5.66 | 39.7 |
| 72 | 20.7 | 33.4 | 21 | 25.0 | 7.25 | 29.0 |
| 96 | 18.9 | 37.6 | 21.5 | 26.0 | 10.1 | 39.0 |

Benzoylecgonine Concentration at 5 and 30 min following cocaine dose in control animals

| Time post cocaine dose | MKY 548 | MKY 27B | Mean |
|---|---|---|---|
| 5 min | 34.4 | 31.6 | 33.0 |
| 30 min | 25.1 | 29.9 | 27.5 |

Summary Table of Mean Benzoylecgonine Concentration vs. time in control animals and as a function of time post-AlbuBChE dose

| Time Post Cocaine (min) | Control | 2 hr Post-AlbuBChE | 72 hr Post-AlbuBChE | 96 hr Post-AlbuBChE |
|---|---|---|---|---|
| 5 | 33.0 | 16.1 | 26.8 | 26.0 |
| 30 | 27.5 | 14.3 | 25.0 | 26.0 |

<LLOQ (1 ng/mL)

AlbuBChE PR/PD Relationship

Figure 17:
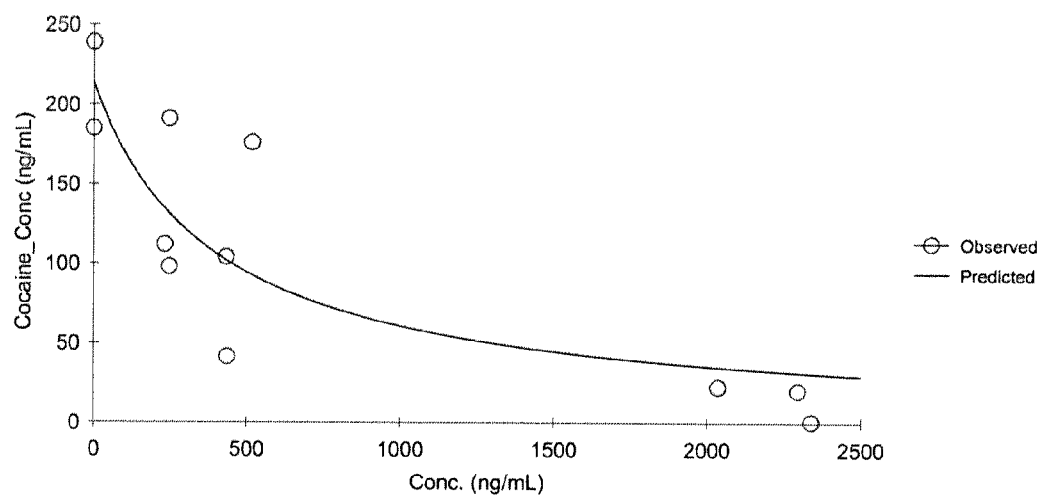
FIG. 17 shows AlbuBChE FK/PD analysis in Squirrel Monkeys following a single IM administration of 5 mg/kg AlbuBChE dose. Cocaine was administered IV at a dose of 1 mg/kg in control animals (n=2) or at 2, 72 and 96 hr post-AlbuBChE dose (n=3).
Figure 18:
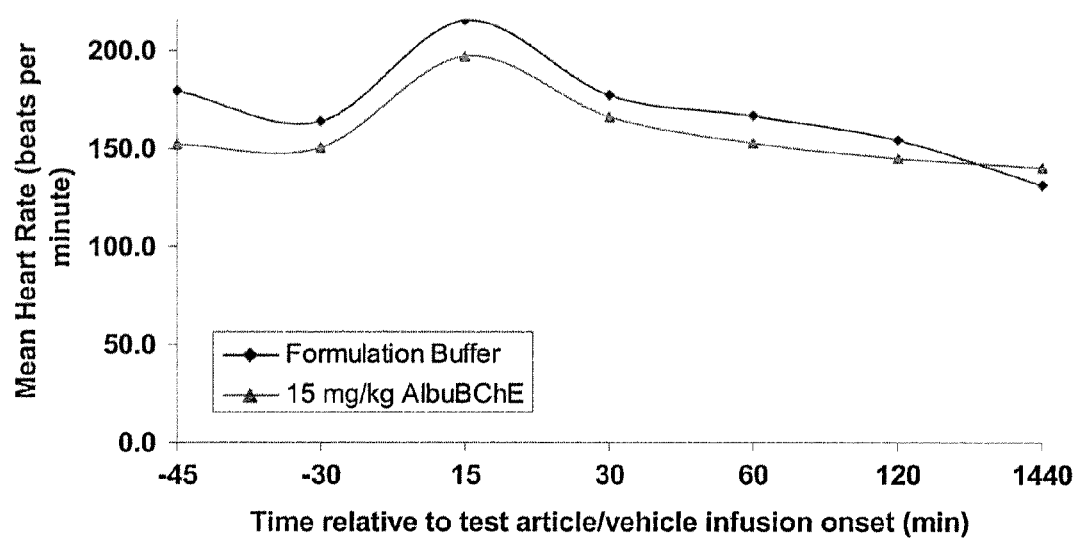
FIG. 18 shows mean heart rate vs. time in cynomolgus monkeys prior to and following a single IM administration of 15 mg/kg AlbuBChE dose or formulation buffer.
Figure 19:
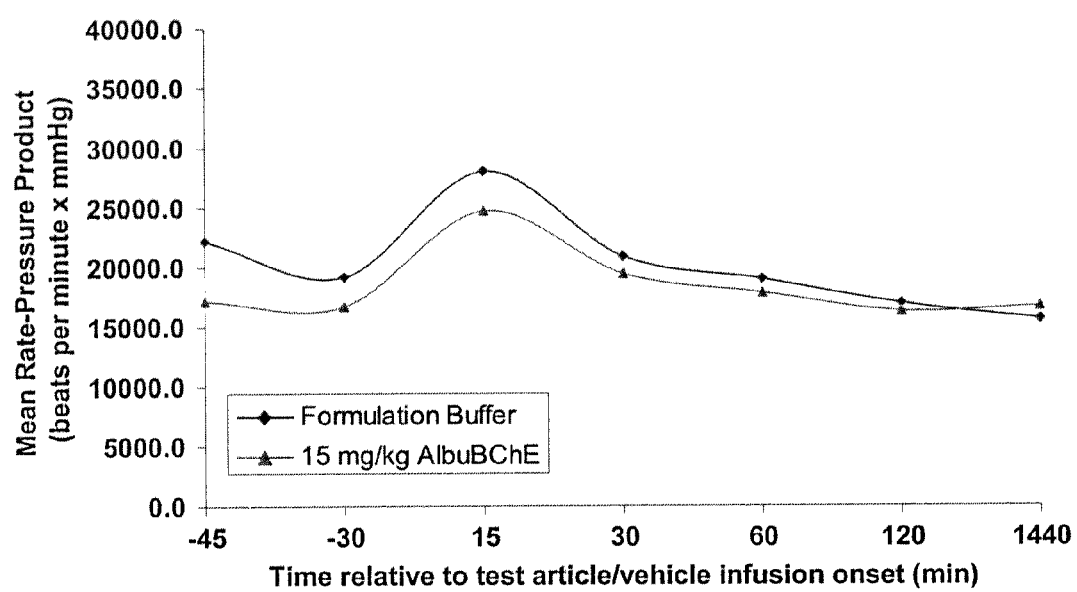
FIG. 19 shows mean heart rate pressure product vs. time in cynomolgus monkeys prior to and following a single IM administration of 15 mg/kg AlbuBChE dose or formulation buffer.
Figure 20:
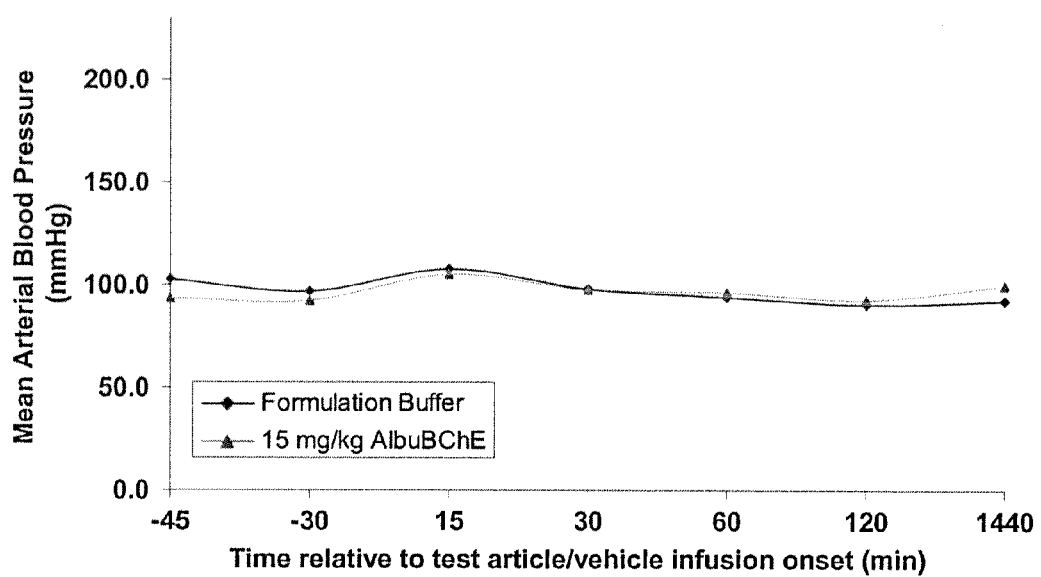
FIG. 20 shows mean arterial blood pressure vs. time in cynomolgus monkeys prior to and following a single IM administration of 15 mg/kg AlbuBChE dose or formulation buffer.
Figure 21:
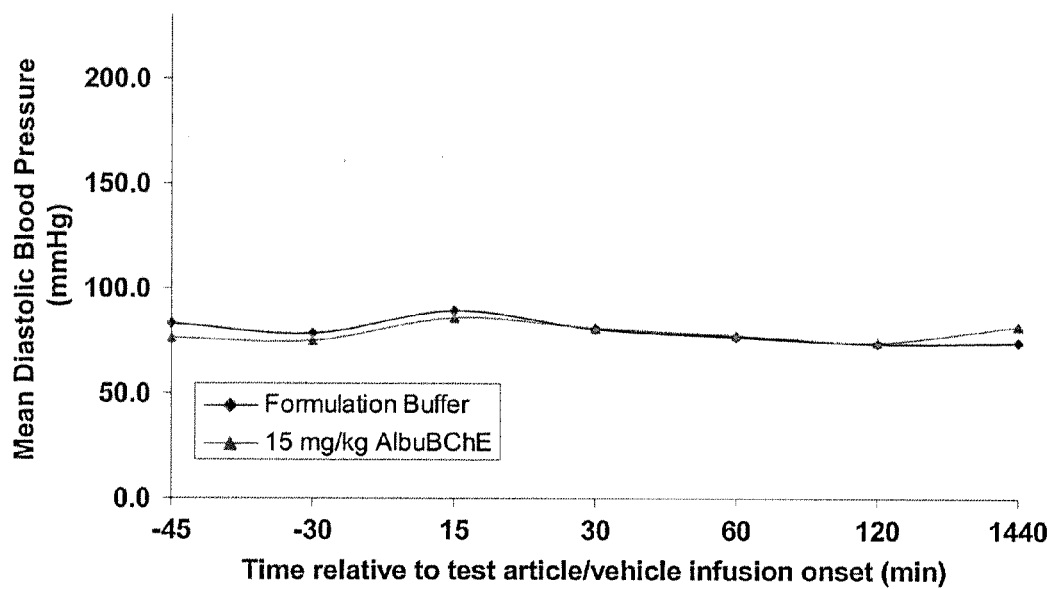
FIG. 21 shows mean diastolic blood pressure vs. time in cynomolgus monkeys prior to and following a single IM administration of 15 mg/kg AlbuBChE dose or formulation buffer.
Figure 22:
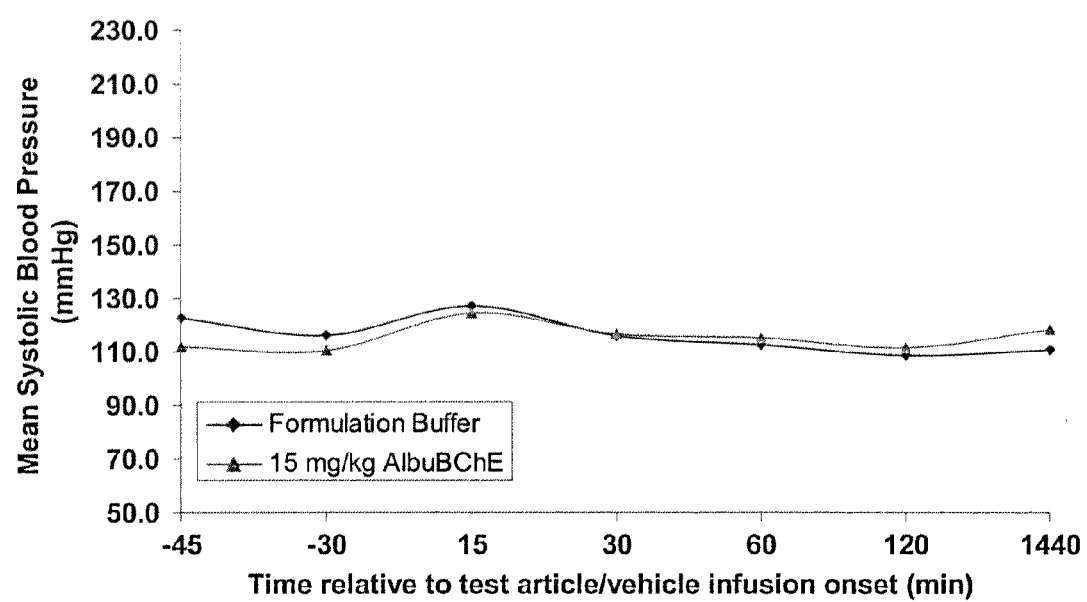
FIG. 22 shows mean systolic blood pressure vs. time in cynomolgus monkeys prior to and following a single IM administration of 15 mg/kg AlbuBChE dose or formulation buffer.
Figure 23:
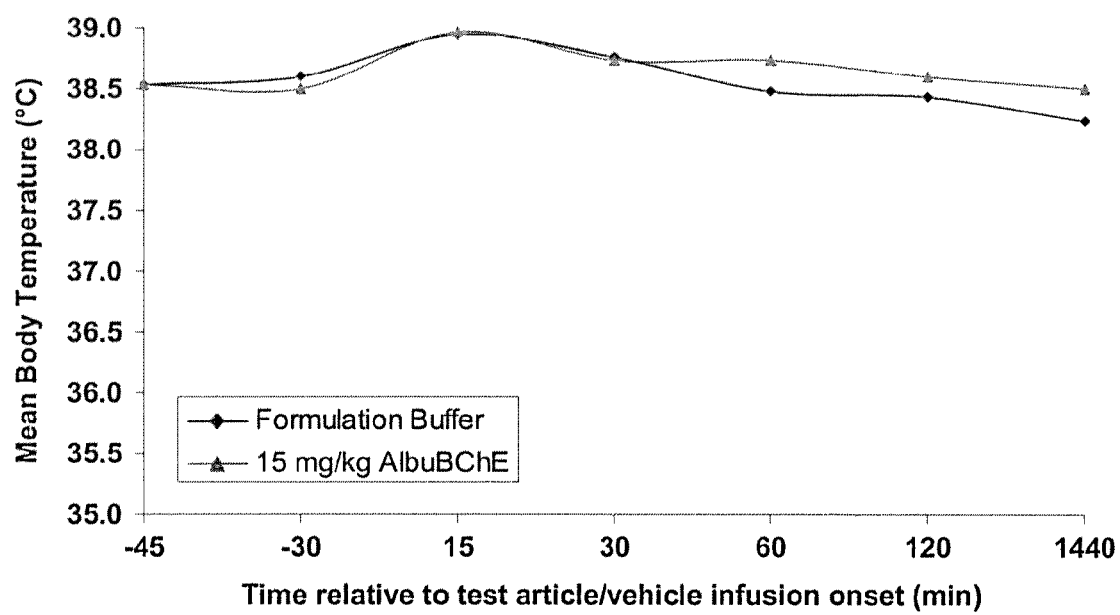
FIG. 23 shows mean body temperature vs. time in cynomolgus monkeys prior to and following a single IM administration of 15 mg/kg AlbuBChE dose or formulation buffer.
Figures 24A, 24B:
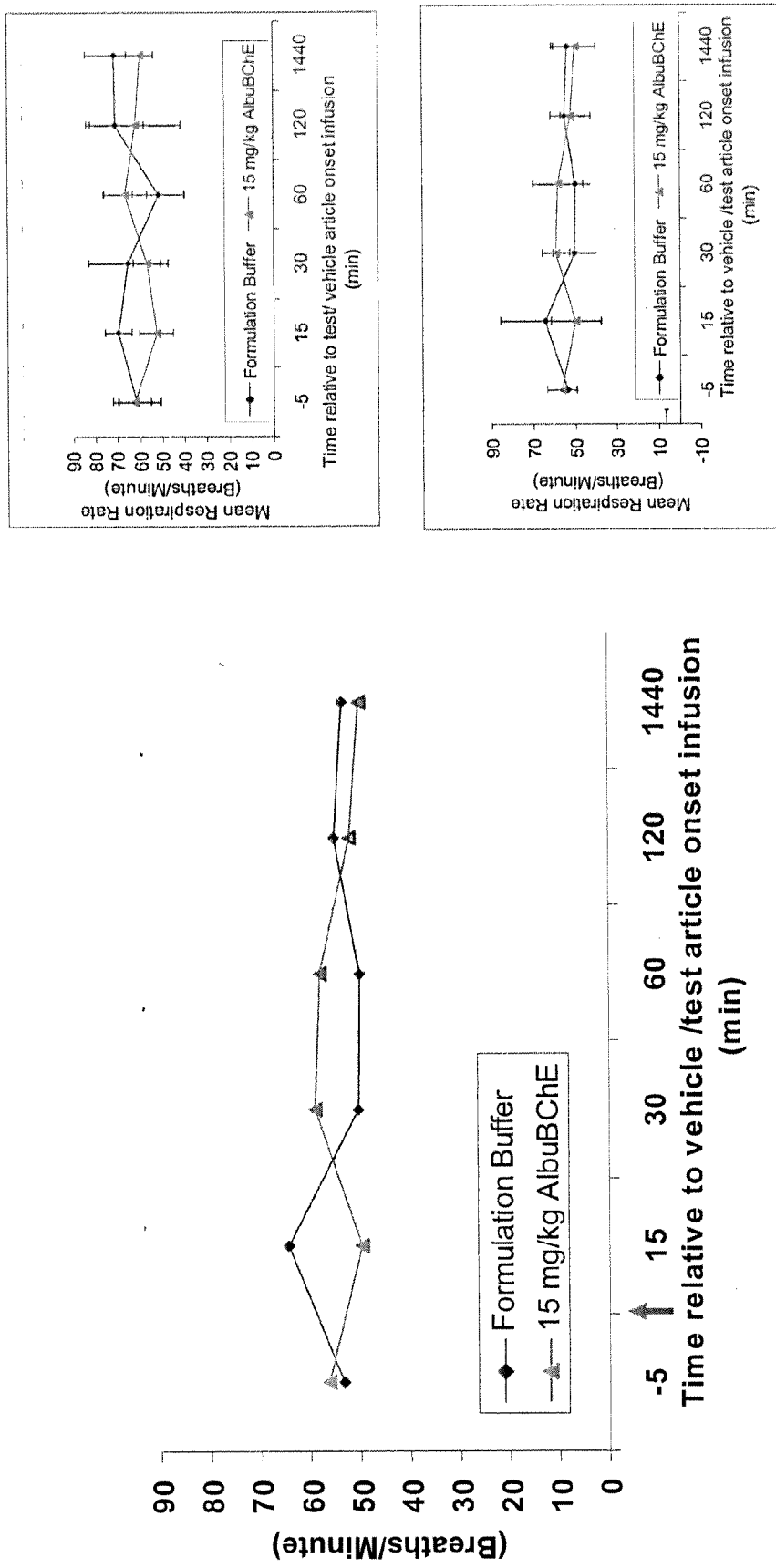
FIG. 24A shows mean respiration rate vs. time in cynomolgus monkeys prior to and following a single IM administration of 15 mg/kg AlbuBChE dose or formulation buffer. Data for male cynomolgus monkeys is shown in FIG. 24B, top panel, and data for female cynomolgus monkeys is shown in FIG. 24B, bottom panel.
Figure 26B:
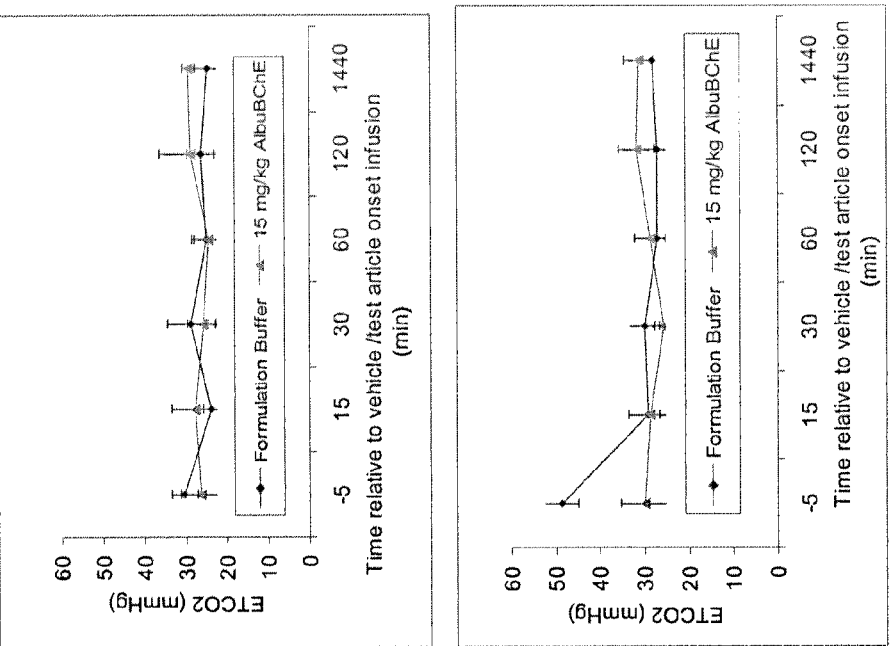
FIG. 26A shows mean ETCO2 levels vs. time in cynomolgus monkeys prior to and following a single IM administration of 15 mg/kg AlbuBChE dose or formulation buffer. Data for male cynomolgus monkeys is shown in FIG. 26B, top panel, and data for female cynomolgus monkeys is shown in FIG. 26B, bottom panel.
Figure 26A:
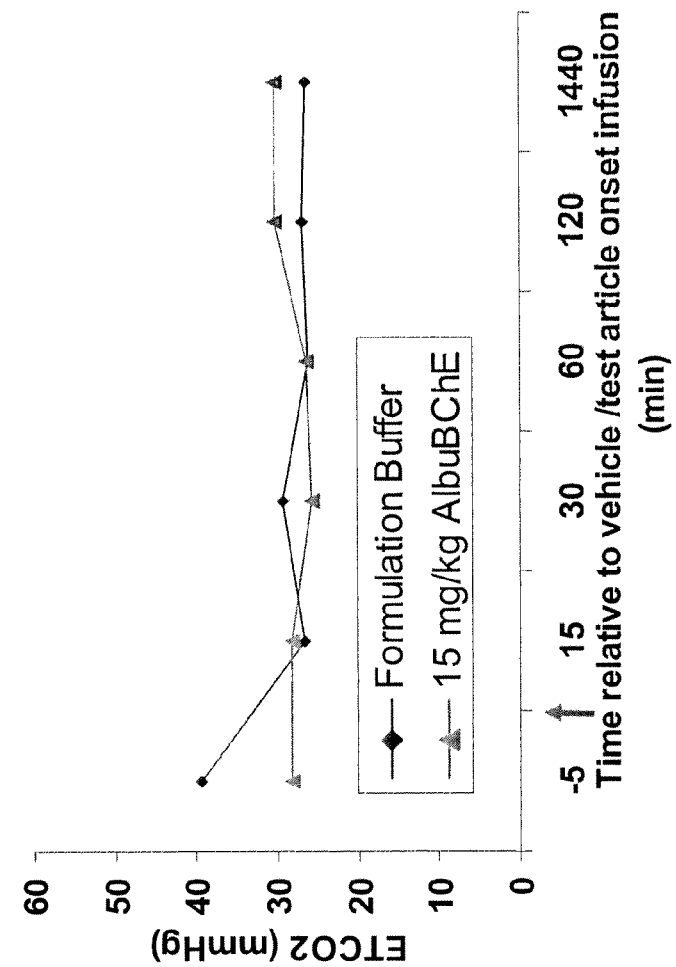

In spite of the limited number of time points and animals, an attempt was made to characterize AlbuBChE PK/PD relationship in male Squirrel monkeys. PK and PD data used in the analysis are shown in Table 20. The individual data and the fit resulting from the direct Inhibitory Effect $E_{max}$ model are shown in FIG. 17. The data clearly shows the inverse relationship between AlbuBChE serum concentration and cocaine levels. AlbuBChE serum concentration that may result in 50% decrease in cocaine concentration ($EC_{50}$) was estimated by the model to be ~400 ng/mL. $E_{max}$ was 213 ng/mL. Due to the limited data and the assumptions used in the analysis, parameter values from this PK/PD analysis need to be viewed as approximate estimates.

TABLE 20

AlbuBChE PK/PD analysis Squirrel Monkeys following a single IM administration of 5 mg/kg AlbuBChE dose. Cocaine was administered IV at a dose of 1 mg/kg in control animals (n = 2) or at 2, 72 and 96 hr post-AlbuBChE dose (n = 3).
PK parameters: AlbuBChE plasma concentrations at 24[#], 72 and 96 hr post-AlbuBChE dose
PD parameter: cocaine plasma concentration at 5 min post-cocaine dose.

| MKY ID | Time Post-AlbuBChE Dose (hr) | PK AlbuBChE (ng/mL) | PD Cocaine concentration at 5 min post-cocaine dose (ng/mL) |
|---|---|---|---|
| 548 (Control) | 2 | 0 | 185 |
| 27B (Control) | 2 | 0 | 239 |

TABLE 20-continued

AlbuBChE PK/PD analysis Squirrel Monkeys following a single
IM administration of 5 mg/kg AlbuBChE dose. Cocaine was
administered IV at a dose of 1 mg/kg in control animals (n = 2)
or at 2, 72 and 96 hr post-AlbuBChE dose (n = 3).
PK parameters: AlbuBChE plasma concentrations at
24[#], 72 and 96 hr post-AlbuBChE dose
PD parameter: cocaine plasma concentration at 5 min post-cocaine dose.

| MKY ID | Time Post-AlbuBChE Dose (hr) | PK AlbuBChE (ng/mL) | PD Cocaine concentration at 5 min post-cocaine dose (ng/mL) |
|---|---|---|---|
| 547 | 2 | 2340.2 | 0.575 |
| | 72 | 436.9 | 41.3 |
| | 96 | 247.5 | 97.9 |
| 3434 | 2 | 2296.7 | 20.0 |
| | 72 | 517.7 | 176 |
| | 96 | 247.5 | 191 |
| 53B | 2 | 2036.7 | 22.4 |
| | 72 | 433.7 | 104 |
| | 96 | 233.5 | 112 |

[#]Due to the fact that AlbuBChE concentration was not measured at 2 hr post-AlbuBChE dose, the 1st time sample collected was used in the analysis (24 hr post-AlbuBChE dose) with the assumptions that AlbuBChE concentration at 24 hr post AlbuBChE dose may reflect AlbuBChE conc. at 2 hr post AlbuBChE dose.

Conclusions

AlbuBChE pharmacokinetic profile was characterized in three male Squirrel monkeys following a single IM 5 mg/kg AlbuBChE dose. Extent of variability in exposure was minimal (~7%). AlbuBChE terminal elimination t½ was estimated to range from 45.5 to 65.5 hr.

Cocaine was administered IV at a dose of 1 mg/kg in control animals (n=2) or at 2, 72 and 96 hr post-AlbuBChE dose (n=3). AlbuBChE caused a decrease in cocaine exposure. The effect was most pronounced at 2 hr post-AlbuBChE dose (7% of control). Cocaine exposure was ~60% of control at 96 hr post-AlbuBChE dose.

Consistent with AlbuBChE mechanism of action, exposure to the cocaine metabolite ecgonine methyl ester increased ~40 fold at 2 hr post-AlbuBChE administration and decreased as a function of time post-AlbuBChE dose.

AlbuBChE effect was less pronounced on the cocaine metabolite, benzoylecgonine.

PK/PD relationship in Squirrel monkeys appears to indicate an inverse relationship between AlbuBChE serum concentration and cocaine levels. AlbuBChE serum concentration that may result in 50% decrease in cocaine concentration ($EC_{50}$) was estimated by the direct Inhibitory Effect $E_{max}$ model model to be ~400 ng/mL.

Due to the limited data and the assumptions used in the analysis, parameter values from this PK/PD analysis need to be viewed as approximate estimates.

EXAMPLE 3

AlbuBChE: A Cardiovascular Safety Pharmacology Study in Cynomolgus Monkeys with or without Administration of Cocaine Objective To evaluate the cardiovascular and respiratory safety of AlbuBChE administered by the intramuscular (IM) route in 3 male and 3 female cynomolgus monkeys. In addition, the effect of cocaine (administered by the intravenous (IV) route), AlbuBChE and their combination on cardiovascular safety was evaluated in another group of 3 male and 3 female cynomolgus monkeys.

Study Design

Prior to the start of the study, the monkeys were surgically instrumented with telemetry transmitters and vascular access ports. The following CV parameters were monitored: systolic pressure, diastolic pressure, mean arterial blood pressure, mean heart rate and mean rate-pressure product. Body temperatures changes were also monitored.

Study Group 1 (3 males and 3 females), served as a control group for testing the effect of AlbuBChE alone compared to its vehicle. Monkeys were administered (IM) with the control article AlbuBChE formulation buffer on Study Days (SDs) 1 and 4. Three hours post formulation buffer administration respiratory and cardiovascular (CV) parameters were recorded, respectively.

A single IM dose of the test article (AlbuBChE at 15 mg/kg) was administered on SD 8 and 11. Three hours after AlbuBChE dosing (corresponding to Tmax of AlbuBChE) CV and respiratory parameters were monitored, respectively.

The effect of pretreatment with AlbuBChE prior to cocaine dose on CV parameters was tested on the second group (Group 2) of animals (3 males and 3 females). First baseline CV parameters were recorded on SD 15 after an IM administration of AlbuBChE formulation buffer followed by a single IV administration of saline (cocaine vehicle), 3 hours later. The effect of cocaine on CV parameters was measured on SD 18, on which the animals received a single IM injection of AlbuBChE formulation buffer followed by a single IV dose of cocaine (1 mg/kg, IV), 3 hours later.

The effect of pretreatment with AlbuBChE on cocaine-induced changes in CV parameters was monitored on SD 22. CV parameters were recorded subsequent to a single IM dose of AlbuBChE (15 mg/kg) followed by a single IV dose of cocaine (1 mg/kg), 3 hours later (see Table 21).

All animals were observed at least twice a day for morbidity, mortality, injury, and availability of food and water. The physiological responses to test article administration, including blood pressure, heart rate, body temperature, and the electrocardiograph (ECG), were monitored.

TABLE 21

Group Designation and Dosage Levels

| Study Group | Study Day | Treatment | Test Article or Interaction Article Dose Level (mg/kg) | Test Article or Interaction Article Dose Conc. (mg/ml) | Number of Animals Male | Number of Animals Female |
|---|---|---|---|---|---|---|
| 1 | 1 | Formulation Buffer-CV | 0 | 0 | 3 | 3 |
| | 4 | Formulation Buffer-Respiration | 0 | 0 | | |
| | 8 | AlbuBChE-CV | 15 | 30 | | |
| | 11 | AlbuBChE-Respiration | 15 | 30 | | |
| 2 | 15 | Formulation Buffer-CV | 0 | 0 | 3 | 3 |
| | | Saline-CV | 0 | 0 | | |
| | 18 | Formulation Buffer-CV | 0 | 0 | | |
| | | Cocaine-CV | 1 | 5 | | |
| | 22 | AlbuBChE-CV | 15 | 30 | | |
| | | Cocaine-CV | 1 | 5 | | |

Results

All animals survived to study termination.

Study Group 1

AlbuBChE at 15 mg/kg (IM)) did not produce any significant changes in the recorded CV parameters, nor in body temperature compared to baseline values determined with AlbuBChE formulation buffer, as shown in FIGS. 18-26.

Study Group 2

Figure 27:
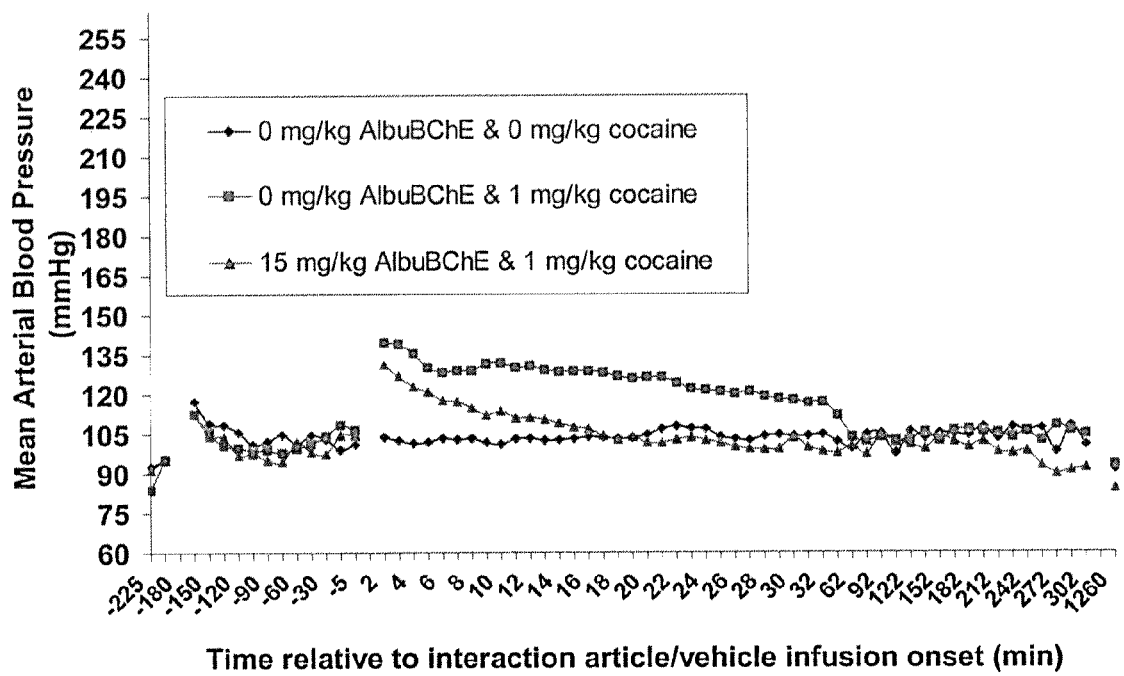
FIG. 27 shows mean arterial blood pressure vs. time in cynomolgus monkeys following a cocaine dose of 1 mg/kg administered IV three hours post 15 mg/kg AlbuBChE dose. Cocaine dose was administered at t=0.
Figure 28:
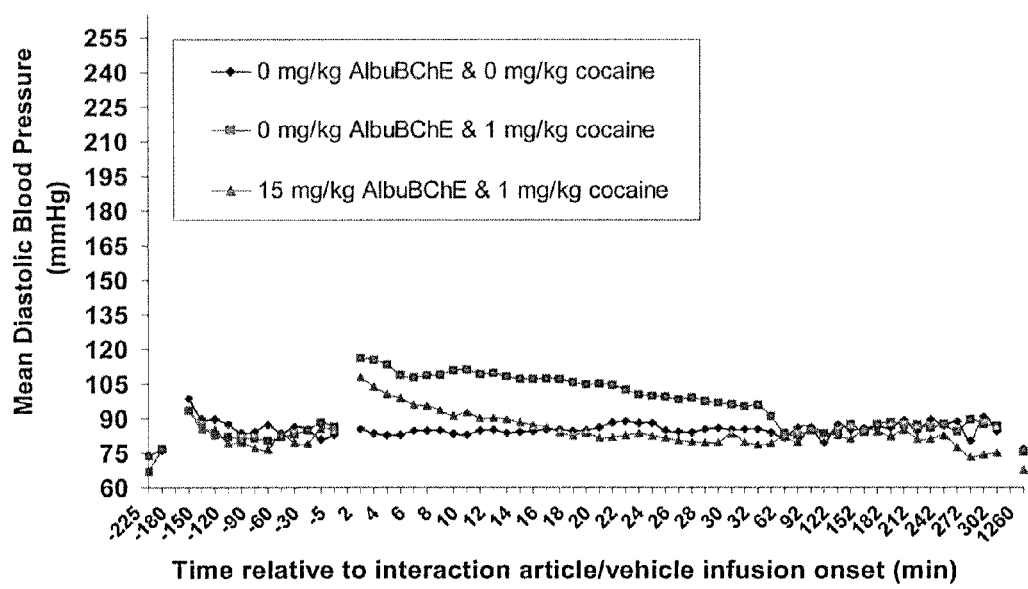
FIG. 28 shows mean diastolic blood pressure vs. time in cynomolgus monkeys following a cocaine dose of 1 mg/kg administered IV three hours post 15 mg/kg AlbuBChE dose. Cocaine dose was administered at t=0.
Figure 29:
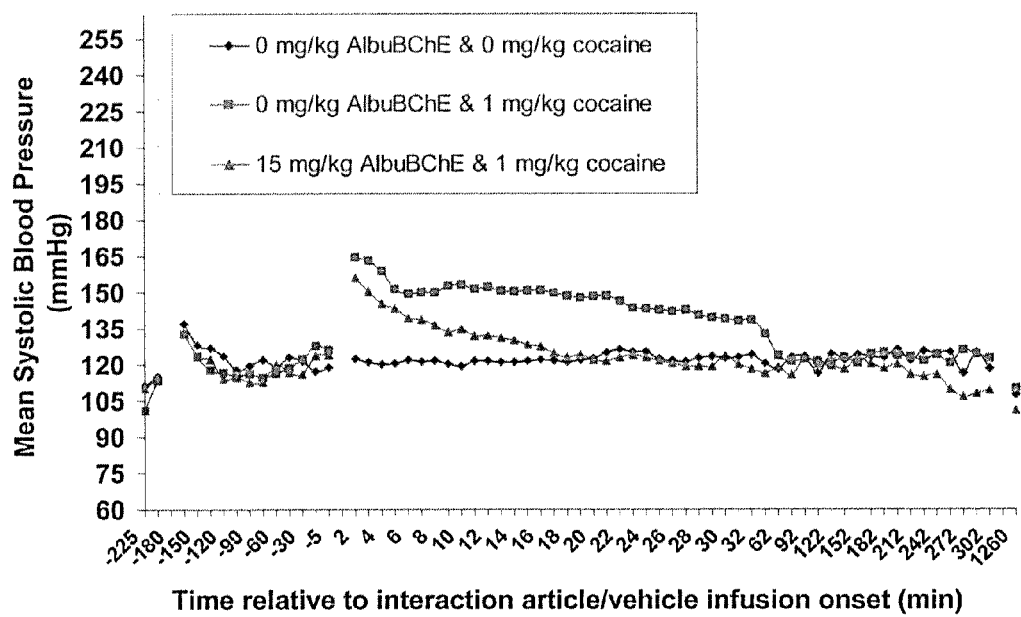
FIG. 29 shows mean systolic blood pressure vs. time in cynomolgus monkeys following a cocaine dose of 1 mg/kg administered IV three hours post 15 mg/kg AlbuBChE dose. Cocaine dose was administered at t=0.

Within two minutes post cocaine (1.0 mg/kg, IV) administration mean arterial blood pressure (MAP) was increased by about 35 mmHg above baseline value of 105 mmHg. Pre-treatment with 15 mg/kg AlbuBChE prior to cocaine dose showed that not only was the maximum blood pressure was decreased by AlbuBChE but the time to reversal of the effect was also truncated by 4.5 fold (17 minutes upon pretreatment with AlbuBChE prior to cocaine dose compared to 77 minutes when cocaine was given alone), as shown in FIG. 27.

Figure 30:
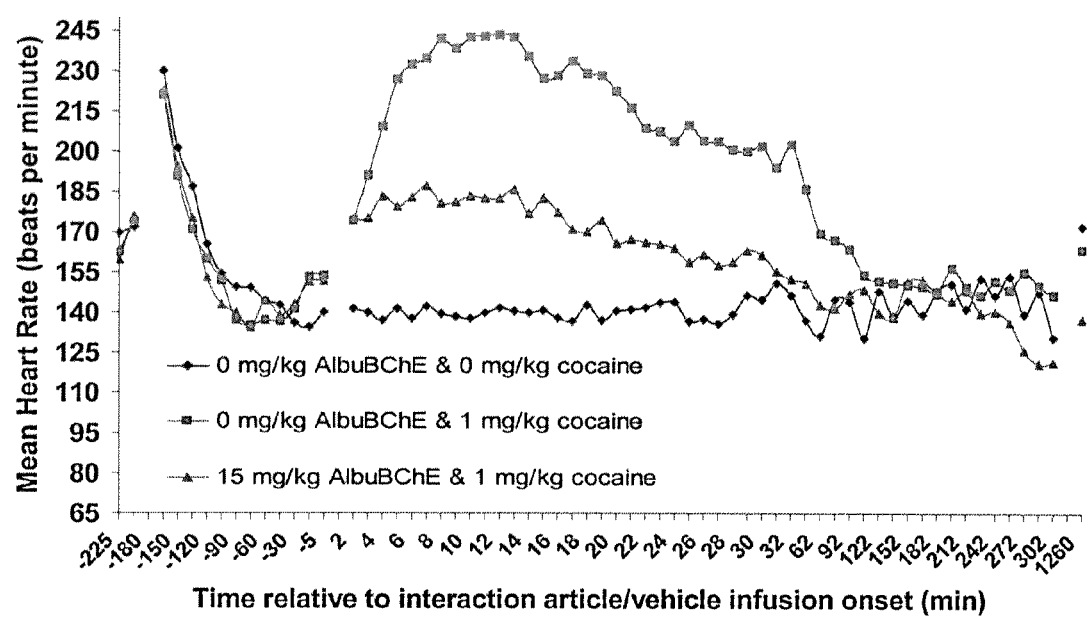
FIG. 30 shows mean heart rate vs. time in cynomolgus monkeys following a cocaine dose of 1 mg/kg administered IV three hours post 15 mg/kg AlbuBChE dose. Cocaine dose was administered at t=0.
Figure 31:
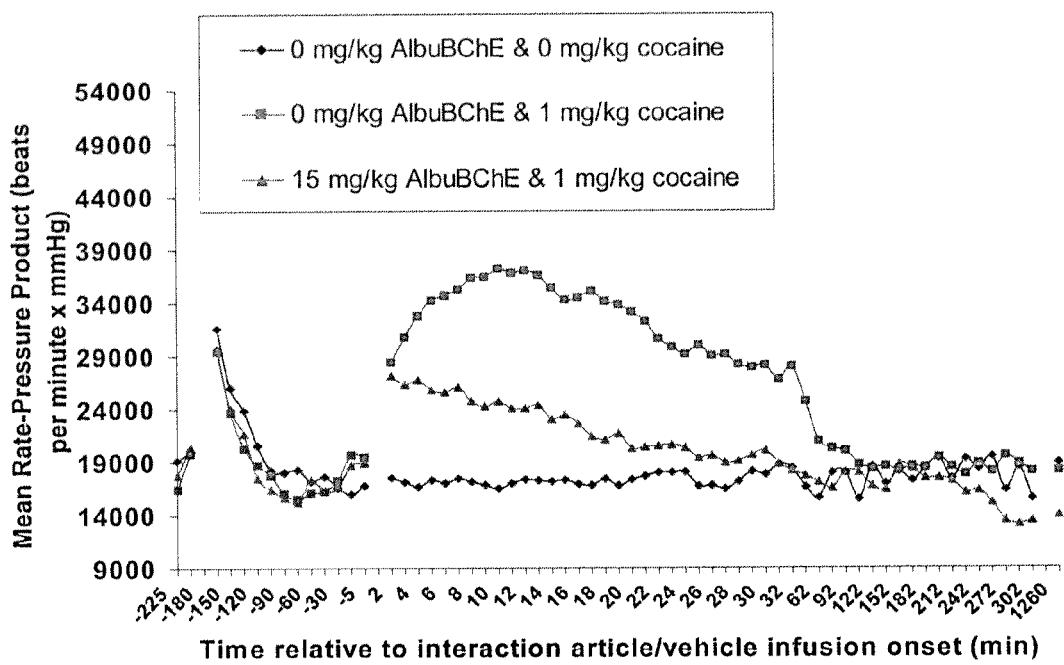
FIG. 31 shows mean rate pressure product vs. time in cynomolgus monkeys following a cocaine dose of 1 mg/kg administered IV three hours post 15 mg/kg AlbuBChE dose. Cocaine dose was administered at t=0.

Administration of cocaine (1.0 mg/kg, IV) elicited a rapid increase in heart rate from a baseline value of 140 beats/min reaching a peak value of 240 beats/min (70% increase) within about 3 minutes. This cocaine-induced elevation in heart rate was sustained for about 15 min dissipating gradually and returning to baseline value 2 hours after cocaine administration. Pre-treatment with AlbuBChE blunted cocaine-induced rise in heart rate showing a rapid but moderate increase of 30% to a peak value of 182 beats/min within about 3 minutes. This mild increase in heart rate was reversed completely returning to baseline value already 30 minutes after cocaine dose, as shown in FIG. 30.

Figure 32:
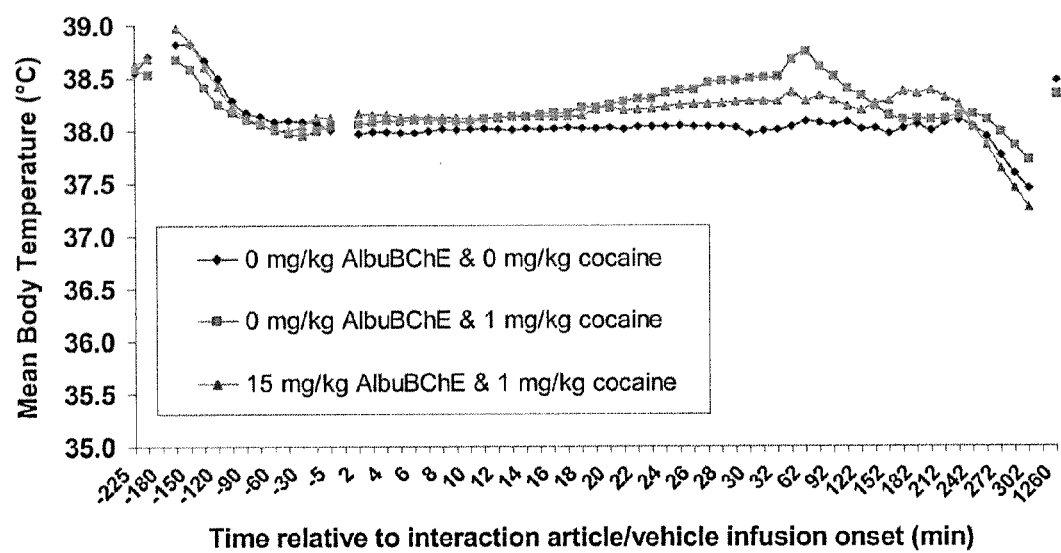
FIG. 32 shows mean body temperature vs. time in cynomolgus monkeys following a cocaine dose of 1 mg/kg administered IV three hours post 15 mg/kg AlbuBChE dose. Cocaine dose was administered at t=0.

Administration of cocaine (1.0 mg/kg, IV) resulted in a mild and step wise increase in body temperature with a peak value of 38.7° C. at 45 minutes post-dose compared to base line temperature of 38° C. Pre-treatment with AlbuBChE (15 mg/kg, IM) prior to cocaine dose caused only a subtle increase in body temperature to a value of 38.3° C., as shown in FIG. 32.

EXAMPLE 4

AlbuBChE: A Cocaine Self-Administration and Reinstatement of Cocaine Self-Administration Study in Squirrel Monkeys Methods Subjects Adult male squirrel monkeys (*Saimiri sciureus*) weighing 0.8 to 1.2 kg were used as subjects. All monkeys were individually housed in a humidity and temperature controlled room and had free access to water. The monkeys were fed following any experimental procedures an amount of food (Lab Diet 5045, PMI Nutrition International, Richmond, Ind.; Banana Softies, Bio-Serv, Frenchtown, N.J.) determined to maintain a stable weight. Fresh fruit, vegetables and environmental enrichment were also provided daily. The animal care facilities were fully accredited by AAALAC and all experiments were approved by the NIDA Intramural Research Program Animal Care and Use Committee.

Cocaine Self-Administration

Three monkeys were trained to self-administer 30 µg/kg/inj i.v. cocaine. Details of the self-administration training procedure can be found elsewhere (Justinova et al., 2003). In brief, the monkeys were placed in a seated position in a Plexiglas restraint chair. The chair was enclosed in a larger acoustical chamber. On the front wall of the restraint chair there was a response lever and stimulus lights. A green light signaled the beginning of the session. The monkeys were trained to make 10 responses (fixed-ratio, FR, 10) to receive an i.v. injection of cocaine. The injection of cocaine was accompanied by the green light, turning off and a yellow stimulus light being presented for 2 sec. Following each cocaine injection there was also a 60-sec timeout. At the end of the timeout, the green light was turned on. Sessions lasted for 1 hour. Occasionally, saline was substituted for cocaine. Following the establishment of stable cocaine self-administration and reliable extinction of responding following saline substitution, AlbuBChE (5 mg/kg, i.m.) or its vehicle (i.m.) were given 2 hours prior to a self-administration session. Self-administration responding was then measured for 5 consecutive days. Following each drug test or saline substitution, responding for 30 µg/kg/inj cocaine was reestablished for at least 5 days. Following reinstatement testing (see below), the dose of cocaine available for self-administration was lowered to 10 µg/kg/inj and the effect of AlbuBChE (5 mg/kg, i.m.) was again determined.

Reinstatement of Cocaine Self-Administration

Saline was substituted for cocaine in monkeys that were reliably self-administering 30 µg/kg/inj i.v. cocaine. Responding rapidly decreased and remained at that low level over a number of days. The vehicle of AlbuBChE was then given 2 hrs before cocaine (0.3 mg/kg, i.v.), which was given 5 min prior to a session where saline was available for self-administration to determine whether cocaine would reinstate self-administration responding. The same dose of cocaine was also given prior to saline self-administration sessions 48 and 96 hours later. Subsequently, AlbuBChE (5 mg/kg, i.m.) was given 2 hours prior to a second sequence of 3 reinstatement tests with 0.3 mg/kg i.v. cocaine. Following these tests, the monkeys were returned to baseline where 30 µg/kg/inj cocaine was available for self-administration. Subsequently, saline was again substituted for cocaine and a second series of reinstatement tests were conducted in a similar manner except that 0.1 mg/kg i.v. cocaine was given prior to reinstatement sessions.

Drugs

AlbuBChE was supplied by TEVA Pharmaceutical (Netanya, Israel) in a frozen solution at a concentration of 30 mg/ml. Once thawed the solution was diluted to 15 mg/ml with vehicle and then given to the monkeys in a volume of 0.33 ml/kg. Cocaine (NIDA, Baltimore, Md.) was prepared in sterile saline and given in a volume of 0.2 ml for self-administration. When given as a pretreatment for the reinstatement studies, cocaine was given in a volume of 0.3 ml/kg.

Data Analysis

The blood level data were analyzed separately for each metabolite and time point (5 or 30 min). A one-way analysis-of-variance (ANOVA) was performed with follow-up Dunnett tests using the results of monkeys treated with vehicle as the control. The self-administration data were analyzed separately for response rate or injections following either vehicle treatment or AlbuBChE treatment. Control data were included in the analysis by taking the average of the last 3 days for the immediately preceding baseline condition. A within subjects ANOVA was then performed with follow-up tests contrasting days following vehicle or AlbuBChE with the control. For the reinstatement tests, a two-way ANOVA was performed for both response rate and injections, with time post vehicle or AlbuBChE as the within-subjects factor and pretreatment (vehicle or AlbuBChE) as the between subjects factor. Follow-up contrast compared vehicle and AlbuBChE at each time point.

Results

Figure 33:
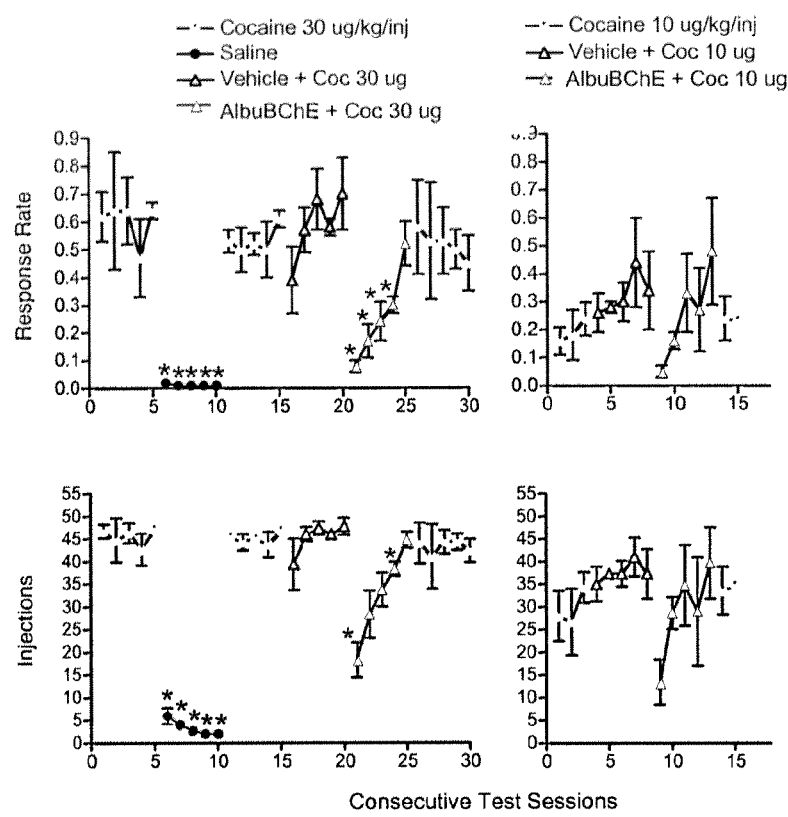
FIG. 33 shows squirrel monkey response rate (top panels) and number of injections (bottom panels) during self administration sessions over consecutive days where either cocaine or saline was available for self-administration. Responding was tracked for five days following vehicle or AlbuBChE administration (5 mg/kg).

In monkeys self-administering 30 µg/kg/inj cocaine, AlbuBChE reduced self-administration. The panels of FIG. 33 show response rate (top panel) and injections (bottom panel) over consecutive days. The first five days show baseline responding. Saline was then substituted for cocaine and both rate ($F_{5,10}=37.0$, $p<0.001$) and injections ($F_{5,10}=188.7$, $p<0.001$) were significantly reduced for the 5 days of substitution when compared to the average of the last 3 days of the preceding baseline period. Following a 5 day return to baseline, monkeys were treated with vehicle and given 5 days of self-administration training. When compared to the average of the last 3 days of the preceding baseline period, vehicle treatment had no effect on injections ($F_{5,10}=2.6$, $p=0.10$). An overall effect of days was observed for response rate ($F_{5,10}=4.6$, $p<0.05$), however follow-up contrasts failed to reveal any significant change in responding from control on any of the days following vehicle treatment. Following vehicle treatment, monkeys were given 5 mg/kg AlbuBChE and cocaine self-administration was tracked for 5 days. Significant changes from the average of the last 3 days of the previous baseline were observed for both response rate ($F_{5,10}=4.6$, $p<0.05$) and injections ($F_{5,10}=14.1$, $p<0.001$). Follow-up contrast revealed that response rate was different from control on days 1-4 following treatment and injections were significantly different from control on day 1 and 4 following treatment.

Following reinstatement testing (see below), monkeys were returned to self-administration at a lower cocaine dose (10 μg/kg/inj). Decreasing the maintenance dose decreased rate of responding and number of injections (FIG. 33 right panels). Following baseline stability, monkeys were given a vehicle injection and self-administration continued for 5 days. Neither response rate nor injections significantly changed following vehicle injection compared to the average of the last 3 days on baseline. AlbuBChE (5 mg/kg) was then given and cocaine self-administration continued for an additional 5 days. Both response rate and injections were decreased 2 hrs following the AlbuBChE injection, but these effects failed to reach significance.

Figure 34:
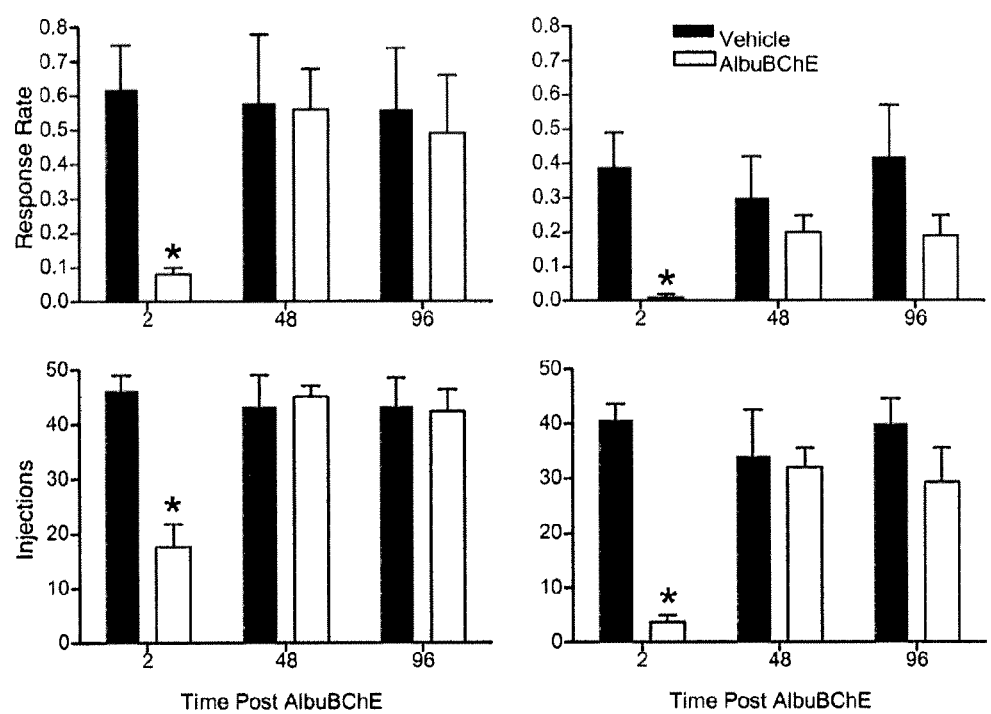
FIG. 34 shows levels of reinstatement of cocaine self-administration following administration of AlbuBChE or AlbuBChE vehicle. The AlbuBChE or vehicle was given i.v. Two, 48 and 96 hrs later 0.3 mg/kg cocaine i.v. (left panels) or 0.1 mg/kg cocaine i.v. (right panels) was given 5 min before a saline substitution session.

In monkeys that were responding for 30 μg/kg/inj cocaine, substituting saline for cocaine lead to a rapid decrease in responding. The AlbuBChE vehicle was then given i.m. Two, 48 and 96 hrs later 0.3 mg/kg cocaine i.v. was given 5 min before a saline substitution session. The administration of cocaine led to a reinstatement of cocaine self-administration responding as shown in the black bars in the left panels of FIG. 34. When 5 mg/kg AlbuBChE was given i.m., and 2 hrs, 48 hrs and 96 hrs later 0.3 mg/kg cocaine i.v. was given immediately before a saline substitution session, reinstatement of responding was significantly blocked at the 2 hr time point for both response rate ($F_{1,4}=16.9$, $p<0.05$) and injections ($F_{1,4}=34.9$, $p<0.001$). Monkeys were subsequently tested in an identical manner with 0.1 mg/kg cocaine as the reinstatement dose. While reinstatement to the lower cocaine dose was more variable, a similar pattern of results was observed with the effect of 5 mg/kg AlbuBChE again significant at 2 hrs for both responses ($F_{1,4}=15.2$, $p<0.05$) and injections ($F_{1,4}=129.7$, $p<0.001$).

Figure 35:
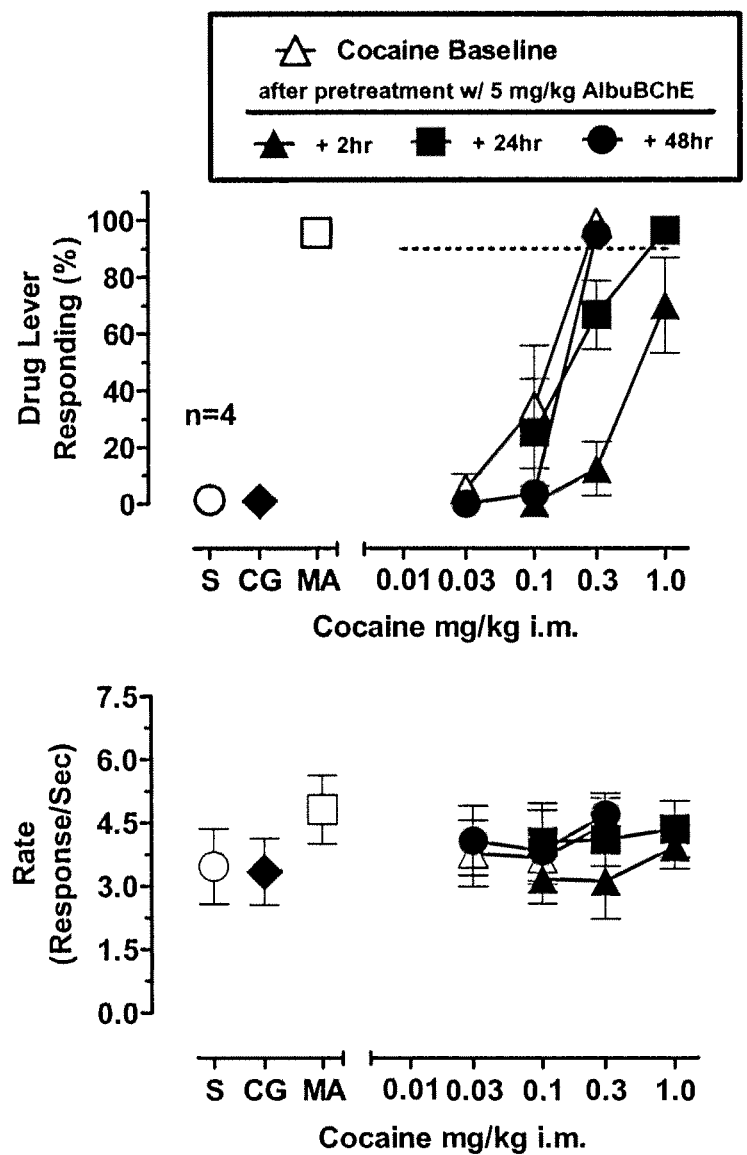
FIG. 35 shows the modulation of cocaine's discriminative-stimulus effects in methamphetamine trained subjects by AlbuBChE.
Figure 36:
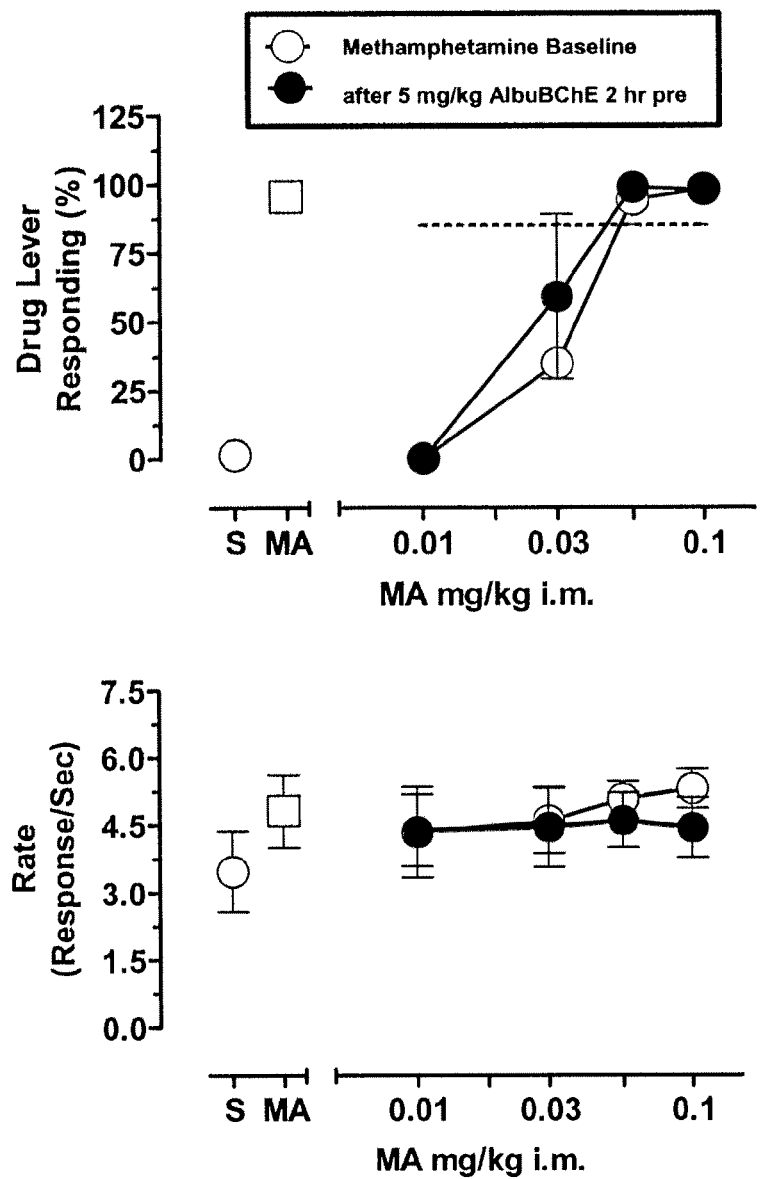
FIG. 36 shows methamphetamine's discriminative-stimulus effects in methamphetamine trained subjects after AlbuBChE administration.
Figure 37:
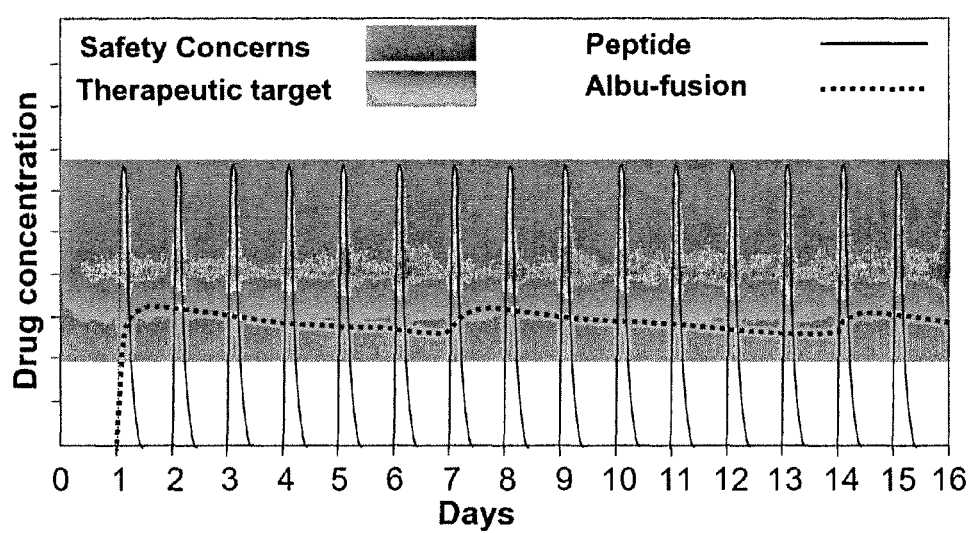
FIG. 37 shows the relative serum concentration of an albumin fusion compared to a non-fusion peptide where the albumin fusion is dosed once-weekly and the non-fusion peptide is dosed daily.
Figure 38:
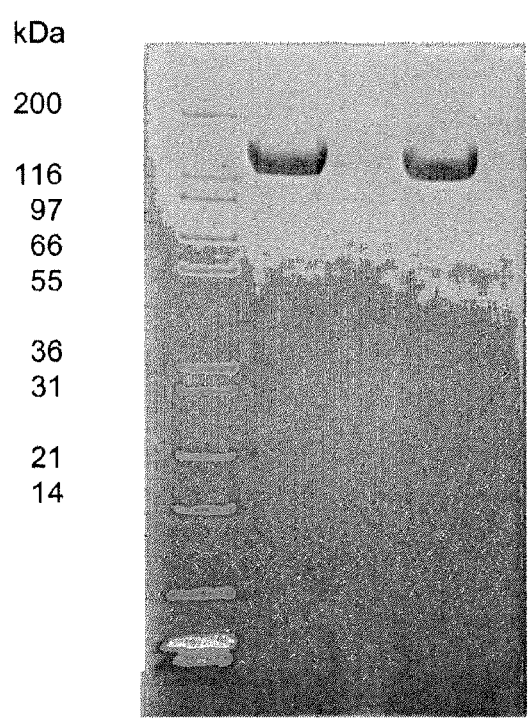
FIG. 38 shows a SDS-PAGE of AlbuBChE purified from CHO cells. Lane 1 is a molecular weight marker, and lanes 2 and 4 show purified AlbuBChE under reducing and non-reducing conditions, respectively.
Figure 39:
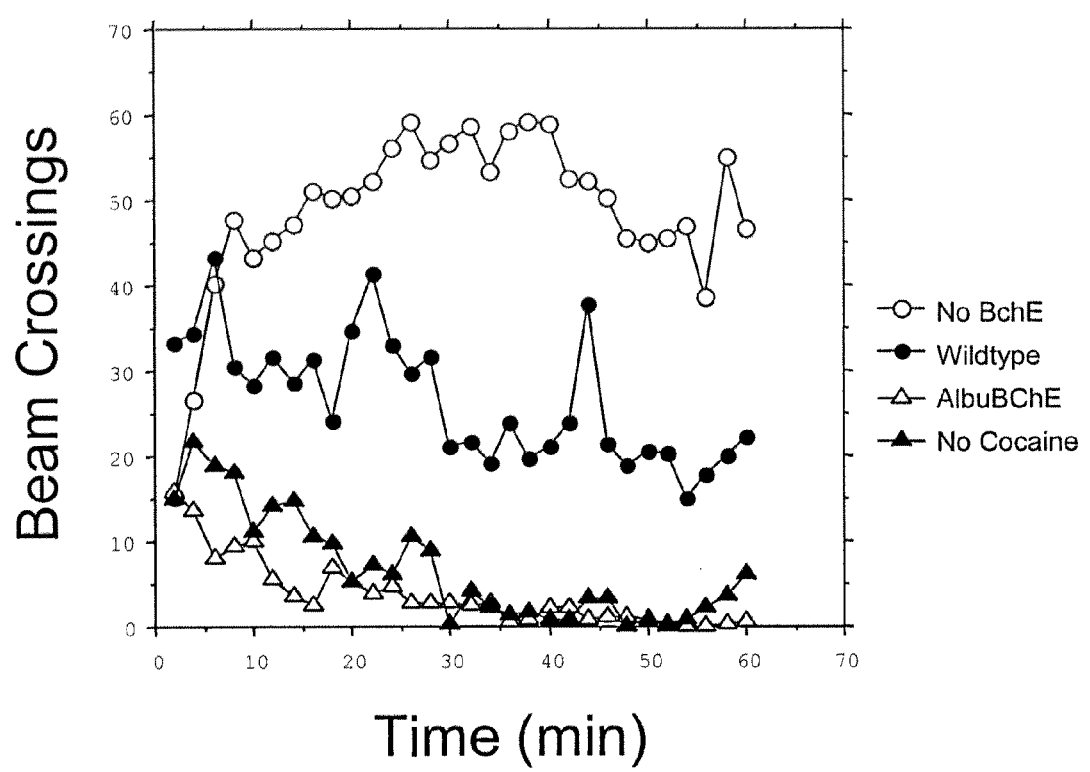
FIG. 39 shows the number of beam crossings vs. time in rats treated with wild-type BChE or Albu-CocH prior to a cocaine dose, rats given a cocaine dose alone, and rats given neither cocaine nor BChE. Locomotor activity was assessed by detecting infrared beam breaks as described in Brimijoin et al.
Figure 40:
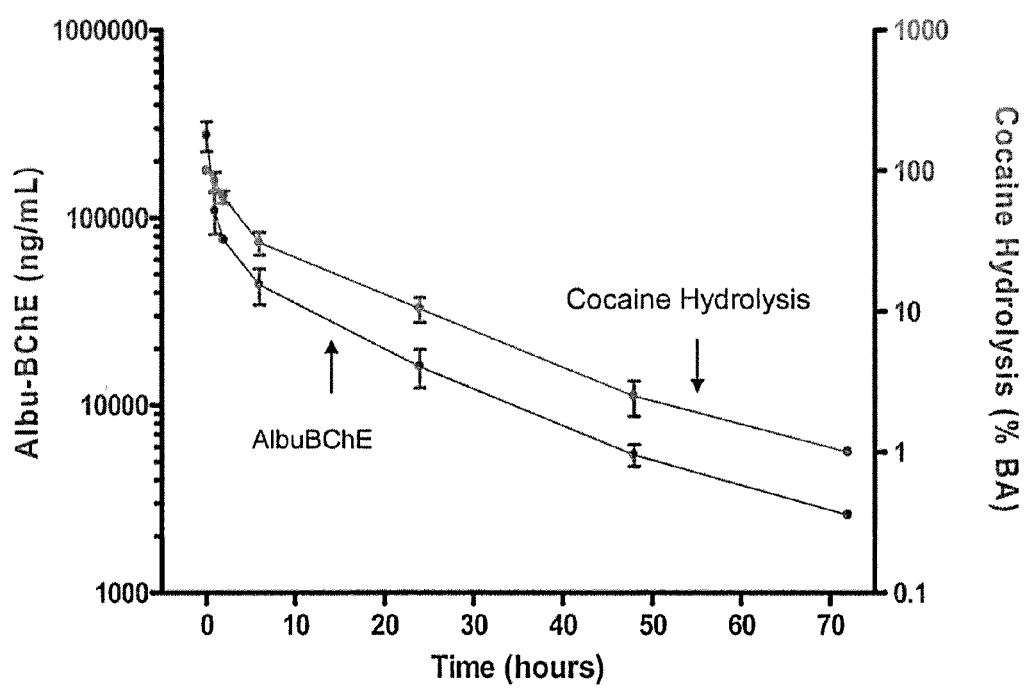
FIG. 40 shows the concentration of AlbuBChE vs. time in mice following a dose of AlbuBChE and also shows cocaine hydrolysis (represented as the percentage of cocaine converted to benzoic acid (% BA) within 60 minutes of cocaine administration) vs. time post AlbuBChE dose.
Figure 41:
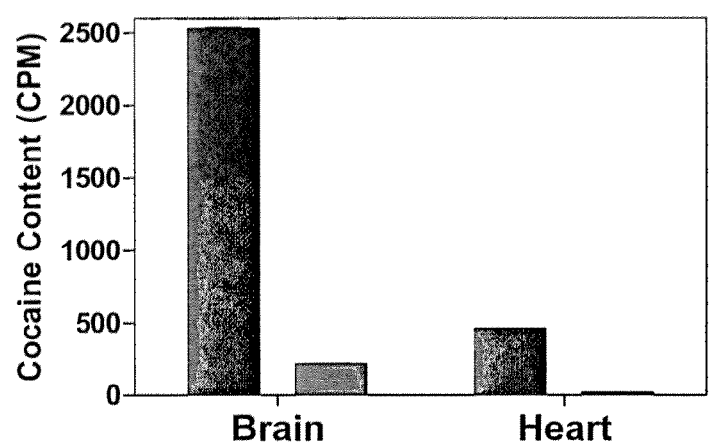
FIG. 41 shows the cocaine content in brain and heart collected from rats (n=6) given an AlbuBChE (3 mg/kg) dose or saline, through the tail vein, followed ten minutes later by 30 μCi 3H-cocaine (3.5 mg/kg), also through the tail vein. Brains and hearts were collected 10 minutes post 3H-cocaine dose. Left to right, control data is bars 1 and 3, while AlbuBChE data is bars 2 and 4.
Figure 42:
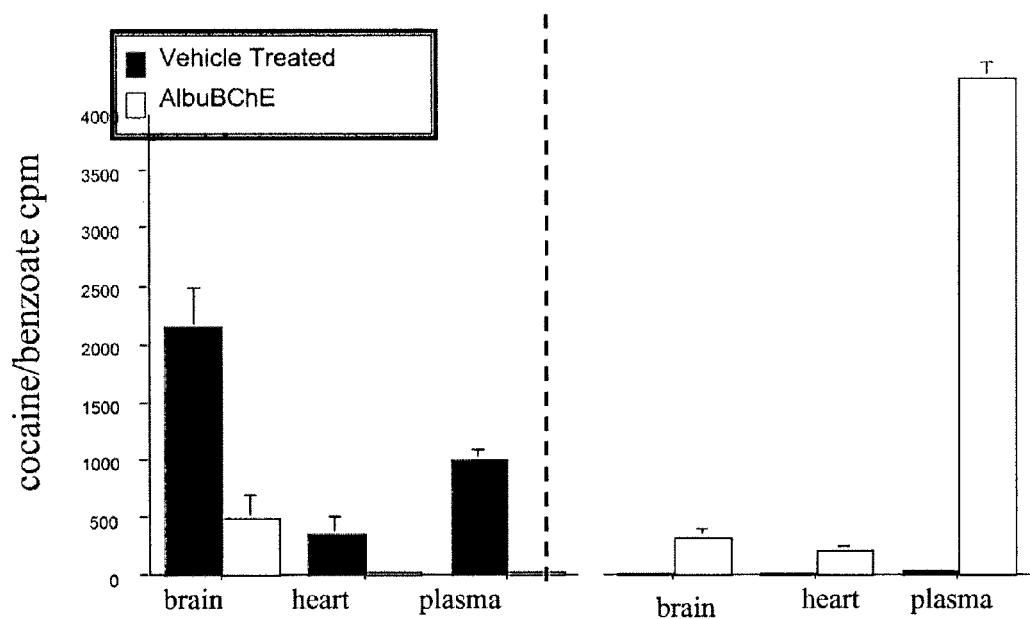
FIG. 42 shows cocaine (left plot) and benzoate levels (right plot) in brain, heart and plasma collected from rats given a 3 mg/kg AlbuBChE dose or saline 10 minutes prior to a 30 μCi 3H-cocaine dose (3.5 mg/kg). Brain, heart and plasma were collected 10 minutes post cocaine dose.
Figure 43:
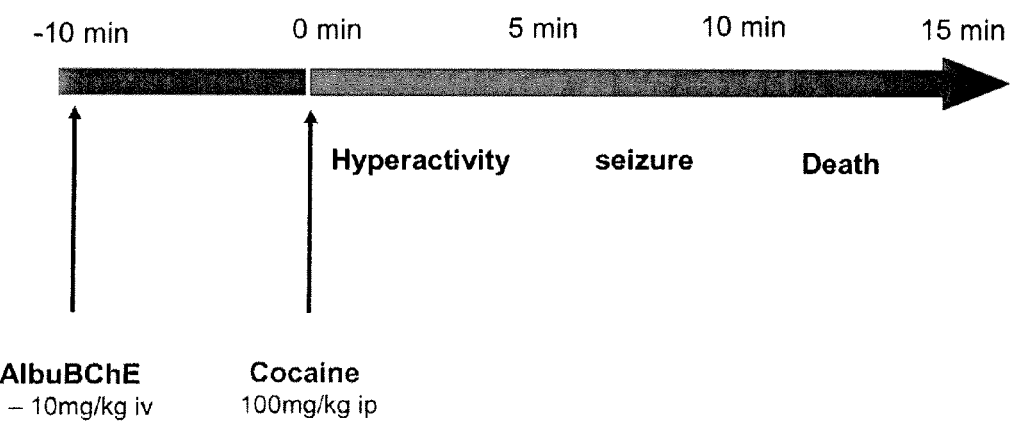
FIG. 43 shows the experimental design of a study examining the ability of AlbuBChE to protect from lethal overdose.
Figure 44:
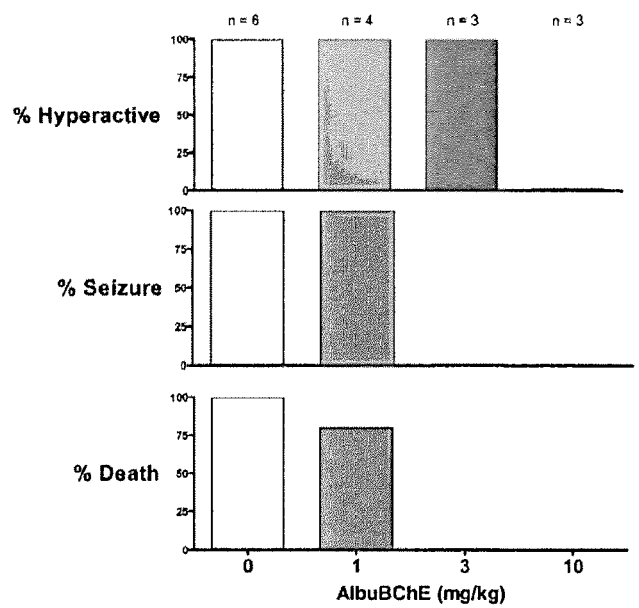
FIG. 44 shows the percentage of rats exhibiting hyperactivity, seizures, and death in response to a dose of 100 mg/kg cocaine given ten minutes after a dose of 0, 1, 3, or mg/kg AlbuBChE.
Figure 45:
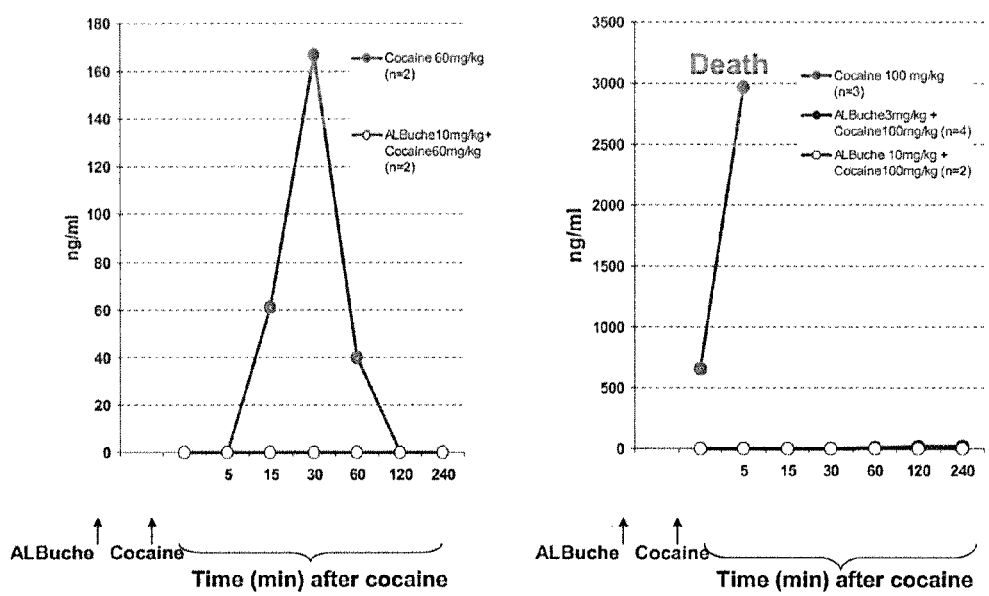
FIG. 45 shows the concentration of cocaine vs. time in Sprague Dawley rats given an IV dose of AlbuBChE at 0, 2, and 10 mg/kg followed five minutes later by an IP dose of cocaine at 60 or 100 mg/kg.
Figure 46:
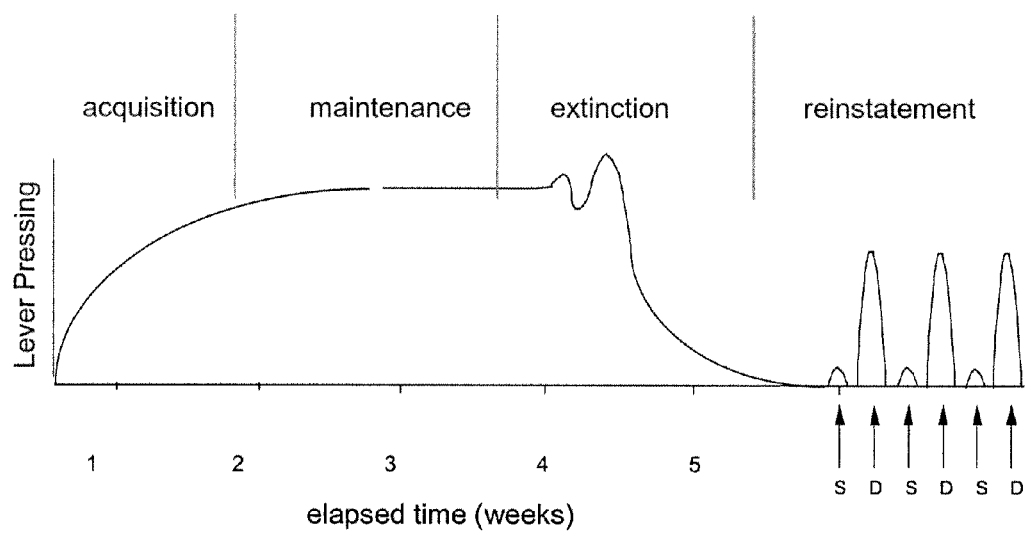
FIG. 46 shows a behavioral model of addiction and relapse. "S" and "D" represent saline and the drug cocaine, respectively. Animals are trained to emit a lever press for a cocaine infusion. After stabilization (maintenance), saline is substituted for cocaine and the behavior is allowed to extinguish. In the subsequent reinstatement phase, priming injections of cocaine are given, alternating with saline.
Figure 47:
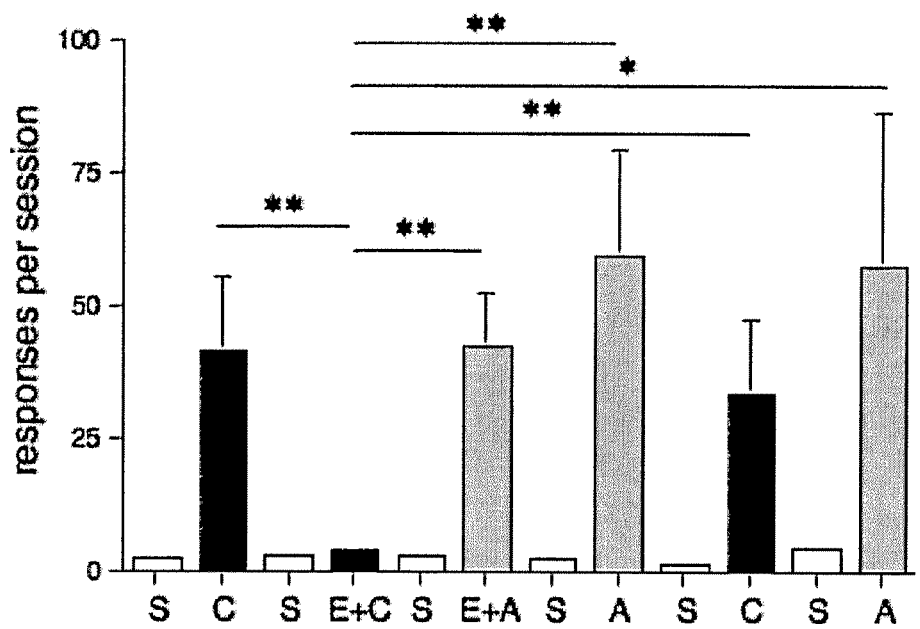
FIG. 47 shows the selective blockade of cocaine-primed reinstatement of drug-seeking behavior resulting from AlbuBChE treatment. Rats that had previously self-administered cocaine and extinguished when cocaine was replaced with saline were primed with an IV injection of saline (S), cocaine (C, 10 mg/kg), or amphetamine (A, 2 mg/kg). AlbuBChE was administered IV (E, 2 mg/kg) two hours before the behavioral session.

In 4 monkeys that were trained to discriminate 0.6 mg/kg methamphetamine from saline, cocaine fully substituted for methamphetamine at a dose of 0.3 mg/kg (FIG. 35, top panel). When 5 mg/kg AlbuBChE was given 2 hrs prior to the determination of the cocaine dose-effect function, 0.3 mg/kg cocaine failed to generalize to the methamphetamine cue. Partial substitution (approximately 70%) was observed at a higher cocaine dose (1.0 mg/kg). Twenty-four hrs following AlbuBChE, the 0.3 mg/kg dose of cocaine still failed to completely generalize to the methamphetamine cue (approximately 70%), but 1.0 mg/kg now fully generalized to methamphetamine. By 48 hrs following AlbuBChE, the 0.3 mg/kg dose fully generalized to the methamphetamine cue. Pretreatment with AlbuBChE 2 hrs prior to the determination of the methamphetamine dose-effect function did not affect generalization of methamphetamine to the methamphetamine cue (FIG. 36, top panel). Pretreatment with AlbuBChE did not affect the rate of responding under either treatment condition (FIGS. 35 and 36, bottom panels).

The monkeys trained to self-administer cocaine and also tested on the reinstatement procedure received a total of 4 injections of AlbuBChE. Blood was taken for determination of AlbuBChE antibodies after the first, second and fourth AlbuBChE injections. Following the first 2 injections, antibody levels were below the level of detection (titer level of 20). Following the fourth injection, however, antibody levels appeared elevated. In 2 monkeys the antibody titer was slightly elevated over the limit of detection (21 and 43). For the third monkey, antibody levels were clearly elevated (643). The concentration of AlbuBChE in the blood for this monkey one week following the AlbuBChE injection was also reduced (27 ng/ml vs 55 and 53 ng/ml for the other 2 monkeys).

Discussion

The results of these studies clearly show that pretreatment with a modified form of BChE is effective in antagonizing the behavioral effects of cocaine in a non-human primate. This work extends previous work with this compound in rodents, where it was shown that AlbuBChE could antagonize the toxic effects of cocaine in rats and also block cocaine-induced reinstatement of cocaine self-administration (Brimijoin et al., 2008). Here, pretreatment with 5 mg/kg AlbuBChE reduced both response rate and injections in monkeys self-administering 30 μg/kg/inj cocaine. In these same monkeys tested for reinstatement of cocaine self-administration following self-administration extinction, 5 mg/kg AlbuBChE was capable of blocking reinstatement of responding by either 0.3 mg/kg or 0.1 mg/kg cocaine. When the dose available for self-administration was reduced to 10 μg/kg/inj, AlbuBChE again appeared to reduce the response rate and number of injections received, although these effects with 10 μg/kg/inj cocaine were more variable and failed to reach significance. Finally, the 5 mg/kg dose of AlbuBChE was also able to antagonize the generalization of cocaine to a methamphetamine discriminative stimulus, but this effect was specific to cocaine as AlbuBChE was not able to antagonize the discriminative stimulus effects of methamphetamine.

When tested against 30 μg/kg/inj cocaine self-administration, the effects of AlbuBChE were still evident 3 days later, although at a reduced effectiveness. On reinstatement and discrimination, however, the effects of AlbuBChE were not evident 4B hours following treatment. The half-life of AlbuBChE was shown to be around 56 hours and effects on cocaine metabolism were still evident 72 hours after AlbuBChE administration, so it might have been expected that some effect on these procedures would have been evident at 72 hours. A number of factors could contribute to this failure to see a reduction in reinstatement or cocaine generalization at 72 hrs. During self-administration smaller doses of cocaine are given over an extended period of time. In the other procedures a relatively larger dose of cocaine was administered as a bolus injection. It may be easier for AlbuBChE to metabolize the cocaine before it reaches the brain under the self-administration conditions than under the other conditions. When AlbuBChE metabolizes cocaine under self-administration, its effect is to institute extinction conditions. Behavioral recovery from extinction may also prolong the effects of AlbuBChE treatment on self-administration. In the reinstatement study, responding produced saline and the stimulus previous associated with reinforcement. When the monkeys reinstated responding following a cocaine injection, the monkeys still received saline for responding, but they also received the stimulus previously associated with cocaine. The presentation of this stimulus may also have facilitated continued responding under the reinstatement conditions (Spealman et al., 1999), masking some of the effect of AlbuBChE.

The effects of AlbuBChE were almost certainly related to its effects on the metabolism of cocaine. The administration of AlbuBChE decreased the amount of cocaine in the blood for at least 72 hours. The fact that EWE levels were also increased for at least 72 hours following AlbuBChE suggests that AlbuBChE was metabolizing cocaine similarly to native BChE (Jones, 1984). This time course for cocaine metabolism is similar to that seen for the self-administration experiment where the monkeys were reinforced with 30 µg/kg/inj cocaine. Further, AlbuBChE had no effect on response rate in the discrimination study, suggested that it does not produce a non-specific effect on operant responding independent of the presence of cocaine in the blood.

The observation of relatively high levels of AlbuBChE antibodies in one monkey following its fourth injection indicates that AlbuBChE might lose some of its effectiveness over multiple injections. While the results for that one particular monkey did not appear to be different from the other 2 monkeys tested, the observation of antibodies suggests that some of the AlbuBChE would be bound by antibodies which might decrease its ability to metabolize cocaine. Further work will be needed to determine how prevalent the antibody production is in primates and whether the levels of antibody observed are sufficient to decrease the effectiveness of AlbuBChE in metabolizing cocaine.

Cocaine continues to show up in both emergency room mentions and medical examiner reports in the DAWN surveys. As such, a drug that could counteract the toxic effects of cocaine may be useful adjunct to emergency room treatment for patients abusing cocaine. An advantage of using a drug that metabolizes cocaine is that it will be specific for cocaine and should have minimal side effects. However, it would be necessary to confirm that a patient is using cocaine as AlbuBChE would not be effective against toxicity produced by other drugs of abuse, such as the amphetamines, that might produce a similar spectrum of toxic effects.

In addition to treating the toxic effects of cocaine, AlbuBChE might also be useful as an adjunct to other treatments for cocaine abuse. A person with a sufficient blood level of AlbuBChE who takes cocaine would be expected to experience a reduced subjective effect of cocaine. In the context of the current study, this translates to less cocaine self-administration, reduced reinstatement of cocaine self-administration and the failure of cocaine to generalize to the methamphetamine discriminative stimulus. As relapse to cocaine abuse remains a problem in treatment, the reduced subjective effects of cocaine would be expected to reduce relapse. For someone undergoing treatment that does relapse to use, the presence of AlbuBChE in the blood would metabolize much of the cocaine and potentially reduce the likelihood of continued cocaine use. This would require an individual to continue taking AlbuBChE throughout the period of time that relapse would be expected. Therefore, it will be critical to determine how prevalent the development of antibodies to AlbuBChE is and how that might effect its ability to metabolize cocaine.

In conclusion, pretreatment of squirrel monkeys with AlbuBChE was able to reduce the amount of cocaine in the blood following a cocaine bolus treatment. Pretreatment with AlbuBChE was also able to reduce cocaine self-administration in monkeys that had been trained to self-administer 10 and 30 µg/kg/inj cocaine. AlbuBChE was able to block cocaine-induced reinstatement of cocaine self-administration for 2 different doses of cocaine. Finally, AlbuBChE was also able to antagonize the discriminative effects of cocaine in squirrel monkeys. The finding that AlbuBChE was able to antagonize the behavioral effects of cocaine in 3 different models of cocaine's behavioral effects suggests that it should be effective as a potential treatment of cocaine abuse.

EXAMPLE 5

A Double-Blind, Placebo-Controled, Single Ascending Dose of AlbuBChE Followed by Multiple Doses of Cocaine to Evaluate the Pharmacokinetic and Pharmacodynamic Parameters of Cocaine after AlbuBChE Administration in Cocaine Recreational Volunteers Objective To determine cocaine blood levels following multiple doses subsequent to AlbuBChE administration, and to determine the behavioral, psychological and safety effects of cocaine following multiple doses subsequent to AlbuBChE administration. To evaluate the pharmacokinetics, safety, and tolerability of AlbuBChE.

Study Design

This is a 5-arm, parallel-group, active and placebo-controlled, double blind, randomized study, to compare treatment with AlbuBChE with placebo as a negative control.

Forty (40) non-treatment seeking healthy adults who have used cocaine are randomly assigned to five (5) treatment groups. Each group will contain eight subjects.

Group A (low dose): Subjects receive a single, intramuscular injection of 50 mg of AlbuBChE.

Group B (intermediate dose): Subjects receive a single, intramuscular injection of 100 mg of AlbuBChE.

Group C (high-intermediate dose): Subjects receive a single, intramuscular injection of 150 mg of AlbuBChE.

Group D (high dose): Subjects receive a single, intramuscular injection of 300 mg of AlbuBChE.

Group E (negative control): Subjects receive a single, intramuscular injection of placebo.

The study is divided to 5 cohorts of 8 subjects per cohort with 2 to 3 days apart.

Inpatient Hospital Phase

Subjects remain resident in the clinic from the evening before Day 1 (check in; Day −1) until the morning of Day 11. Subjects return to the clinic for follow-up visit on Day 18±2.

Day −1: On the morning of day −1, a 40 mg intravenous dose of cocaine is administered.

Day 1: A single, intramuscular dose of AlbuBChE or placebo is administered.

Day 1, 4, 8 and 10: On Day 1, at AlbuBChE $C_{max}$ (3 hours post dose) and at the morning of days 4 (72 hours), 8 (168 hours) and 10 (216 hours) at the corresponding time of AlbuBChE/placebo administration, a 40 mg intravenous challenge dose of cocaine is administered.

Saline infusions are included (randomized with cocaine infusions, administered 2 hours apart) on each day of cocaine administration, and have the infusion type order single blinded.

Study Drug Administration

Planned AlbuBChE doses are as described above for groups A-E. Each subject receives a single dose of AlbuBChE or placebo by intramuscular (IM) injection. 40 mg of cocaine hydrochloride, prepared as a 1 mg/ml saline solution is injected into a forearm vein at the rate of 1 mg/second using a constant rate infusion pump.

Study Duration

The duration of the study (from screening until the End of Study (MOS) visit) for each subject is approximately 11 to 12 weeks.

Study Population

A total of Forty (40) male subjects aged 18-55 who are recreational cocaine users. Subjects who discontinue the study for any reason after dosing are not replaced.

Main Inclusion/Exclusion Criteria

Inclusion Criteria

1. Male volunteers aged 18-55 years, inclusive;
2. Body mass index (BMI) 18-33 kg/m$^2$ and weight of at least 50 kg;
3. Healthy, as determined by no clinically significant medical history, physical examination, electrocardiogram (ECG), vital signs and laboratory results at screening;
4. Currently use cocaine by smoking, intranasal or i.v. route; defined as at least once in a month prior to screening, 6 times in the past year and 20 times over lifetime. Current use is confirmed through a positive Urine Drug Test (UDS) prior to in-patient period (i.e. at screening or between screening and Day −1);
5. Able to understand the nature of the trial and any hazards of participating in it;
6. Able to communicate satisfactorily with the Investigator and to participate in, and comply with the requirements of the entire trial; and
7. Willingness to give written consent to participate, after reading the information and consent form and after having the opportunity to discuss the trial with the Investigator or his delegate and sign the Informed Consent.

Exclusion Criteria

1. Current or history of alcohol or drug dependence according to DSM-IV-TR (Diagnostic and Statistical Manual of Mental Disorders—last version) criteria (excluding nicotine and caffeine), or participation in rehabilitation program (except smoking cessation);
2. History of severe allergic or anaphylactic reactions;
3. Known allergy or hypersensitivity to natural or recombinant butyryl cholinesterase (BChE), human serum albumin (HSA) or any other component of the formulation;
4. History of any clinically significant (as determined by the Principal Investigator) cardiac, endocrine, haematological, hepatic, immunological, metabolic, urological, pulmonary, neurological, dermatological, psychiatric, renal, or other major disease;
5. History of any malignant disease;
6. Major trauma or surgery in the 2 months before screening or at any time between screening and check-in;
7. Acute infection within 2 weeks before screening or at any time between screening and check-in;
8. Clinically significant abnormal ECG findings at screening or check-in visits, as determined by the Principal Investigator;
9. Blood pressure outside the ranges 90-140 mmHg systolic or 45-90 mmHg diastolic (measured after a rest of at least 5 min) at screening or check-in. Blood pressure may be re-tested in the supine position at intervals of 5-10 min. The pressure elevation is considered sustained if either the systolic or the diastolic pressure exceeds the stated limits after three assessments, and thus the subject may not be randomized;
10. Heart rate <40 beats/min (measured after a rest of at least 5 min) at screening or check-in;
11. Known history of or a positive test result for human immunodeficiency virus (HIV) types 1 or 2 at screening;
12. Known history of, or a positive test result for hepatitis B surface antigen (HBsAg) or hepatitis C virus (HCV) at screening;
13. Use of prescription or over-the-counter (OTC) medication (other than paracetamol (acetaminophen), $\leqq 2$ g/day or ibuprofen, $\leqq 650$ mg/day), investigational drugs, vitamins, or herbal remedies, within 2 weeks before dosing or within 5 half-lives before dosing, whichever is longer;
14. Participation in another clinical trial of a new chemical entity or a prescription medicine within the 3 months before dosing or within 5 half-lives before dosing, whichever is longer;
15. Loss of >400 mL blood (e.g. as a blood donor) within 2 months before dosing, or received any blood, plasma, or platelet transfusions within 3 months before check-in, or who have planned donations during the study or within 3 months after the study;
16. Subject consumes greater than 20 cigarettes per day on average, in the month prior to screening, or be unable to abstain from smoking (or use of any nicotine-containing substance) for at least 6 hours (so that all pre-dose and post-dose/infusion-related assessments can be completed uninterrupted);
17. Positive UDS for amphetamine, cocaine (only on at Day −1), opioids, cannabinoids, and benzodiazepines. Positive result for benzodiazepines and cannabinoids acceptable as long as stable or decreasing due to long half-lives. Positive UDS for other drugs will result in rescheduling at discretion of investigator/designee; Positive breath alcohol test will also result in rescheduling at discretion of investigator/designee;
18. Exposure to pesticides or any other organophosphates (e.g. agricultural workers);
19. Inability to participate or successfully complete the study, in the opinion of their general practitioner or the Investigator, because the volunteer is:
    a. mentally or legally incapacitated, or unable to give consent for any reason;
    b. in custody due to an administrative or a legal decision, or under supervised parole, or being admitted to a sanitarium or social institution;
    c. unable to be contacted in case of emergency; or
    d. unlikely to cooperate or comply with the clinical study protocol or is unsuitable for any other reason.

Safety, Tolerability, and Immunogenicity Analysis

Safety

Vital signs, including blood pressure, heart rate (part of the PD parameters) and body temperature are monitored. Physical examinations, clinical laboratory tests, and 12-lead ECGs are performed, with 12-lead ECGs after each cocaine infusion, at pre-infusion, 30 minutes and 2 hours post-infusion, and 8 hour post-first infusion. Telemetry is performed for 4 hours immediately after each cocaine injection.

Samples for BChE and acetyl cholinesterase (AChE) activity are collected but are not all necessarily assayed. The activity of BChE and AChE is determined using a colorimetric method based on the Ellman assay, which serves as a neutralization assay for the endogenous enzymes. Sampling timepoints are at screening, pre-dose and 168 hours (Day 8), 240 hours (Day 11) and follow-up (Day 18±2) post-dose. The blood tests for Ellman assay take place before administration of cocaine (where relevant).

Intravenous infusions of cocaine are immediately terminated if any of the following occur:
1. Systolic BP of 180 mm Hg or greater;
2. Diastolic BP of 100 mm Hg or greater;
3. HR of 130 bpm or greater; or
4. Behavioral manifestations of psychostimulant toxicity (agitation, psychosis, or inability to cooperate with study procedures).

Subjects are considered to have not tolerated IV cocaine infusions if any of the following occur:
1. Acute chest pain or shortness of breath;
2. Systolic BP of 180 mm Hg or greater;
3. Diastolic BP of 120 mm Hg or greater;
4. HR of [220−age×0.85] bpm or greater (i.e., >than 170 bpm for a 20 year old subject);
5. Neurologic or psychiatric events (e.g., panic or psychosis);
6. Clinically significant ECG abnormalities (including heart block, three or more sustained ectopic ventricular beats, or tachyarrhythmias);
7. Stopping criteria for further cocaine infusion do not return to acceptable limits within appropriate time frames (e.g., 30 min);
8. Stopping criteria for further cocaine infusion are met for a second time within the protocol; or
9. Any condition that in the clinical judgment of the PI that is of sufficient magnitude to present a danger to the subject.

Tolerability of AlbuBChE IM Injection

Local tolerability and pain (evaluated by the visual analogue scale (VAS)) at the injection site are evaluated during the first 24 h after dosing. Timepoints are: 20 min, 1, 2, 4, 8 and 24 hours post AlbuBChE dose.

Adverse Events (AEs) are Monitored throughout the Study.

Immunogenicity (IG)

Samples for immunogenic levels are collected but are not all necessarily assayed. Titers for antibodies against HSA, human butyryl cholinesterase (hBChE) and AlbuBChE are evaluated. Sampling timepoints are: pre-dose and 168 hours (Day 8), 240 hours (Day 11) and follow-up (Day 18±2) post-dose. The blood tests for IG assays take place before administration of cocaine (where relevant).

Pharmacokinetic Variables and Sampling

To determine serum concentration of AlbuBChE, blood samples are collected before dosing and at several time points after dosing. Where the data permits, the following pharmacokinetic (PK) parameters are calculated:

$C_{max}$ maximum observed serum concentration
$t_{max}$ time to achieve $C_{max}$
$AUC_{(0-t)}$ area under the serum concentration-time curve from 0 h to the time of the last quantifiable concentration
$AUC_{(0-\infty)}$ area under the serum concentration-time curve extrapolated to infinity
$AUC_{ext}$ percentage of $AUC_{(0-\infty)}$ due to extrapolation from $t_{last}$ to infinity
$V_d/f$ apparent volume of distribution during terminal phase
$CL/f$ apparent total body clearance
$\lambda_z$ terminal elimination rate constant, estimated by linear regression on the terminal phase of the semi-logarithmic concentration versus time curve
$t_{1/2}$ apparent terminal elimination half-life
MRT mean residence time Additional parameters may be calculated if deemed necessary. Sampling timepoints for PR of AlbuBChE in serum are as follows: pre-dose and 20, 40 min, 1 hour, 1.5 hours, 2 hours, 3 hours, 4 hours, 6 hours, 8 hours, 12 hours, 18 hours, 24 hours (Day 2), 36 hours (Day 2), 48 hours (Day 3), 72 hours (Day 4), 96 hours (Day 5), 120 hours (Day 6), 144 hours (Day 7), 168 hours (Day 8), 192 hours (Day 9), and 216 hours (Day 10) post-dose. Where applicable, sampling timepoints for PK of AlbuBChE are taken just before cocaine infusion.

Pharmacodynamics Variables and Sampling

Blood samples are collected before dosing and at several time-points after each dosing of cocaine. In vivo cocaine levels (and its metabolites benzoylecgonine and ecgonine methyl ester) are determined by validated LC/MS-MS method and are correlated to AlbuBChE blood levels. Cocaine exposure ($C_{max}$, $t_{max}$, $AUC_{(0-t)}$, $AUC_{(0-\infty)}$ and $V_d$) and clearance (CL, $\lambda_z$, $t_{1/2}$) are determined. PD sampling timepoints of cocaine levels in serum after each cocaine dose are as follows: pre-dose, 2, 5, 10, 15, 30, 45, 60, 90, and 120 minutes post dose.

Blood pressure and heart rate are measured pre-infusion and 2, 5, 10, 15, 30, 45, 60, 90, 120, 180, 240, and 300 minutes post infusion.

Behavioral and Psychological Effects (Subjective Effects)

Subjective effects are measured using a computerized (21 CFR 11 validated) visual analogue scale (VAS). The time points for collection of subjective effects match with those for cocaine blood samples. The following set of VAS are: Drug Liking, Take Drug Again, Overall Drug Liking, High, Good Effects, Bad Effects, Feeling Rush, Desire for Cocaine, Feeling Anxious, Over-Stimulated, and Any Drug Effects.

PD sampling timepoints of VAS parameters after each cocaine dose are as follows: pre-dose, 2, 5, 10, 15, 30, 45, 60, 90, and 120 minutes post dose.

Urine Collection

Urine is collected for metabolic investigations over a 52 hour interval after cocaine administration on Day −1, Day 4 and Day 8. The collection ranges are: (i) immediately after cocaine dose, followed by collection intervals of (ii) two intervals of three hours, and (iii) nine intervals of six hours.

Statistical Analysis

Pharmacokinetics

PK parameters are derived from serum concentrations for each dose level (number of subjects, mean, SD, geometric mean (for AUCs and $C_{max}$), coefficient of variation, minimum, median, and maximum). Dose proportionality (for AlbuBChE only) using the power model is evaluated for $C_{max}$, $AUC_{0-t}$, and $AUC_{0-\infty}$.

Pharmacodynamics

Time course of PD effects (subjective and objective) is determined. PD parameters include: Emax (maximum effect), TEmax (time to Emax), time averaged area under the effect curve (TA_AUE), partial AUE for early time points, and cumulative AUE.

Safety

Safety data is determined using descriptive statistics and change from Baseline, where appropriate, for each treatment group. AEs are coded using the latest version of the Medical Dictionary for Regulatory Activities (MedDRA) and summarized by system organ class and preferred term.

Bioanalytical

Frozen serum samples for determining AlbuBChE concentrations and antibodies are shipped on dry ice for analysis. Analyses of cocaine and metabolite levels is performed using validated methods.

Results

Safety, Tolerability and Immunogenicity

AlbuBChE is safe to administer to humans. No significant safety issues are observed with intramuscular (IM) AlbuBChE doses of 50 mg to 300 mg. AlbuBChE is well tolerated, with no unacceptable side effects. Local tolerability and pain at the IM injection site are acceptable, with no significant adverse events. The administration of 50 mg to 300 mg of AlbuBChE as a single dose does not provoke a significant immune response. Titers for antibodies agains HSA, human butyryl cholinesterase (hBChE) and AlbuBChE are all within acceptable limits.

Pharmacokinetic Variables

Maximum observed serum concentration of AlbuBChE, $C_{max}$, increases with increasing dose of AlbuBChE. AlbuBChE absorption from the IM site of administration is rapid, with a short time to achieve $C_{max}$, $AUC_{(0-t)}$ and $AUC_{(0-\infty)}$ indicate that AlbuBChE levels persist for a significant and clinically useful amount of time. $V_d/f$ values indicate that the majority of AlbuBChE is present in the circulation during the terminal phase. CL/f values indicate that AlbuBChE is cleared from the body at an acceptable rate. Apparent terminal elimination half-life values indicate a weekly or twice weekly dosing of AlbuBChE to maintain therapeutic levels. The mean residence time of AlbuBChE is within clinically acceptable limits.

Pharmacodynamic Variables

Maximum observed serum concentration of cocaine, $C_{max}$, decreases with increasing dose of AlbuBChE. $C_{max}$ levels are achieved very rapidly following a 40 mg intravenous dose of cocaine, with a short $t_{max}$. $AUC_{(0-t)}$ and $AUC_{(0-\infty)}$ of cocaine and its metabolites benzolyecgonine and ecgonine methyl ester indicate that cocaine is more rapidly metabolized in subjects receiving a dose of AlbuBChE prior to cocaine exposure than subjects receiving placebo. Cocaine $AUC_{(0-t)}$ decreases as a function of AlbuBChE dose and increases as a function of time post-AlbuBChE administration. $V_d$ values indicate that the majority of cocaine is present in the circulation during the terminal phase. CL values indicate more rapid cocaine clearance following administration of AlbuBChE compared to placebo, with clearance rate decreasing as time post AlbuBChE administration increases. Similarly, apparent terminal elimination half-life values indicate more rapid cocaine clearance following administration of AlbuBChE compared to placebo, with clearance rate decreasing as time post AlbuBChE administration increases.

Behavioral and Phychological Effects

Subjects administered AlbuBChE report significantly different results on the visual analogue scale (VAS) compared to subjects administered placebo. AlbuBChE administration decreases cocaine liking. AlbuBChE administration decreases the desire to take cocaine again. AlbuBChE administration decreases overall drug liking. AlbuBChE administration decreases the "high" associated with cocaine exposure. AlbuBChE administration decreases the subjective feeling of "good effects" after cocaine exposure. AlbuBChE administration decreases subjective feeling of "rush" associated with cocaine exposure. AlbuBChE administration decreases the desire for cocaine. AlbuBChE administration reduces feelings of anxiousness following cocaine exposure. AlbuBChE administration reduces feelings of being overstimulated following cocaine exposure. AlbuBChE administration reduces the reporting of "any drug effects."

Subjects administered AlbuBChE prior to cocaine exposure do not report significantly different "bad effects" following AlbuBChE administration compared to subjects administered placebo. AlbuBChE reduces the feeling of "bad effects" following cocaine exposure.

Discussion

The present Example determines cocaine blood levels following multiple doses of cocaine subsequent to AlbuBChE administration, and determines the behavioral, psychological and safety effects of cocaine following multiple doses subsequent to AlbuBChE administration in an inpatient setting.

The primary measure of a successful treatment of cocaine abuse and dependence in an outpatient setting is a period of abstinence during and following treatment. The facilitation of a period of abstinence, such as a two or three week period of abstinence, indicates a successful treatment. Secondary outcome measures include reduction in cocaine levels or amount of cocaine intake, overall proportion of cocaine non-use days, proportion of successful subjects, the largest number of consecutive cocaine non-use days, and severity of cocaine dependence as evaluated, for example, by the cocaine selective severity assessment (CCSA).

Previous studies have found that AlbuBChE has a half life of approximately 8 hours in rats and have speculated that the potential half-life of AlbuBChE would range from 1 to several days in humans. (Brimijoin et al., 2008; Gao et al. 2009). Gao et al. noted that the observed half-life of monomeric AlbuBChE in rats is shorter than that of native tetrameric BChE, and speculated that the half-life of AlbuBChE could be increased by post-translational modifications such as polyethylene glycosylation.

The present Example determines that the half-life of AlbuBChE when administered by intramuscular injection is dose dependent, with half-life values increasing with increasing dose. The half-life values at the specified dosages allow for a weekly or twice weekly dosing schedule without the need for post-translational modifications such as polyethylene glycosylation.

Previous studies have also reported that intravenous administration of AlbuBChE to rats can cause a modest increase in blood pressure and mild lethargy. (Brimijoin et al. 2008). In constrast, a significant increase in blood pressure is not observed when AlbuBChE is administered to humans by intramuscular injection, nor is lethargy reported in a significant number of subjects.

Human subjects administered AlbuBChE do not report a significant increase in cocaine cravings. In contrast, desire to use cocaine is significantly decreased following AlbuBChE dosing and remains significantly depressed for up to one week following a single administration of AlbuBChE.

The findings of the present Example indicate that intramuscular administration of AlbuBChE to humans at the specified dosages does not result in any unacceptable side effects and that the specified dosages will allow for the successful treatment of biological effects of cocaine exposure.

References

Brimijoin, S., Gao, Y., Anker, J. J., Gliddon, L. A., LaEleur, D., Shah, R., Zhao, Q., Singh, M., and Carroll, M. E., "A Cocaine Hydrolase Engineered from Human Butyrylcholinesterase Selectively Blocks Cocaine Toxicity and Reinstatement of Drug Seeking in Rats". *Neuropsychopharmacology*, 33: 2715-2725, 2008.

Brogan, W. C. 3rd, Kemp, P. M., Bost, R. O., Glamann, D. B., Lange, R. A., Hillis, L. D., "Collection and handling of clinical blood samples to assure the accurate measurement of cocaine concentration," *J. Anal. Toxicol.* 1992 May-June; 16(3):152-4.

Davies, B. and Morris, T., "Physiological parameters in laboratory animals and humans," *Pharm. Res.*, 10: 1093-1095, 1993.

Diagnostic and Statistical Manual of Mental Disorders, American Psychiatric Publishing, Inc.; 4th edition (June 2000)

"Guidance for Industry: Estimating the Maximum Safe Starting Dose in Initial Clinical Trials for Therapeutics in Adult Healthy Volunteers," U.S. Department of Health and Human Services, Food and Drug Administration Center for Drug Evaluation and Research (CDER), July 2005.

Pan, Y., Gao, D., Yang, W., Cho, H., Yahg, G., Tai, H., Zhan, C., "Computational redesign of human butyrylcholinesterase for anticocaine medication," *PNAS*, 102(46):16656-61, 2005.

Sun, H., Shen, M., Pang, Y., Lockridge, O., Brimijoin, S., "Cocaine Metabolism Accelerated by a Re-Engineered Human Butyrylcholinesterase," *Journal of Pharmacology and Experimental Therapeutics*, 302(2): 710-16, 2002.

US Patent Application Publication No. 2008/0194481, published Aug. 14, 2008 (U.S. Ser. No. 11/932,823, filed Oct. 31, 2007).

Gao, et al. (2009) "An Albumin-Bytyrylcholinesterase for Cocaine Toxicity and Addiction: Catalytic and Pharmacokinetic Properties," NIH Public Access Author Manuscript, published in final edited form as *Chem. Biol. Interact.* 2008 September 25; 175(1-3): 83-87.

---

What is claimed is:

1. A method of attenuating a biological effect of a cocaine exposure in a primate comprising administering to the primate by intramuscular injection an amount of a fusion protein comprising:
 (a) a mutant butyrylcholinesterase (BChE) polypeptide comprising the sequence EDDIIIATKNGKVRGMNLTVFG- GTVTAFLGIPYAQPPLGRLRFKKPQSLT- KWSDIWNATKYAN SCCQNIDQSFPGFHGSEM- WNPNTDLSEDCLYLNVWIPAPKPKNATVLIWIY GGGFQTGTSSLH VYDGKFLARVERVIVVSM- NYRVGALGFLALPGNPEAPGN- MGLFDQQLALQWVQKNIAAFGGNP KSVTLF- GESSGAASVSLHLLSPGSHSLFTRAILQSGSFNA PWAVTSLYEARNRTLNLAKLTGC SRENETEIIK- CLRNKDPQEILLNEAFVVPYGTPLGVNF- GPTVDGDFLTDMPDILLELGQFKKT QIL- VGVNKDEGTWFLVGGAPGFSKDNNSIITRKEFQ EGLKIFFPGVSEFGKESILFHYTDWVD DQRPENYREALGDVVGDYNFICPALEFT- KKFSEWGNNAFFYYFEHRSSKLPWPEW- MGVMHGYE IEFVFGLPLERRDNYTKAEEILSR- SIVKRWANFAKYGNPNETQNNSTSWPVFKSTE QKYLTLN TESTRIMTKLRAQQCRFWTSFFPKV (SEQ ID NO:1), and
 (b) a human serum albumin (HSA) polypeptide comprising the sequence DAHKSEVAHRFKDLGEENFKALV- LIAFAQYLQQCPFEDHVKLVNEVTEFAK- TCVADESAENCD KSLHTLFGDKLCTVATLRE- TYGEMADCCAKQEPERNECFLQHKDDNPNLPR LVRPEVDVMCTA FHDNEETFLKKYLYEIAR- RHPYFYAPELLFFAKRYKAAFTEC- CQAADKAACLLPKLDELRDEG KASSAKQRLK- CASLQKFGERAFKAWAVARLSQRFPKAEFAEVS KLVTDLTKVHTECCHGDLLE CADDRADLAKYI- CENQDSISSKLKECCEKPLLEKSHCIAE- VENDEMPADLPSLAADFVESKDV CKNYAEAKD- VFLGMFLYEYARRHPDYSVVLLLRLAKTYETTL EKCCAAADPHECYAKVFDEFK PLVEEPQN- LIKQNCELFEQLGEYKFQNALLVRYT- KKVPQVSTPTLVEVSRNLGKVGSKCCKHP EAKRMPCAEDYLSVVLNQLCVLHEKT- PVSDRVTKCCTESLVNRRPCFSALEV- DETYVPKEFNA ETFTFHADICTLSEKER- QIKKQTALVELVKHKPKATKEQLKAVMDDFAA FVEKCCKADDKETC FAEEGKKLVAASQAALGL (SEQ ID NO: 2),
 wherein the amount of the fusion protein is effective to cause attenuation of the biological effect of the cocaine exposure in the primate.

2. The method of claim 1, wherein the fusion protein comprises the sequence EDDIIIATKNGKVRGMN- LTVFCGTVTAFLGIPYAQPPLGRLR- FKKPQSLTKWSDIWNATKYAN SCCQNIDQSFPG- FHGSEMWNPNTDLSEDCLYLNVWIPAPKPKNA TVLIWIYGGGFQTGTSSLH VYDGKFLARV- ERVIVVSMNYRVGALGFLALPGN- PEAPGNMGLFDQQLALQWVQKNIAAFGGNP KSVTLFGESSGAASVSLHLLSPGSH- SLFTRAILQSGSFNAPWAVTSLYEARN- RTLNLAKLTGC SRENETEIIKCLRNKD- PQEILLNEAFVVPYGTPLGVNDGPTVDGDFLTD MPDILLELGQFKKT QILVGVNKDEGTWFLVG- GAPGFSKDNNSIITRKEFQEGLKIFF- PGVSEFGKESILFHYTDWVD DQRPENYREAL- GDVVGDYNFICPALEFTKIFSEWGNNAFFYYFE HRSSKLPWPEWMGVMHGYE IEFVFGLPLERRD- NYTKAEEILSRSIVKRWANFAKYGNP- NETQNNSTSWPVFKSTEQKYLTLN TESTRIMT- KLRAQQCRFWTSFFPKVDAHKSEVAHRFKDLG EENFKALVLIAFAQYLQQCPFED HVKLVNEVTE- FAKTCVADESAENCDKSLHTLFGDKLCT- VATLRETYGEMADCCAKQEPERNEC FLQHKDD- NPNLPRLVRPEVDVMCTAFHDNEETFLKKYLYE IARRHPYFYAPELLFFAKRYKAA FTECCQAAD- KAACLLPKLDELRDEGKASSAKQRLK- CASLQKFGERAFKAWAVARLSQRFPKAE FAE- VSKLVTDLTKVHTECCHGDLLECADDRADLAK YICENQDSISSKLKECCEKPLLEKSHCI AEVEN- DEMPADLPSLAADFVESKDVCKNYAE- AKDVFLGMFLYEYARRHPDYSVVLLLRLAKTY ETTLEKCCAAADPHECYAKVFDEFK- PLVEEPQNLIKQNCELFEQLGEYK- FQNALLVRYTKKVP QVSTPTLVEVSRNLGKVG- SKCCKHPEAKRMPCAEDYLSVVLNQLCVLHEK TPVSDRVTKCCTE SLVNRRPCFSALEVDETYVP- KEFNAETFTFHADICTLSEKER- QIKKQTALVELVKHKPKATKE QLKAVMD- DFAAFVEKCCKADDKETCFAEEGKKLVAASQA ALGL (Residues 24 to 1137 of SEQ ID NO:4).

3. The method of claim 1, wherein the fusion protein is administered after the cocaine exposure.

4. The method of claim 3, wherein the fusion protein is administered up to one hour after the cocaine exposure.

5. The method of claim 1, wherein the biological effect is caused by cocaine overdose in the primate and the attenuating is treating or preventing the biological effect.

6. The method of claim 1, wherein the biological effect is an increase in blood pressure.

7. The method of claim 1, wherein the biological effect is an increase in heart rate or body temperature.

8. The method of claim 1, wherein the biological effect is cocaine seeking behavior in the primate.

9. The method of claim 8, wherein the cocaine seeking behavior occurs during a period of cocaine abstinence following the cocaine exposure.

10. The method of claim 8, wherein the cocaine seeking behavior follows a relapse.

11. The method of claim 8, wherein the administration of the fusion protein results in a lowering of total cocaine exposure in the primate than without the administration.

12. The method of claim 1, wherein the effective amount of the fusion protein is an amount which reduces the primate's serum cocaine level to about 0 ng/ml within about 30 minutes of a 1 mg/kg intravenous cocaine dose.

13. The method of claim 1, wherein the fusion protein is administered weekly or twice weekly.

14. The method of claim 1, wherein the primate is a human.

15. The method of claim 14, wherein the cocaine exposure is a single cocaine exposure of 10 mg to 60 mg or a recurring cocaine exposure wherein each single cocaine exposure of the recurring cocaine exposure is 10 mg to 60 mg.

16. The method of claim 15, wherein the effective amount of the fusion protein is an amount which reduces the human's serum cocaine level to about 0 ng/ml within about 30 minutes of a 40 mg intravenous cocaine dose.

17. The method of claim 14, wherein the effective amount of the fusion protein is 0.06 mg/kg to 5 mg/kg.

18. The method of claim 14, wherein the biological effect is a psychological effect.

19. The method of claim 18, wherein the psychological effect is a desire for cocaine.

20. The method of claim 14, wherein the effective amount of the fusion protein is 150 mg.

21. The method of claim 14, wherein the effective amount of the fusion protein is 300 mg.

* * * * *